US010465203B2

(12) United States Patent
Lu et al.

(10) Patent No.: US 10,465,203 B2
(45) Date of Patent: Nov. 5, 2019

(54) PLANTS HAVING ALTERED AGRONOMIC CHARACTERISTICS UNDER ABIOTIC STRESS CONDITIONS AND RELATED CONSTRUCTS AND METHODS INVOLVING ABIOTIC STRESS TOLERANCE GENES

(71) Applicant: PIONEER OVERSEAS CORPORATION, Johnston, IA (US)

(72) Inventors: Guihua Lu, Beijing (CN); Yang Gao, Beijing (CN); Junhua Liu, Beijing (CN); Guanfan Mao, Beijing (CN); Wei Wang, Beijing (CN); Xiping Wang, Beijing (CN); Changgui Wang, Beijing (CN); Cong Li, Beijing (CN); Huiting Li, Beijing (CN)

(73) Assignee: PIONEER OVERSEAS CORPORATION

( * ) Notice: Subject to any disclaimer, the term of this patent is extended or adjusted under 35 U.S.C. 154(b) by 97 days.

(21) Appl. No.: 15/319,427

(22) PCT Filed: Jul. 2, 2015

(86) PCT No.: PCT/CN2015/083222
§ 371 (c)(1),
(2) Date: Dec. 16, 2016

(87) PCT Pub. No.: WO2016/000642
PCT Pub. Date: Jan. 7, 2016

(65) Prior Publication Data
US 2017/0159068 A1 Jun. 8, 2017

(30) Foreign Application Priority Data

Jul. 3, 2014 (WO) ................ PCT/CN2014/081600

(51) Int. Cl.
*C12N 15/82* (2006.01)
*C07K 14/415* (2006.01)
(52) U.S. Cl.
CPC ........ *C12N 15/8273* (2013.01); *C07K 14/415* (2013.01); *C12N 15/8271* (2013.01)
(58) Field of Classification Search
None
See application file for complete search history.

(56) References Cited

U.S. PATENT DOCUMENTS

2004/0123343 A1* 6/2004 La Rosa ............. C07K 14/415
800/278
2007/0039076 A1 2/2007 Boukharov et al.

OTHER PUBLICATIONS

GenBank Accession AP005878, dated Feb. 16, 2008. (Year: 2008).*
Molitor et al. (Proceedings of the National Academy of Sciences (2016): 201523575. (Year: 2016).*
UniProt Accession No. Q7XPQ6, entered Oct. 1, 2003. (Year: 2003).*
International Search Report PCT/CN2015/083222 dated Sep. 16, 2015.
Sasaki, T. et al. ""*Oryza sativa* Japonica Group genomic DNA, chromosome 9, BAC clone:OSJNBb0012I09" retrieved from NCBI Database accession No. AP005878.2" Database Genbank, Feb. 16, 2008 (Feb. 16, 2008), pp. 1-113.
Tanaka, T. et al. ""*Oryza sative* Japonica Group Os05g0491400 mRNA, complete cds" retrieved from NCBI Database accession No. NM_001062444.1" Database Genbank, Jun. 8, 2010 (Jun. 8, 2010), pp. 1-8.
Sasaki, T. et al. ""*Oryza sative* Japonica Group genomic DNA chromosome 7, BAC clone:011200- C08" retrieved from NCBI Database accession No. AP003818.2" Database Genbank, Feb. 16, 2008 (Feb. 16, 2008), pp. 1-100.
Feng, Q. et al. ""*Oryza sative* genomic DNA, chromosome 4, BAC clone:OSJNBa0053K19, complete sequence" retrieved from NCBI Database accession No. AL606645.2" Database Genbank, Apr. 16, 2005 (Apr. 16, 2005), pp. 1-169.
Sasaki, T. et al. ""*Oryza sative* Japonica Group genomic DNA, chromosome 7, PAC clone:P0668C05" retrieved from NCBI Database accession No. AP004572.5" Database Genbank, Feb. 16, 2008 (Feb. 16, 2008), pp. 1-122.
Tanka, T. et al. ""Os09g0274900 [*Oryza sative* Japonica Group]" retrived from NCBI Database accession No. NP_001062748.1" Database Genbank, Jun. 8, 2010 (Jun. 8, 2010), pp. 1-7.
Sasaki, T. et al. ""*Oryza sative* Japonica Group genomic DNA, chromosome 7, 8-10 clone: OSJNBa0066H10" retrieved from NCBI Database accession No. AP005516.5" Database Genbank, Feb. 16, 2008 (Feb. 16, 2008), pp. 1-170.

* cited by examiner

*Primary Examiner* — Charles Logsdon

(57) ABSTRACT

Isolated polynucleotides and polypeptides, and recombinant DNA constructs useful for conferring improved nitrogen use efficiency and/or drought tolerance and/or cold tolerance; compositions (such as plants or seeds) comprising these recombinant DNA constructs; and methods utilizing these recombinant DNA constructs are disclosed. The recombinant DNA constructs comprise a polynucleotide operably linked to a promoter that is functional in a plant, wherein said polynucleotides encode low nitrogen tolerance polypeptides.

7 Claims, 7 Drawing Sheets
Specification includes a Sequence Listing.

SEQUENCE LISTING

<160> NUMBER OF SEQ ID NOS: 51

<210> SEQ ID NO 1
<211> LENGTH: 10952
<212> TYPE: DNA
<213> ORGANISM: Artificial Sequence
<220> FEATURE:
<223> OTHER INFORMATION: The nucleotide sequence of vector DP0005

<400> SEQUENCE: 1

```
gaattctcta gtcccgatct agtaacatag atgacaccgc gcgcgataat ttatcctagt      60
ttgcgcgcta tattttgttt tctatcgcgt attaaatgta taattgcggg actctaatca     120
taaaaaccca tctcataaat aacgtcatgc attacatgtt aattattaca tgcttaacgt     180
aattcaacag aaattatatg ataatcatcg caagaccggc aacaggattc aatcttaaga     240
aacgcggccg cttcagttgt ggcccagctt ggaggtcgac tcgcgaggat cctctagtcc     300
cgatctagta acatagatga caccgcgcgc gataatttat cctagtttgc gcgctatatt     360
ttgttttcta tcgcgtatta aatgtataat tgcgggactc taatcataaa aacccatctc     420
ataaataacg tcatgcatta catgttaatt attacatgct taacgtaatt caacagaaat     480
tatatgataa tcatcgcaag accggcaaca ggattcaatc ttaagaaacg cggccgcttc     540
agttgtggcc cagcttggag ggcggcgt cgcagtagcg gcccacggcg gcctcgtact     600
gcttgtagca cttgcccttc tccacctcct ccaggatctc gatgcggtgg tcctcgaagt     660
ggaagccggg catcttcagg gcggaggcgg gcttcttgga gcggtaggtg gtgtgcaggt     720
ggcaggtcag gtggcgaccg ccggggcact ccagggccat cagggactgg ccgcgcagca     780
cgccgtccac ctcgtacacg atctcggtgg agggctccca gcggccggcc ttgttctgca     840
tcacggggcc gtcggcgggg aagttgttgc ccaggatctt caccttgtac accaggcagt     900
cgccgtccag ggaggtgtcc tggtgggcgg tcaggaagcc gccgtcctcg taggtggtgg     960
tgcgctccca ggtgaagccc tcggggaggg actgcttgaa gtagtcgggg atgccggaca    1020
cgtacttgat gaaggccttg gagccgtaca tgcaggaggt ggacaggatg tggaaggcga    1080
agggcagggg gccgccctcg atcacctcga tcttcatctc ctgggtgccc tccagggggt    1140
tgccctcgcc cttgccggtg cacttgaagt agtggccgtt cacggtgccc tcgatggtgg    1200
tcctgaaggg catggtcttc ttcagcaaag aggccatggt ggcgaccggt accagatctc    1260
tgcagagaga tagatttgta gagagagact ggtgatttca gcgtgtcctc tccaaatgaa    1320
atgaacttcc ttatatagag gaagggtctt gcgaaggata gtgggattgt gcgtcatccc    1380
ttacgtcagt ggagatatca catcaatcca cttgctttga agacgtggtt ggaacgtctt    1440
ctttttccac gatgctcctc gtgggtgggg gtccatcttt gggaccactg tcggcagagg    1500
catcttgaac gatagccttt cctttatcgc aatgatggca tttgtaggtg ccaccttcct    1560
tttctactgt cctttttgatg aagtgacaga tagctgggca atggaatccg aggaggtttc    1620
ccgatattac cctttgttga aaagtctcaa tagccctttg gtcttctgag actgtatctt    1680
tgatattctt ggagtagacg agagtgtcgt gctccaccat gttcacatca atccacttgc    1740
tttgaagacg tggttggaac gtcttctttt tccacgatgc tcctcgtggg tggggtccca    1800
tctttgggac cactgtcggc agaggcatct tgaacgatag ccttt cctttt atcgcaatga    1860
tggcatttgt aggtgccacc ttcctttttct actgtccttt tgatgaagtg acagatagct    1920
gggcaatgga atccgaggag gtttcccgat attcccttt gttgaaaagt ctcaatagcc    1980
ctttggtctt ctgagactgt atctttgata ttcttggagt agacgagagt gtcgtgctcc    2040
```

```
accatgttgc caagctgctc taagcttggc actggccgtc gttttacaac gtcgtgactg    2100
ggaaaaccct ggcgttaccc aacttaatcg ccttgcagca catcccccctt tcgccagctg   2160
gcgtaatagc gaagaggccc gcaccgatcg cccttcccaa cagttgcgca gcctgaatgg    2220
cgaatgctag agcagcttga gcttggatca gattgtcgtt actatcagtg tttgacagga    2280
tatattggcg ggtaaaccta agagaaaaga gcgtttatta gaataacgga tatttaaaag    2340
ggcgtgaaaa ggtttatccg ttcgtccatt tgtatgtgca tgccaaccac agggttcccc    2400
tcgggatcaa agtactttga tccaacccct ccgctgctat agtgcagtcg gcttctgacg    2460
ttcagtgcag ccgtcttctg aaaacgacat gtcgcacaag tcctaagtta cgcgacaggc    2520
tgccgccctg ccctttttcct ggcgttttct tgtcgcgtgt tttagtcgca taaagtagaa   2580
tacttgcgac tagaaccgga gacattacgc catgaacaag agcgccgccg ctggcctgct    2640
gggctatgcc cgcgtcagca ccgacgacca ggacttgacc aaccaacggg ccgaactgca    2700
cgcggccggc tgcaccaagc tgttttccga agatcacc ggcaccaggc gcgaccgccc     2760
ggagctggcc aggatgcttg accacctacg ccctggcgac gttgtgacag tgaccaggct    2820
agaccgcctg gcccgcagca cccgcgacct actggacatt gccgagcgca tccaggaggc    2880
cggcgcgggc ctgcgtagcc tggcagagcc gtgggccgac accaccacgc cggccggccg    2940
catggtgttg accgtgttcg ccggcattgc cgagttcgag cgttccctaa tcatcgaccg    3000
cacccggagc gggcgcgagg ccgccaaggc ccgaggcgtg aagtttggcc cccgccctac    3060
cctcaccccg gcacagatcg cgcacgcccg cgagctgatc gaccaggaag gccgcaccgt    3120
gaaagaggcg gctgcactgc ttggcgtgca tcgctcgacc ctgtaccgcg cacttgagcg    3180
cagcgaggaa gtgacgccca ccgaggccag gcggcgcggt gccttccgtg aggacgcatt    3240
gaccgaggcc gacgccctgg cggccgccga gaatgaacgc caagaggaac aagcatgaaa    3300
ccgcaccagg acggccagga cgaaccgttt tcattaccg aagagatcga ggcggagatg    3360
atcgcggccg ggtacgtgtt cgagccgccc gcgcacgtct caaccgtgcg gctgcatgaa    3420
atcctggccg gtttgtctga tgccaagctg gcggcctggc cggccagctt ggccgctgaa    3480
gaaaccgagc gccgccgtct aaaaaggtga tgtgtatttg agtaaaacag cttgcgtcat    3540
gcggtcgctg cgtatatgat gcgatgagta aataaacaaa tacgcaaggg gaacgcatga    3600
aggttatcgc tgtacttaac cagaaaggcg ggtcaggcaa gacgaccatc gcaacccatc    3660
tagcccgcgc cctgcaactc gccggggccg atgttctgtt agtcgattcc gatccccagg    3720
gcagtgcccg cgattgggcg gccgtgcggg aagatcaacc gctaaccgtt gtcggcatcg    3780
accgcccgac gattgaccgc gacgtgaagg ccatcggccg gcgcgacttc gtagtgatcg    3840
acggagcgcc ccaggcggcg gacttggctg tgtccgcgat caaggcagcc gacttcgtgc    3900
tgattccggt gcagccaagc ccttacgaca tatgggccac cgccgacctg gtggagctgg    3960
ttaagcagcg cattgaggtc acggatgaa ggctacaagc ggcctttgtc gtgtcgcggg     4020
cgatcaaagg cacgcgcatc ggcggtgagg ttgccgaggc gctggccggg tacgagctgc    4080
ccattcttga gtcccgtatc acgcagcgcg tgagctaccc aggcactgcc gccgccggca    4140
caaccgttct tgaatcagaa cccgagggcg acgctgcccg cgaggtccag cgctggccg     4200
ctgaaattaa atcaaaactc atttgagtta atgaggtaaa gagaaaatga gcaaaagcac    4260
aaacacgcta agtgccggcc gtccgagcgc acgcagcagc aaggctgcaa cgttggccag    4320
cctggcagac acgccagcca tgaagcgggt caactttcag ttgccggcgg aggatcacac    4380
```

```
caagctgaag atgtacgcgg tacgccaagg caagaccatt accgagctgc tatctgaata    4440
catcgcgcag ctaccagagt aaatgagcaa atgaataaat gagtagatga attttagcgg    4500
ctaaaggagg cggcatggaa aatcaagaac aaccaggcac cgacgccgtg aatgcccca     4560 tgtgtggagg aacgggcggt tggccaggcg taagcggctg ggttgtctgc cggccctgca    4620
atggcactgg aacccccaag cccgaggaat cggcgtgacg gtcgcaaacc atccggcccg    4680
gtacaaatcg cgcggcgct gggtgatgac ctggtggaga agttgaaggc cgcgcaggcc     4740
gcccagcggc aacgcatcga ggcagaagca cgccccggtg aatcgtggca agcggccgct    4800
gatcgaatcc gcaaagaatc ccggcaaccg ccggcagccg gtgcgccgtc gattaggaag    4860
ccgcccaagg gcgacgagca accagatttt tcgttccga tgctctatga cgtgggcacc     4920
cgcgatagtc gcagcatcat ggacgtggcc gttttccgtc tgtcgaagcg tgaccgacga    4980
gctggcgagg tgatccgcta cgagcttcca gacgggcacg tagaggtttc cgcagggccg    5040
gccggcatgg ccagtgtgtg ggattacgac ctggtactga tggcggtttc ccatctaacc    5100
gaatccatga accgataccg ggaagggaag ggagacaagc ccggccgcgt gttccgtcca    5160
cacgttgcgg acgtactcaa gttctgccgg cgagccgatg gcggaaagca gaaagacgac    5220
ctggtagaaa cctgcattcg gttaaacacc acgcacgttg ccatgcagcg tacgaagaag    5280
gccaagaacg gccgcctggt gacggtatcc gagggtgaag ccttgattag ccgctacaag    5340
atcgtaaaga gcgaaaccgg gcggccggag tacatcgaga tcgagctagc tgattggatg    5400
taccgcgaga tcacagaagg caagaacccg gacgtgctga cggttcaccc cgattacttt    5460
ttgatcgatc ccggcatcgg ccgttttctc taccgcctgg cacgccgcgc cgcaggcaag    5520
gcagaagcca gatggttgtt caagacgatc tacgaacgca gtggcagcgc cggagagttc    5580
aagaagttct gtttcaccgt gcgcaagctg atcgggtcaa atgacctgcc ggagtacgat    5640
ttgaaggagg aggcggggca ggctggcccg atcctagtca tgcgctaccg caacctgatc    5700
gagggcgaag catccgccgg ttcctaatgt acggagcaga tgctagggca aattgcccta    5760 gcagggggaaa aaggtcgaaa aggtctcttt cctgtggata gcacgtacat tgggaaccca    5820
aagccgtaca ttgggaaccg gaacccgtac attgggaacc caaagccgta cattgggaac    5880
cggtcacaca tgtaagtgac tgatataaaa gagaaaaaag gcgattttttc cgcctaaaac    5940 tctttaaaac ttattaaaac tcttaaaacc cgcctggcct gtgcataact gtctggccag    6000
cgcacagccg aagagctgca aaaagcgcct acccttcggt cgctgcgctc cctacgcccc    6060
gccgcttcgc gtcggcctat cgcggccgct ggccgctcaa aaatggctgg cctacggcca    6120
ggcaatctac cagggcgcgg acaagccgcg ccgtcgccac tcgaccgccg cgcccacat    6180 caaggcaccc tgcctcgcgc gtttcggtga tgacggtgaa aacctctgac acatgcagct    6240
cccggagacg gtcacagctt gtctgtaagc ggatgccggg agcagacaag cccgtcaggg    6300
cgcgtcagcg ggtgttggcg ggtgtcgggg cgcagccatg acccagtcac gtagcgatag    6360
cggagtgtat actggcttaa ctatgcggca tcagagcaga ttgtactgag agtgcaccat    6420
atgcggtgtg aaataccgca cagatgcgta aggagaaaat accgcatcag gcgctcttcc    6480
gcttcctcgc tcactgactc gctgcgctcg gtcgttcggc tgcggcgagc ggtatcagct    6540
cactcaaagg cggtaatacg gttatccaca gaatcagggg ataacgcagg aaagaacatg    6600
tgagcaaaag gccagcaaaa ggccaggaac cgtaaaaagg ccgcgttgct ggcgtttttc    6660
cataggctcc gcccccctga cgagcatcac aaaaatcgac gctcaagtca gaggtggcga    6720
aacccgacag gactataaag ataccaggcg tttccccctg gaagctccct cgtgcgctct    6780
```

```
cctgttccga ccctgccgct taccggatac ctgtccgcct ttctcccttc gggaagcgtg   6840
gcgctttctc atagctcacg ctgtaggtat ctcagttcgg tgtaggtcgt tcgctccaag   6900
ctgggctgtg tgcacgaacc ccccgttcag cccgaccgct gcgccttatc cggtaactat   6960
cgtcttgagt ccaacccggt aagacacgac ttatcgccac tggcagcagc cactggtaac   7020
aggattagca gagcgaggta tgtaggcggt gctacagagt tcttgaagtg gtggcctaac   7080
tacggctaca ctagaaggac agtatttggt atctgcgctc tgctgaagcc agttaccttc   7140 ggaaaagag ttggtagctc ttgatccggc aaacaaacca ccgctggtag cggtggtttt    7200
tttgtttgca agcagcagat tacgcgcaga aaaaaggat ctcaagaaga tcctttgatc     7260
ttttctacgg ggtctgacgc tcagtggaac gaaaactcac gttaagggat tttggtcatg   7320
cattctaggt actaaaacaa ttcatccagt aaaatataat atttattttt ctcccaatca   7380
ggcttgatcc ccagtaagtc aaaaaatagc tcgacatact gttcttcccc gatatcctcc   7440
ctgatcgacc ggacgcagaa ggcaatgtca taccacttgt ccgccctgcc gcttctccca   7500
agatcaataa agccacttac tttgccatct ttcacaaaga tgttgctgtc tcccaggtcg   7560
ccgtgggaaa agacaagttc ctcttcgggc ttttccgtct ttaaaaaatc atacagctcg    7620
cgcggatctt taaatggagt gtcttcttcc cagttttcgc aatccacatc ggccagatcg   7680
ttattcagta agtaatccaa ttcggctaag cggctgtcta agctattcgt atagggacaa   7740
tccgatatgt cgatggagtg aaagagcctg atgcactccg catacagctc gataatcttt   7800
tcagggcttt gttcatcttc atactcttcc gagcaaagga cgccatcggc ctcactcatg   7860
agcagattgc tccagccatc atgccgttca aagtgcagga cctttggaac aggcagcttt   7920
ccttccagcc atagcatcat gtccttttcc cgttccacat cataggtggt ccctttatac   7980
cggctgtccg tcatttttaa atataggttt tcattttctc ccaccagctt atataccta    8040 gcaggagaca ttccttccgt atcttttacg cagcggtatt tttcgatcag ttttttcaat   8100
tccggtgata ttctcatttt agccatttat tatttccttc ctcttttcta cagtatttaa   8160 agataccccca agaagctaat tataacaaga cgaactccaa ttcactgttc cttgcattct   8220
aaaaccttaa ataccagaaa acagcttttt caaagttgtt ttcaaagttg gcgtataaca   8280
tagtatcgac ggagccgatt ttgaaaccgc ggtgatcaca ggcagcaacg ctctgtcatc   8340
gttacaatca acatgctacc ctccgcgaga tcatccgtgt ttcaaacccg gcagcttagt   8400
tgccgttctt ccgaatagca tcggtaacat gagcaaagtc tgccgcctta caacggctct   8460
cccgctgacg ccgtcccgga ctgatgggct gcctgtatcg agtggtgatt ttgtgccgag   8520
ctgccggtcg gggagctgtt ggctggctgg tggcaggata tattgtggtg taaacaaatt   8580
gacgcttaga caacttaata acacattgcg gacgttttta atgtactgaa ttaacgccga   8640
attaattcgg gggatctgga ttttagtact ggattttggt tttaggaatt agaaatttta   8700
ttgatagaag tattttacaa atacaaatac atactaaggg tttcttatat gctcaacaca   8760
tgagcgaaac cctataggaa ccctaattcc cttatctggg aactactcac acattattat   8820
ggagaaactc gagcttgtcg atcgacagat ccggtcggca tctactctat ttctttgccc   8880
tcggacgagt gctggggcgt cggtttccac tatcggcgag tacttctaca cagccatcgg   8940
tccagacggc cgcgcttctg cgggcgattt gtgtacgccc gacagtcccg gctccggatc   9000
ggacgattgc gtcgcatcga ccctgcgccc aagctgcatc atcgaaattg ccgtcaacca   9060
agctctgata gagttggtca agaccaatgc ggagcatata cgcccggagt cgtggcgatc   9120
```

| | | | | | |
|---|---|---|---|---|---|
| ctgcaagctc | cggatgcctc | cgctcgaagt | agcgcgtctg | ctgctccata | caagccaacc | 9180
| acggcctcca | gaagaagatg | ttggcgacct | cgtattggga | atccccgaac | atcgcctcgc | 9240
| tccagtcaat | gaccgctgtt | atgcggccat | tgtccgtcag | gacattgttg | gagccgaaat | 9300
| ccgcgtgcac | gaggtgccgg | acttcggggc | agtcctcggc | ccaaagcatc | agctcatcga | 9360
| gagcctgcgc | gacggacgca | ctgacggtgt | cgtccatcac | agtttgccag | tgatacacat | 9420
| ggggatcagc | aatcgcgcat | atgaaatcac | gccatgtagt | gtattgaccg | attccttgcg | 9480
| gtccgaatgg | gccgaacccg | ctcgtctggc | taagatcggc | cgcagcgatc | gcatccatag | 9540
| cctccgcgac | cggttgtaga | acagcgggca | gttcggtttc | aggcaggtct | tgcaacgtga | 9600
| caccctgtgc | acgcgggag | atgcaatagg | tcaggctctc | gctaaactcc | ccaatgtcaa | 9660
| gcacttccgg | aatcgggagc | gcggccgatg | caaagtgccg | ataaacataa | cgatctttgt | 9720
| agaaaccatc | ggcgcagcta | tttacccgca | ggacatatcc | acgccctcct | acatcgaagc | 9780
| tgaaagcacg | agattcttcg | ccctccgaga | gctgcatcag | gtcggagacg | ctgtcgaact | 9840
| tttcgatcag | aaacttctcg | acagacgtcg | cggtgagttc | aggcttttc | atatctcatt | 9900
| gcccccggg | atctgcgaaa | gctcgagaga | gatagatttg | tagagagaga | ctggtgattt | 9960
| cagcgtgtcc | tctccaaatg | aaatgaactt | ccttatatag | aggaaggtct | tgcgaaggat | 10020
| agtgggattg | tgcgtcatcc | cttacgtcag | tggagatatc | acatcaatcc | acttgctttg | 10080
| aagacgtggt | tggaacgtct | tcttttcca | cgatgctcct | cgtgggtggg | ggtccatctt | 10140
| tgggaccact | gtcggcagag | gcatcttgaa | cgatagcctt | tcctttatcg | caatgatggc | 10200
| atttgtaggt | gccaccttcc | ttttctactg | tccttttgat | gaagtgacag | atagctgggc | 10260
| aatggaatcc | gaggaggttt | cccgatatta | ccctttgttg | aaaagtctca | atagcccttt | 10320
| ggtcttctga | gactgtatct | ttgatattct | tggagtagac | gagagtgtcg | tgctccacca | 10380
| tgttatcaca | tcaatccact | tgctttgaag | acgtggttgg | aacgtcttct | ttttccacga | 10440
| tgctcctcgt | gggtggggt | ccatctttgg | gaccactgtc | ggcagaggca | tcttgaacga | 10500
| tagcctttcc | tttatcgcaa | tgatggcatt | tgtaggtgcc | accttccttt | tctactgtcc | 10560
| ttttgatgaa | gtgacagata | gctgggcaat | ggaatccgag | gaggtttccc | gatattaccc | 10620
| tttgttgaaa | agtctcaata | gcccttggt | cttctgagac | tgtatctttg | atattcttgg | 10680
| agtagacgag | agtgtcgtgc | tccaccatgt | tggcaagctg | ctctagccaa | tacgcaaacc | 10740
| gcctctcccc | gcgcgttggc | cgattcatta | atgcagctgg | cacgacaggt | tcccgactg | 10800
| gaaagcgggc | agtgagcgca | acgcaattaa | tgtgagttag | ctcactcatt | aggcacccca | 10860
| ggctttacac | tttatgcttc | cggctcgtat | gttgtgtgga | attgtgagcg | gataacaatt | 10920
| tcacacagga | aacagctatg | accatgatta | cg | | | 10952

<210> SEQ ID NO 2
<211> LENGTH: 1921
<212> TYPE: DNA
<213> ORGANISM: Artificial Sequence
<220> FEATURE:
<223> OTHER INFORMATION: The nucleotide sequence of DsRed expression cassette

<400> SEQUENCE: 2

| | | | | | |
|---|---|---|---|---|---|
| cgaagctggc | cgctctagaa | ctagtggatc | tcgatgtgta | gtctacgaga | agggttaacc | 60
| gtctcttcgt | gagaataacc | gtggcctaaa | ataagccga | tgaggataaa | taaaatgtgg | 120
| tggtacagta | cttcaagagg | tttactcatc | aagaggatgc | ttttccgatg | agctctagta | 180

```
gtacatcgga cctcacatac ctccattgtg gtgaaatatt ttgtgctcat ttagtgatgg      240
gtaaattttg tttatgtcac tctaggtttt gacatttcag ttttgccact cttaggtttt      300
gacaaataat ttccattccg cggcaaaagc aaaacaattt tattttactt ttaccactct      360
tagcttttca aatgtatcac aaatgccact ctagaaattc tgtttatgcc acagaatgtg      420
aaaaaaaaca ctcacttatt tgaagccaag gtgttcatgg catggaaatg tgacataaag      480
taacgttcgt gtataagaaa aaattgtact cctcgtaaca agagacggaa acatcatgag      540
acaatcgcgt ttggaaggct ttgcatcacc tttggatgat gcgcatgaat ggagtcgtct      600
gcttgctagc cttcgcctac cgcccactga gtccgggcgg caactaccat cggcgaacga      660
cccagctgac ctctaccgac cggacttgaa tgcgctacct tcgtcagcga cgatggccgc      720
gtacgctggc gacgtgcccc cgcatgcatg gcggcacatg gcgagctcag accgtgcgtg      780
gctggctaca aatacgtacc ccgtgagtgc cctagctaga aacttacacc tgcaactgcg      840
agagcgagcg tgtgagtgta gccgagtaga tcctcgccac catggcctcc tccgagaacg      900
tcatcaccga gttcatgcgc ttcaaggtgc gcatggaggg caccgtgaac ggccacgagt      960
tcgagatcga gggcgagggc gagggccgcc cctacgaggg ccacaacacc gtgaagctga     1020
aggtgacgaa gggcggcccc ctgcccttcg cctgggacat cctgtccccc cagttccagt     1080
acggctccaa ggtgtacgtg aagcaccccg ccgacatccc cgactacaag aagctgtcct     1140
tccccgaggg cttcaagtgg gagcgcgtga tgaacttcga ggacggcggc gtggcgaccg     1200
tgacccagga ctcctcccta caggacggct gcttcatcta caaggtgaag ttcatcggcg     1260
tgaacttccc ctccgacggc cccgtgatgc agaagaagac catgggctgg gaggcctcca     1320
ccgagcgcct gtaccccgc gacggcgtgc tgaagggcga cccacaag gccctgaagc       1380
tgaaggacgg cggccactac ctggtggagt tcaagtccat ctacatggcc aagaagcccg     1440
tgcagctgcc cggctactac tacgtggacg ccaagctgga catcacctcc cacaacgagg     1500
actacaccat cgtggagcag tacgagcgca ccgaggccgc caccacctg ttcctgtagc      1560
ggcccatgga tattcgaacg cgtaggtacc acatggttaa cctagacttg tccatcttct     1620
ggattggcca acttaattaa tgtatgaaat aaaaggatgc acacatagtg acatgctaat     1680
cactataatg tgggcatcaa agttgtgtgt tatgtgtaat tactagttat ctgaataaaa     1740
gagaaagaga tcatccatat ttcttatcct aaatgaatgt cacgtgtctt tataattctt     1800
tgatgaacca gatgcatttc attaaccaaa tccatataca tataaatatt aatcatatat     1860
aattaatatc aattgggtta gcaaaacaaa tctagtctag gtgtgttttg cgaatgcggc     1920
c                                                                    1921

<210> SEQ ID NO 3
<211> LENGTH: 2132
<212> TYPE: DNA
<213> ORGANISM: Oryza sativa

<400> SEQUENCE: 3
atggagttcg ggaggcctgc ttgcttccga gcactcttgc gtgcaagtgc tcagaaccgg       60
ggaaaatgga tgtgccatat ctttgttcat catctcaggg atgcaaatga tggtgtgctt      120
ctgagaaata tcccagcatt tgcaagaatt actcatttgg ttcatcgctc agcggctggg      180
ctacaggaag cggattcacc tgaccactgc tctcaaccaa attgtagagc tgtagtagag      240
ggtgtgctct tgatccaatc aaaagggatt ggagagcagt tcatttcctc ttcagatttt      300
aatggaagga aaagacaatt tgtttcagta aattcagaga tccaaaatga agcttacata      360
```

```
tatgagatct taataagcaa gtaagttaaa tagatagagg ttgttaaagg gaatatgtga      420
atgtgacgtg agtattatag aattttctca tcacttgtac acgttatgca gtctttgagc      480
caaagttaat acatactgat ggaaaggtta agctggtgac gacccttta aattagagaa       540 aattcactct atgccacgaa gcttgcccga ttcaacgatt tgccattgaa acaaattaaa      600
tacacatagt aaaattgaaa atggatttta aaaaaaatac tctatgaaat taatatatag      660
aaagttctat aaaagaatag tgctgagctc acctgaaaca tgcccttcaa ctgttgtatt      720
tgctaaaaaa acaatcctag tattacacta tggaattaag cagggaccat ctatataacg      780
agtcatcttt attcctcagt agtcgttcag taatattgtt ggtgaaaatc atcatctgaa      840
cagaagcaat atagaatgtc cagcctgcat agaagcattg gtgcttcagt cataggtacc      900
aaatattgga tcttaggatt gagaagtatc agtaaagccg tcatgacagt gttagggact      960
tctacagttg agttattgtg tagatccaaa ttctagtctc tacgcagatt cgtgaactca     1020
tcctgaaagt cctcttgaca tttatccacc acagcgattt atgcagctag acattgatta     1080
ggcgaaatac gccatcgtga agaaacaaat tcctaatgtc catttacaat gttttacta      1140 cgattatata tatgtcagtc tcacaaagat gggcatgcac gatggttaaa tttagatggc     1200
tgattaatct ctaagatgtg ttcctgttaa tcttccaagc tttggaataa tcactaacgg     1260
tttatgactt caagctaaat ctcagactct gaaatggttc tgatagaacc ttcagatgtt     1320
ataggggtca agcattggct gttctgtagt agaagtgtgc ataattctg ctatatatta      1380 tcagatgtaa ggaatgtatg gaataaacag tatgaaattt gtttcaacaa ttcatgcata     1440
ttacaaatgg acaacagttt ccgtggacta ataatgaatt ctctagtaaa aaagttaatg     1500
ttcaagtttt acactatcaa tcaaaatgca cacagtactc ccatttgcc agcctcgtct      1560 tcgaattcat tgaaaatcaa agagctagga gttaagaaaa agaaacgtc agggtttttc      1620 agtacttatc atgaaacaaa caatgatac ccgtgcttta atgtggaaca tattgataaa      1680
tatatgttaa atattataaa atgatagata gatttgttaa aatattgcta aaatatatgc     1740
taaatattac aaatacttgc atgccaattt gtggaaatta aatagattac aaatgatgtt     1800
gcatgtttgc atggggttaa atatgtagtt attgctagtg ggtaatgatg tgacatggtt     1860
gcgtgttgag atttagagtt aatgggctgt aactttatag aaagtatagg tcaaccccct      1920
caggatatag attatatata agaagaaagt cacaacaaac gacacaccac gtaattattg     1980
gaataaatgg gctaggccca atttaattca attaaaatat caagagccca caagtaatgt     2040
tagagacaat aatactgtct tgaaaattta ggtggaagaa cctcgactta aatagggtga    2100
tatggagatt cactgttgac cagtataggt ga                                   2132
```

<210> SEQ ID NO 4
<211> LENGTH: 441
<212> TYPE: DNA
<213> ORGANISM: Oryza sativa

<400> SEQUENCE: 4

```
atggagttcg ggaggcctgc ttgcttccga gcactcttgc gtgcaagtgc tcagaaccgg       60
ggaaaatgga tgtgccatat ctttgttcat catctcaggg atgcaaatga tggtgtgctt      120
ctgagaaata tcccagcatt tgcaagaatt actcatttgg ttcatcgctc agcggctggg      180
ctacaggaag cggattcacc tgaccactgc tctcaaccaa attgtagagc tgtagtagag      240
ggtgtgctct tgatccaatc aaaagggatt ggagagcagt tcatttcctc ttcagatttt      300
```

```
aatggaagga aaagacaatt tgtttcagta aattcagaga tccaaaatga agcttacata    360
tatgagatct taataagcaa gtggaagaac ctcgacttaa ataggggtgat atggagattc    420 actgttgacc agtataggtg a                                               441
```

<210> SEQ ID NO 5
<211> LENGTH: 146
<212> TYPE: PRT
<213> ORGANISM: Oryza sativa

<400> SEQUENCE: 5

```
Met Glu Phe Gly Arg Pro Ala Cys Phe Arg Ala Leu Leu Arg Ala Ser
1               5                   10                  15

Ala Gln Asn Arg Gly Lys Trp Met Cys His Ile Phe Val His His Leu
            20                  25                  30

Arg Asp Ala Asn Asp Gly Val Leu Leu Arg Asn Ile Pro Ala Phe Ala
        35                  40                  45

Arg Ile Thr His Leu Val His Arg Ser Ala Ala Gly Leu Gln Glu Ala
    50                  55                  60

Asp Ser Pro Asp His Cys Ser Gln Pro Asn Cys Arg Ala Val Val Glu
65                  70                  75                  80

Gly Val Leu Leu Ile Gln Ser Lys Gly Ile Gly Gln Phe Ile Ser
                85                  90                  95

Ser Ser Asp Phe Asn Gly Arg Lys Arg Gln Phe Val Ser Val Asn Ser
            100                 105                 110

Glu Ile Gln Asn Glu Ala Tyr Ile Tyr Glu Ile Leu Ile Ser Lys Trp
        115                 120                 125

Lys Asn Leu Asp Leu Asn Arg Val Ile Trp Arg Phe Thr Val Asp Gln
    130                 135                 140

Tyr Arg
145
```

<210> SEQ ID NO 6
<211> LENGTH: 894
<212> TYPE: DNA
<213> ORGANISM: Oryza sativa

<400> SEQUENCE: 6

```
gatccaacag acaactctaa cactagggcg ccggtcgcct catggctgag ctcccgccag     60
ccggatctgg tggccatgga gcggaagaga tggctgctgc cagggaagcg aagaagtgg    120 ctgccgctat atatgccat aaggcccgcc cgagcacaac acggtcggcg cttcgtgcca    180
tacctgtcca cgggctgcac ctcgggtcaa ggcacagccc actagcagtc gggccgtgcc    240
gtgccggccc gaaggcacgg gcggcccatc gtgccttttt tgaaataagt ctattttacg    300
ttcctattct ttgggttgtg ccatataata catttatttt tcctctctat tctttgtttc    360
gcatccctga actttgtgct gacccagcgt accgaggtag cagccaggca cggcacggct    420
gtcgggccag gccgtgccta ggccggacca aatcaccagg ccatcgggcc tctgactcta    480
tggccatcta cagcgctggc accaagctaa aaactgggtg agtcagatat atctcccttg    540
actccacatt gccatccccc aaggcccaa caacgagccc agcgatttag cgactaatca    600
ccacatgcaa gcccacgcgc aacaacagaa aggccacaat ggtttgctcc cggcctcggc    660
cgattccttc cttggcgtcc ttgttcctct tctgatcttc tccgtcctcc tcgatctaca    720
cgcagagtcg tccctgtcct gacagtgcac tctgtcattt tccacaaccg tctaacaagg    780
ataaatccgg cagatgatga gatgaagagg aagatgaact atggccacgg acatggaggg    840
```
cacaccgcac actacggtgc tggggccaga gcatgagtgc aaggcttcgg gacg    894

<210> SEQ ID NO 7
<211> LENGTH: 627
<212> TYPE: DNA
<213> ORGANISM: Oryza sativa

<400> SEQUENCE: 7
atggctgagc tcccgccagc cggatctggt ggccatggag cggaagagat ggctgctgcc    60
agggaagcgg aagaagtggc tgccgctata tatggccata aggcccgccc gagcacaaca   120
cggtcggcgc ttcgtgccat acctgtccac gggctgcacc tcgggtcaag cacagccca   180
ctagcagtcg ggccgtgccg tgccggcccg aaggcacggg cggcccatcg tgccttttt   240
gaaataagtc tattttacgt tcctattctt tgggttgtgc catataatac atttattttt   300
cctctctatt ctttgtttcg catccctgaa ctttgtgctg acccagcgta ccgaggtagc   360
agccaggcac ggcacggctg tcgggccagg ccgtgcctag gccggaccaa atcaccaggc   420
catcgggcct ctgactctat ggccatctac agcgctggca ccaagctaaa aactggagtc   480
gtccctgtcc tgacagtgca ctctgtcatt ttccacaacc gtctaacaag gataaatccg   540
gcagatgatg agatgaagag gaagatgaac tatggccacg acatggagg gcacaccgca   600
cactacggtg ctggggccag agcatga                                        627

<210> SEQ ID NO 8
<211> LENGTH: 208
<212> TYPE: PRT
<213> ORGANISM: Oryza sativa

<400> SEQUENCE: 8

Met Ala Glu Leu Pro Pro Ala Gly Ser Gly Gly His Gly Ala Glu Glu
1               5                   10                  15

Met Ala Ala Ala Arg Glu Ala Glu Val Ala Ala Ala Ile Tyr Gly
            20                  25                  30

His Lys Ala Arg Pro Ser Thr Thr Arg Ser Ala Leu Arg Ala Ile Pro
        35                  40                  45

Val His Gly Leu His Leu Gly Ser Arg His Ser Pro Leu Ala Val Gly
    50                  55                  60

Pro Cys Arg Ala Gly Pro Lys Ala Arg Ala Ala His Arg Ala Phe Phe
65                  70                  75                  80

Glu Ile Ser Leu Phe Tyr Val Pro Ile Leu Trp Val Pro Tyr Asn
                85                  90                  95

Thr Phe Ile Phe Pro Leu Tyr Ser Leu Phe Arg Ile Pro Glu Leu Cys
            100                 105                 110

Ala Asp Pro Ala Tyr Arg Gly Ser Ser Gln Ala Arg His Gly Cys Arg
        115                 120                 125

Ala Arg Pro Cys Leu Gly Arg Thr Lys Ser Pro Gly His Arg Ala Ser
    130                 135                 140

Asp Ser Met Ala Ile Tyr Ser Ala Gly Thr Lys Leu Lys Thr Gly Val
145                 150                 155                 160

Val Pro Val Leu Thr Val His Ser Val Ile Phe His Asn Arg Leu Thr
                165                 170                 175

Arg Ile Asn Pro Ala Asp Asp Glu Met Lys Arg Lys Met Asn Tyr Gly
            180                 185                 190

His Gly His Gly Gly His Thr Ala His Tyr Gly Ala Gly Ala Arg Ala
        195                 200                 205

<210> SEQ ID NO 9
<211> LENGTH: 547
<212> TYPE: DNA
<213> ORGANISM: Oryza sativa

<400> SEQUENCE: 9

| | | | | | |
|---|---|---|---|---|---|
| gcttggcttc | gacgacctta | tcatcgaatt | agcgtggcag | tttagctcgg | aagacaggca | 60 |
| gagcaagagg | tagcacatcc | tctccgaagg | gaagatatga | gcgaccagag | ctcgtaccct | 120 |
| aaccctgctc | aagggtacta | ccagggtccc | ccagcctcgg | cggcggccgg | ccaagataac | 180 |
| acggcggccg | gcggtggcaa | gtccaacgca | gccaagaaag | accaaccgag | cttcatggat | 240 |
| aacctccttg | cttgcctccc | ctgtgcccgc | ccagccgaag | ccaagaacga | cgcgagctaa | 300 |
| ctaaccttgc | tccatcaggc | agcctagcac | gggaaggaag | gctgcaaagc | tactgcatga | 360 |
| ttatgcccag | tgtttgtttg | attattcagc | atctaagtaa | gcacgtcgtt | aattagttca | 420 |
| atccggattg | ctcatttgcg | ttttgtgtac | tagtgaacga | tttatgtatt | tgtcgggggc | 480 |
| gcatgtaatt | taatttattc | cccttggat  | tcattattca | gtttatcttg | tcatgatttt | 540 |
| gtgagga | | | | | | 547 |

<210> SEQ ID NO 10
<211> LENGTH: 204
<212> TYPE: DNA
<213> ORGANISM: Oryza sativa

<400> SEQUENCE: 10

| | | | | | |
|---|---|---|---|---|---|
| atgagcgacc | agagctcgta | ccctaaccct | gctcaagggt | actaccaggg | tcccccagcc | 60 |
| tcggcggcgg | ccggccaaga | taacacggcg | gccggcggtg | gcaagtccaa | cgcagccaag | 120 |
| aaagaccaac | cgagcttcat | ggataacctc | cttgcttgcc | tccctgtgc  | ccgcccagcc | 180 |
| gaagccaaga | acgacgcgag | ctaa | | | | 204 |

<210> SEQ ID NO 11
<211> LENGTH: 67
<212> TYPE: PRT
<213> ORGANISM: Oryza sativa

<400> SEQUENCE: 11

Met Ser Asp Gln Ser Ser Tyr Pro Asn Pro Ala Gln Gly Tyr Tyr Gln
1               5                   10                  15

Gly Pro Pro Ala Ser Ala Ala Gly Gln Asp Asn Thr Ala Ala Gly
            20                  25                  30

Gly Gly Lys Ser Asn Ala Ala Lys Lys Asp Gln Pro Ser Phe Met Asp
        35                  40                  45

Asn Leu Leu Ala Cys Leu Pro Cys Ala Arg Pro Ala Glu Ala Lys Asn
    50                  55                  60

Asp Ala Ser
65

<210> SEQ ID NO 12
<211> LENGTH: 740
<212> TYPE: DNA
<213> ORGANISM: Oryza sativa

<400> SEQUENCE: 12

| | | | | | |
|---|---|---|---|---|---|
| gcacgaggca | ccaccgcagc | gaagcagttg | ccgccgcaaa | ccatggcgcc | cacgtcggcc | 60 |
| ggaaacctag | cccccgccac | cgccatcctc | gtcgtggtgg | tggcggtggt | cctggcggcg | 120 |

```
gcggcggcga gccaggacgg cgacgcgctg acggagttca ggaagggat gagcgacccc      180
gacggcgcgc tggcgagctg ggaccccgac ctggtgaacc cctgcacctg gttccgcgtc      240
acctgcaacg ccgacaaccg cgtcatccgc ctagatcttg aggagatgaa cctgtccggc      300
catctgtcgg ccgatcttgc gcgactggac cagctacaat ttatggaaat cgcttcgaac      360
aatatttaag gaccaattcc gccagagttt ggtaatctgg agaatttgat tagcctagac      420
ttgtgcaaca acaccatttc tgggccgata cctccgtcgc ttgggaaact caagtcctta      480
aaattcatga gaattgatca accttttta actgggccaa tcccaaacga gctggctggg      540
ctgtcaaacc tcatgatcct aaatgtatcc aacaacgatc tctgtgggac aatcccgacg      600
tccgggccgt cgatcactt ccctccgagc agctttgcca gcaacccgcg gctgaggtac      660
cccgggatgg acgacgatga caccggccgc tagatcatgg cagcatgaat taacgaataa      720
aaagaagagg acggcggcgg                                                  740

<210> SEQ ID NO 13
<211> LENGTH: 651
<212> TYPE: DNA
<213> ORGANISM: Oryza sativa

<400> SEQUENCE: 13
atggcgccca cgtcggccgg aaacctagcc ccgccaccg ccatcctcgt cgtggtggtg      60
gcggtggtcc tggcggcggc ggcggcgagc caggacggcg acgcgctgac ggagttcagg      120
aaggggatga cgaccccga cggcgcgctg gcgagctggg accccgacct ggtgaacccc      180
tgcacctggt tccgcgtcac ctgcaacgcc gacaaccgcg tcatccgcct agatcttgag      240
gagatgaacc tgtccggcca tctgtcggcc gatcttgcgc gactggacca gctacaattt      300
atggaaatcg cttcgaacaa tatttaagga ccaattccgc cagagtttgg taatctggag      360
aatttgatta gcctagactt gtgcaacaac accatttctg gccgatacc tccgtcgctt      420
gggaaactca agtccttaaa attcatgaga attgatcaca accttttaac tgggccaatc      480
ccaaacgagc tggctgggct gtcaaacctc atgatcctaa atgtatccaa caacgatctc      540
tgtgggacaa tcccgacgtc cgggccgttc gatcacttcc ctccgagcag ctttgccagc      600
aacccgcggc tgaggtaccc cgggatggac gacgatgaca ccggccgcta g              651

<210> SEQ ID NO 14
<211> LENGTH: 108
<212> TYPE: PRT
<213> ORGANISM: Oryza sativa

<400> SEQUENCE: 14

Met Ala Pro Thr Ser Ala Gly Asn Leu Ala Pro Ala Thr Ala Ile Leu
1               5                   10                  15

Val Val Val Ala Val Leu Ala Ala Ala Ala Ser Gln Asp
            20                  25                  30

Gly Asp Ala Leu Thr Glu Phe Arg Lys Gly Met Ser Asp Pro Asp Gly
        35                  40                  45

Ala Leu Ala Ser Trp Asp Pro Asp Leu Val Asn Pro Cys Thr Trp Phe
    50                  55                  60

Arg Val Thr Cys Asn Ala Asp Asn Arg Val Ile Arg Leu Asp Leu Glu
65                  70                  75                  80

Glu Met Asn Leu Ser Gly His Leu Ser Ala Asp Leu Ala Arg Leu Asp
                85                  90                  95
```

Gln Leu Gln Phe Met Glu Ile Ala Ser Asn Asn Ile
        100                105

<210> SEQ ID NO 15
<211> LENGTH: 1868
<212> TYPE: DNA
<213> ORGANISM: Oryza sativa

<400> SEQUENCE: 15

```
ggcttacgtg caggtggatc tatagatagc tactgctctg ctgctgctat taagtcagtc      60
tgtgctacga tcgaggagat gatgggagca gcggtgacca tggtggatcg gcgcatggcg     120
ttcgcggcgg aggccgacgt tgatagcaag gccgcctttg gattcttcgg aggcgagtgc     180
ttcgtcggcg agggcgacct ggtcaacccg cgccgccgc cgccgcagca gcagcaggtg      240
cacgagggcg gattcgccgc cgaggacgag agcgacggcg acgacgacga cgacgacgac     300
gacgacgtgg acgacatcga ggagctggag cgccgcatgt ggcgcgaccg cgtccggcac     360
aagcggctca aggagcttca gcagagccgc gccggggagg agagccgggc gggcgacgcc     420
ggcggcggag gcaggcagca gcggcagtcg caggagcagg cgcggcggaa gaagatgtcg     480
cgggcgcagg acgggatcct caagtacatg ctcaagatga tggaggtgtg caacgcgcag     540
gggttcgtgt acggcatcat cccggagaag gggaagccgg tgagcggcgc ctccgacaac     600
ctccgctcat ggtggaagga gaaggtccgc ttcgaccgca atggcccggc cgccatcgcc     660
aagtaccagg ccgacaacgc cgtgccgggg tgcgacggcg acgccggcgg cgccgcgccg     720
gcggggccgc actccctgca cgagctgcag gacaccacgc tgggatcgct gctctcggcg     780
ctcatgcagc actgcgaccc gccgcagcgc cgcttcccgc tggagaaggg cgtgccgccg     840
ccgtggtggc cggaggggag cgaggcgtgg tggcccgagg ccggcgtgcc caaggagctc     900
ggcccgccgc cgtacaagaa gccgcacgac ctcaagaagg cgtggaaggt cgccgtgctc     960
accgccgtca tcaagcacat gtcccccgac gtcgacaagg tccgccgcct cgtgcgtcag    1020
tccaagtgcc tccaggacaa gatgaccgcc aaggagatcg tcacctggct cgccgtcctc    1080
aagcaggagg aggacctcta tctcaagctc catcccggcg ccctcccccc gccgctctcc    1140
gccgcgtcct tcaacgccag cgtctccggc gagtacgacg tcgaaggagt cgacggcgac    1200
gaggccggga caacaacct gcagaaggcg cagaacgacg cgaccgcgtt catggacctc    1260
accaccacca tggatgctgc tctgagcaac aacaagttcc tgatcatgcc gctgatgaag    1320
gaagaggcca tcgacgtcga cttcatccag aagaggagcg agccggagct gatgctgagc    1380
agcgacagcc atgcccgcgt ctacacctgc ggcaacgtgc agtgcccgca cagcaactac    1440
gcgctcggct cctcgaccg caacgaacgc aacgcccatc agtacgcctg caagcacaac    1500
gccgccgccg ccgccgccga gagcaagccg ccgccgccgc acatcttcga gccactcggc    1560
agcttcgact tcgacctccc cgtcgacggc cagagatgcc tcgccgggct gatgaccatg    1620
tacgacaacg acgtcgccgc cgccacgcag atgcaccacc accaccatca gcagcagcag    1680
gctaatttct tcatccgcga cgacgcgccg ttcggaggcg acgtcgccgc cacggcggcg    1740
gcggcgccgg agttcaggtt cagttcaaat ttcaacgtga caggagggg cgccgtggac    1800
tacggcggcg ccatgcagca accgccggcg aagtacgccg atccaactg gttctactga    1860
aacgaatt                                                                1868
```

<210> SEQ ID NO 16
<211> LENGTH: 1782
<212> TYPE: DNA

<213> ORGANISM: Oryza sativa

<400> SEQUENCE: 16

```
atgatgggag cagcggtgac catggtggat cggcgcatgg cgttcgcggc ggaggccgac    60
gttgatagca aggccgcctt tggattcttc ggaggcgagt gcttcgtcgg cgagggcgac   120
ctggtcaacc cggcgccgcc gccgccgcag cagcagcagg tgcacgaggg cggattcgcc   180
gccgaggacg agagcgacgg cgacgacgac gacgacgacg acgacgacgt ggacgacatc   240
gaggagctgg agcgccgcat gtggcgcgac cgcgtccggc acaagcggct caaggagctt   300
cagcagagcc gcgccgggag ggagagccgg cggggcgacg ccggcggcgg aggcaggcag   360
cagcggcagt cgcaggagca ggcgcggcgg aagaagatgt cgcgggcgca ggacgggatc   420
ctcaagtaca tgctcaagat gatggaggtg tgcaacgcgc aggggttcgt gtacggcatc   480
atcccggaga aggggaagcc ggtgagcggc gcctccgaca acctccgctc atggtggaag   540
gagaaggtcc gcttcgaccg caatggcccg gcgccatcg ccaagtacca ggccgacaac   600
gccgtgccgg ggtgcgacgg cgacgccggc ggcgccgcgc cggcggggcc gcactccctg   660
cacgagctgc aggacaccac gctgggatcg ctgctctcgg cgctcatgca gcactgcgac   720
ccgccgcagc gccgcttccc gctggagaag ggcgtgccgc cgccgtggtg gcggaggggg   780
agcgaggcgt ggtggcccga ggccggcgtg cccaaggagc tcggcccgcc gccgtacaag   840
aagccgcacc acctcaagaa ggcgtggaag gtcgccgtgc tcaccgccgt catcaagcac   900
atgtccccg acgtcgacaa ggtccgccgc ctcgtgcgtc agtccaagtg cctccaggac   960
aagatgaccg ccaaggagat cgtcacctgg ctcgccgtcc tcaagcagga ggaggacctc  1020
tatctcaagc tccatcccgg cgccctcccc ccgccgctct ccgccgcgtc cttcaacgcc  1080
agcgtctccg gcgagtacga cgtcgaagga gtcgacggcg acgaggccgg gaacaacaac  1140
ctgcagaagg cgcagaacga cgcgaccgcg ttcatggacc tcaccaccac catggatgct  1200
gctctgagca acaacaagtt cctgatcatg ccgctgatga aggaagaggc catcgacgtc  1260
gacttcatcc agaagaggag cgagccggag ctgatgctga gcagcgacag ccatgcccgc  1320
gtctacacct gcggcaacgt gcagtgcccg cacagcaact acgcgctcgg cttcctcgac  1380
cgcaacgaac gcaacgccca tcagtacgcc tgcaagcaca acgccgccgc cgccgccgcc  1440
gagagcaagc cgccgccgcc gcacatcttc gagccactcg gcagcttcga cttcgacctc  1500
cccgtcgacg gccagagatg cctcgccggg ctgatgacca tgtacgacaa cgacgtcgcc  1560
gccgccacgc agatgcacca ccaccaccat cagcagcagc aggctaattt cttcatccgc  1620
gacgacgcgc cgttcggagg cgacgtcgcc gccacggcgg cggcggcgcc ggagttcagg  1680
ttcagttcaa atttcaacgt gacaggaggg ggcgccgtgg actacggcgg cgccatgcag  1740
caaccgccgg cgaagtacgc cggatccaac tggttctact ga                    1782
```

<210> SEQ ID NO 17
<211> LENGTH: 593
<212> TYPE: PRT
<213> ORGANISM: Oryza sativa

<400> SEQUENCE: 17

```
Met Met Gly Ala Ala Val Thr Met Val Asp Arg Arg Met Ala Phe Ala
1               5                   10                  15

Ala Glu Ala Asp Val Asp Ser Lys Ala Ala Phe Gly Phe Phe Gly Gly
            20                  25                  30

Glu Cys Phe Val Gly Glu Gly Asp Leu Val Asn Pro Ala Pro Pro Pro
```

```
            35                  40                  45
Pro Gln Gln Gln Gln Val His Glu Gly Gly Phe Ala Ala Glu Asp Glu
 50                  55                  60

Ser Asp Gly Asp Asp Asp Asp Asp Asp Val Asp Asp Ile
 65              70              75              80

Glu Glu Leu Glu Arg Met Trp Arg Asp Val Arg His Lys Arg
             85              90              95

Leu Lys Glu Leu Gln Gln Ser Arg Ala Gly Arg Glu Ser Arg Ala Gly
            100             105             110

Asp Ala Gly Gly Gly Arg Gln Gln Arg Gln Ser Gln Glu Gln Ala
            115             120             125

Arg Arg Lys Lys Met Ser Arg Ala Gln Asp Gly Ile Leu Lys Tyr Met
            130             135             140

Leu Lys Met Met Glu Val Cys Asn Ala Gln Gly Phe Val Tyr Gly Ile
145                 150             155                 160

Ile Pro Glu Lys Gly Lys Pro Val Ser Gly Ala Ser Asp Asn Leu Arg
                165             170             175

Ser Trp Trp Lys Glu Lys Val Arg Phe Asp Arg Asn Gly Pro Ala Ala
            180             185             190

Ile Ala Lys Tyr Gln Ala Asp Asn Ala Val Pro Gly Cys Asp Gly Asp
            195             200             205

Ala Gly Gly Ala Ala Pro Ala Gly Pro His Ser Leu His Glu Leu Gln
210             215             220

Asp Thr Thr Leu Gly Ser Leu Leu Ser Ala Leu Met Gln His Cys Asp
225             230             235             240

Pro Pro Gln Arg Arg Phe Pro Leu Glu Lys Gly Val Pro Pro Trp
            245             250             255

Trp Pro Glu Gly Ser Glu Ala Trp Trp Pro Glu Ala Gly Val Pro Lys
            260             265             270

Glu Leu Gly Pro Pro Tyr Lys Lys Pro His Asp Leu Lys Lys Ala
            275             280             285

Trp Lys Val Ala Val Leu Thr Ala Val Ile Lys His Met Ser Pro Asp
290             295             300

Val Asp Lys Val Arg Arg Leu Val Arg Gln Ser Lys Cys Leu Gln Asp
305             310             315             320

Lys Met Thr Ala Lys Glu Ile Val Thr Trp Leu Ala Val Leu Lys Gln
            325             330             335

Glu Glu Asp Leu Tyr Leu Lys Leu His Pro Gly Ala Leu Pro Pro Pro
            340             345             350

Leu Ser Ala Ala Ser Phe Asn Ala Ser Val Ser Gly Glu Tyr Asp Val
            355             360             365

Glu Gly Val Asp Gly Asp Glu Ala Gly Asn Asn Leu Gln Lys Ala
            370             375             380

Gln Asn Asp Ala Thr Ala Phe Met Asp Leu Thr Thr Met Asp Ala
385                 390             395             400

Ala Leu Ser Asn Asn Lys Phe Leu Ile Met Pro Leu Met Lys Glu Glu
                405             410             415

Ala Ile Asp Val Asp Phe Ile Gln Lys Arg Ser Glu Pro Glu Leu Met
            420             425             430

Leu Ser Ser Asp Ser His Ala Arg Val Tyr Thr Cys Gly Asn Val Gln
            435             440             445

Cys Pro His Ser Asn Tyr Ala Leu Gly Phe Leu Asp Arg Asn Glu Arg
            450             455             460
```

```
Asn Ala His Gln Tyr Ala Cys Lys His Asn Ala Ala Ala Ala Ala
465                 470                 475                 480

Glu Ser Lys Pro Pro Pro His Ile Phe Glu Pro Leu Gly Ser Phe
            485                 490                 495

Asp Phe Asp Leu Pro Val Asp Gly Gln Arg Cys Leu Ala Gly Leu Met
                500                 505                 510

Thr Met Tyr Asp Asn Asp Val Ala Ala Ala Thr Gln Met His His His
            515                 520                 525

His His Gln Gln Gln Gln Ala Asn Phe Phe Ile Arg Asp Asp Ala Pro
        530                 535                 540

Phe Gly Gly Asp Val Ala Ala Thr Ala Ala Ala Ala Pro Glu Phe Arg
545                 550                 555                 560

Phe Ser Ser Asn Phe Asn Val Thr Gly Gly Gly Ala Val Asp Tyr Gly
                565                 570                 575

Gly Ala Met Gln Gln Pro Pro Ala Lys Tyr Ala Gly Ser Asn Trp Phe
            580                 585                 590

Tyr

<210> SEQ ID NO 18
<211> LENGTH: 829
<212> TYPE: DNA
<213> ORGANISM: Oryza sativa

<400> SEQUENCE: 18
ggccagtaat cacatacaca gtttgacaca aactaggaat taattgaagt agctactgaa      60
aaccgtagat agcaaactcc aaattaatta gtcgacttta aattggatcg cgtgtctaat     120
atgaacagta taatttatga tgtatcagat gatttcgggg gctaggaaga aagagctgtt     180
catgggacat ccgtacagcg ccggcgacca gccgaaaccg ggggcgggca ccgtcgagtt     240
cgtgctgcac aacaccgtcc acaactggac cggcgacccg aggcagccga acggcgagga     300
catgggcatg ttctactcgg cggcgcgcga cccggtgttc ttcgcgcacc acggcaacgt     360
cgaccgcatg tggtacattc gccacggcct cttcccccgc gacaccgact tcaccgaccc     420
cgactggctc gacgcgacct tcctgttcta cgacgaggag gcccgcctag tccgcgttcg     480
cgtccgcgac tccctcgacg aggccgcgct gcggtacacg taccaggacg ttggccccct     540
gccgtggctg aacgccaagc cgtccacggg acccgccggc gccctgccgg ggaccctgga     600
caagaccgtg cgggtggcct tgacgaggcc caagacgtcg aggagccgca aggagaagga     660
cgccgaggag gaggcgcctg tcatcgaggg gatcgaggtc cccgaccact ccgcgtacgt     720
taagttcgac gtgttcgtga acgcgcccga gaacgccgac gtcgcgtcgc gctgacgcca     780
cacggggtcc accgcgagga gaggaagcgt tctccgagaa agacggtgg               829

<210> SEQ ID NO 19
<211> LENGTH: 636
<212> TYPE: DNA
<213> ORGANISM: Oryza sativa

<400> SEQUENCE: 19
atgtatcaga tgatttcggg ggctaggaag aaagagctgt tcatgggaca tccgtacagc      60
gccggcgacc agccgaaacc gggggcgggc accgtcgagt tcgtgctgca acaccgtc      120 cacaactgga ccggcgaccc gaggcagccg aacggcgagg acatgggcat gttctactcg     180
gcggcgcgcg acccggtgtt cttcgcgcac cacggcaacg tcgaccgcat gtggtacatt     240
```

```
cgccacggcc tcttccccg cgacaccgac ttcaccgacc ccgactggct cgacgcgacc    300
ttcctgttct acgacgagga ggcccgccta gtccgcgttc gcgtccgcga ctccctcgac    360
gaggccgcgc tgcggtacac gtaccaggac gttggcccc tgccgtggct gaacgccaag    420
ccgtccacgg gacccgccgg cgccctgccg gggaccctgg acaagaccgt gcgggtggcc    480
ttgacgaggc ccaagacgtc gaggagccgc aaggagaagg acgccgagga ggaggcgcct    540
gtcatcgagg ggatcgaggt ccccgaccac tccgcgtacg ttaagttcga cgtgttcgtg    600
aacgcgcccg agaacgccga cgtcgcgtcg cgctga                              636
```

<210> SEQ ID NO 20
<211> LENGTH: 211
<212> TYPE: PRT
<213> ORGANISM: Oryza sativa

<400> SEQUENCE: 20

```
Met Tyr Gln Met Ile Ser Gly Ala Arg Lys Lys Glu Leu Phe Met Gly
1               5                   10                  15

His Pro Tyr Ser Ala Gly Asp Gln Pro Lys Pro Gly Ala Gly Thr Val
            20                  25                  30

Glu Phe Val Leu His Asn Thr Val His Asn Trp Thr Gly Asp Pro Arg
        35                  40                  45

Gln Pro Asn Gly Glu Asp Met Gly Met Phe Tyr Ser Ala Ala Arg Asp
    50                  55                  60

Pro Val Phe Phe Ala His His Gly Asn Val Asp Arg Met Trp Tyr Ile
65                  70                  75                  80

Arg His Gly Leu Phe Pro Arg Asp Thr Asp Phe Thr Asp Pro Asp Trp
                85                  90                  95

Leu Asp Ala Thr Phe Leu Phe Tyr Asp Glu Glu Ala Arg Leu Val Arg
            100                 105                 110

Val Arg Val Arg Asp Ser Leu Asp Glu Ala Ala Leu Arg Tyr Thr Tyr
        115                 120                 125

Gln Asp Val Gly Pro Leu Pro Trp Leu Asn Ala Lys Pro Ser Thr Gly
    130                 135                 140

Pro Ala Gly Ala Leu Pro Gly Thr Leu Asp Lys Thr Val Arg Val Ala
145                 150                 155                 160

Leu Thr Arg Pro Lys Thr Ser Arg Ser Arg Lys Glu Lys Asp Ala Glu
                165                 170                 175

Glu Glu Ala Pro Val Ile Glu Gly Ile Glu Val Pro Asp His Ser Ala
            180                 185                 190

Tyr Val Lys Phe Asp Val Phe Val Asn Ala Pro Glu Asn Ala Asp Val
        195                 200                 205

Ala Ser Arg
    210
```

<210> SEQ ID NO 21
<211> LENGTH: 6631
<212> TYPE: DNA
<213> ORGANISM: Oryza sativa

<400> SEQUENCE: 21

```
atgcccgacc cgaaaatgtg cctgtagttt aacatccctc ctcaggagtt aggcccaacc     60
attggcccat tatcagatgg tatatatttc acaacttatt aaccctaacc ctagtttctc    120
agttctcact ccctcccgtg tctctctgtc tctgtctagc ggcggcatgg cgcaccatgc    180
acaggagtcg ggaaggggcg cgctcagga gggggcggcg ttgggaggcg gaggtagagg    240
```

```
cgacggtgct tgggggggcgg cacggcggcg gcgctcggga gggggtggca cggcggcagc    300
gcacgggagg ggtggcgcgg aggggcggcg cggcggcgga cagatgacgg cgcgacggca    360
cacgggaggg gtggcacgac ggcgcggcg cgcacgggag ggagcaggcg gcggcggcgc     420
acgggagggg cggcggcggc acacgggagg ggcggcgcgg tgacgcagag acgacggcgg    480
tggctgtgca cagatgacgg caagcatttt ctgaaattga tgttgtgtat gtgtatctta    540
gtatttgtgt atgtatattt gtgattttgt gtatgtgaat gccagatctg aaattttgtg    600
tcgtgtacat gtggttttgc tgtgattaaa tttgttttta actttgtggt atccagtggg    660
tacccgttgg gcatgcccgt gcccgtcggg catgggcacg ggcatggagt tttgcccgat    720
agagctggcg ggcgtgggtc gggcacgggc atgtgggtct cgggtcgggc atggaatcgc    780
tctgcccgtg cccgacccga cccactgcca tccctaaggt ttggtagcac ccattcgctg    840
cctttcgcca gagatcaatt cttggcgagt gaagtcgtcg acggcgagta catgctctac    900
catcttcgcc gacgacgtca cctcctcctc cgcgaccgcc atgtcgtcct tcctttcgtc    960
tccgtctccg ggcgcggtgc ggatggtgac ggcgacccca gaggagcacg gtcggaggaa   1020 gtggggagc cgcggcggcc ggagatggag gaggtgaggc gcatacccag tggggtagcg    1080
cggtggccgg cggccggaag aagaaagagg aggcgtggtt ggaggaggaa gggggagcgg    1140
cagccaccag aggaggggag aagggggaa gagcggcggt cggagatgga ggagagaatg     1200
actttcacaa agaactgtga aacttgtggt aagtattatt ttttccgtgt cttcgtccta    1260
tgtggtagtc tcagctcctc aaactagtgc gaatggcctt aacacaccaa actggtagcc    1320
tcaatcgatc actacgaggc tttattactt cattttgca aaattcctcc atcacaagtg     1380
gagcgcgtta accgtaggat tgttttcaag gattcttgca tgggttgaac acttgaacta    1440
cttactaatg ataatgaaaa ttcactaaaa ttcttccgtt tcaatggaaa cgtaaattca    1500
gccatattaa tttctctaat cccaaatctt ccaaggcctt gctgaggctc cattaggacg    1560
cagaaatttt acagtatttt tttacatgaa tccgctcagt ttgtactacg tattattatt    1620
cattcttcaa attcccaatc caaaatgttt tagaaactcg tatgttgaaa actgggcct     1680 cgaatggtaa aagaggccca gaattcaccc gcctcctttg accctaccaa aatttaccgt    1740
tgaccatgtt actctccagc cgcctccacc tcgccacgcc ctcctcgccg gcaacctgcc    1800
cctctccgct ccgccgccgc cgccgcctcg gcctcccgga ccacgaacg cgtcgccctc     1860 cgccactagc ttccaagaac cccgcgccgc cgcagccgca ccgttgccg ctgtcctggc     1920 tgtcgccgag gcggcaatgg cggtggcgga gcgactacgg cgacgccgac gccgccgaag    1980
aagaatcacc ggcgccgctc gtcgaggacg gggtatccgg tggagggggag aagaagagct    2040 tctgggcggc ggtgagcctc atcgtcggaa cggcggtggg gccggggatg ctggggctgc    2100
cgtccgccac catccgctcc gggccggtcc cgtccacggc ggcgatcgtg ctctcgtggg    2160
tctacgtggt gtcctccatc gtcctcgtcg cggagctcag cttcgccgcg atggaggacg    2220
gcggcgtcga cgaggtcagc ttcacgggac ttgcgtcgag caccttgggg gcgacgctcg    2280
gggcggtcgt ggccgtcgtc tacgccgccc tcagcttctc cctgctcgtc gcctgcgtcg    2340
ccggcatcgg ctcgctggtg tcccagctct tcccggcggt ggatccggcc ttggccaacg    2400
ccatcttccc gtgcttcgcc gggacgctca tcgcgttctt ccccttcaag gccgtcgacg    2460
gcgccaaccg cgccgctctgc ggcctgatgc tcgcctccat caccgcgctt gttgtcaccg    2520
gcgtttccgt cggccggagc agcatgctga gatcgctcgg ctacgcctgc tggcgccctg    2580
```

```
ctaccatcct gcctgcaatt ccggtgaccg tcctgacgct tgggttccat gtcatcacgc   2640
cgttcatctg caagattgtg ggggattcag tgtacgatgc gcggcgcgca atactgatcg   2700
gcggtgccgt cccattggcc atggtgttgt cctggaatgc cgtcattctc gggttggcaa   2760
gttccagtgg cggtgcgaga ttcgatgatc caattaagct gctgctctcg gtgaatccag   2820
cagcattgcc tgccgttcga ggctttgcgt ttgccgcatt ggcgacgagc ttgataggat   2880
acgcggtgag ctttccgaag cagctggctg atacagtgga gttgattggg cagaggtttt   2940
ctccgaagcg aggaattggg cagctctctg aatctagcgg tggccatgga agaaatgggg   3000
ctattctcac atggattgtg ctgattattc ctatcgttat tgcgtcgttc ttctcagcgg   3060
ccttctccaa ggcactggat tttgctgggg tttatgcaaa ctgcttcctt tttgggatcc   3120
tccctcctgt catggcctgg attcaccggt cacagaagag aaagaggtaa catcaattat   3180
gctttatgcc atgtctcttc tagtagaaga taaactttc agttttcaat atgccttata    3240
gtatgaaatt cagaaaacaa ttaaggagg aatagagaga tgctcaaaca gtgtgtaatg    3300
atctgtggaa cgattatata taaatcgtcc aggtagcagc ctctctttat cttagataat   3360
gattagcaga actgcaacat gggaactatg cagaactggt gcatggtaaa taaacaaaag   3420
tttatgaaag aggtaacttc attagaccat gtctcttcta aagatactt tttgcagtta    3480 gtcaataact caatatatct gatataaatt tagataacca tcaaggagga tagagagagc   3540
tcagatcaaa taatgtatga tgatcagtag cattattatt tatgaaaatt tggtataaat   3600
tctccttatc ttgtacaatg tctaaaagaa ctggaccgtg taactatgtg gaactggtgc   3660
atggtaacta caaaaagttc atgatgaacc ataagaaaag gtttggtggg aaattacaaa   3720
aatagtcaga aaggcaacaa ttatgaatcg gaagcaaata aggaggatat agaaatgctc   3780
aaataatgtg taatgattct tagaatgact atacaaaatc tttgataatg tctagcaaaa   3840
ctgcagcatg gtgcatggta actaagaaaa cttatgacaa aatacaagac tgaaatttca   3900
tattgtactg ggtcaagtag gaaattaaaa aagaggttgt aaaagtaaca attagggatt   3960
gaaagcaaga ttgacatgta ctgaatacga aaaccattgg aaggcactaa atcatgcatt   4020
ttattcaagg atcagagctt ttgggcctgt ccacaacctc cagctcaaaa tatcattctt   4080
aacatcacta ttgatgtact ttctttgtga atcatgtgtc tcattctttt cacatctgta   4140
acaaaccatt attactactc aagttagcct caagatagga catttcacct ccttttgtca   4200
atacaatcac atggttttcg agacattagt tgtaccttt ttctagattt aaacctgtca    4260
ctcttcaaga actatgatag tcactggtgt gaattagtaa caaccaagcc agctttataa   4320
ttctaaaatt aagtagctat ccatcccttt cattctcttg gcaaaccaga gatatctttg   4380
actttgtttc acatcttatc ttatgtgtgt gtgagtaaca tgatgcaata tatgtgacat   4440
aggatcattg gttccagatg caagacatgt ttttttaaaa tgattaaatg atgttatgtt   4500
ttgtaatata aaatattata aaactacagt aacacaaaaa aaacttgagt ttctaaactg   4560
ttggtgttct atgatttagt gttcgacata ttatcatttt agtgtgtaat gaccagtttt   4620
gtgtatgttt cttcatacag atcgtctggt tcatgtgaag atattttgcc tggtgggaat   4680
gttgctttgt tgatactttt cagtattgct gtggtcctag cattctggca ctagatggta   4740
cgccgtacgc acatcagtga tgtactttgt ttcttcgtat caaacatttc atgagacaat   4800
cacaaatgtt aagcctgata gaactttcag atttgctgtc atgcttttaa tctccccaat   4860
tttatgatct tacacatcct tgtcagttgc ttagtttctc atcatttacc aatgaagctt   4920
ttctttaata atttgtctgg cgcttgtatg gtatctcaat actaaatggc acaagctttg   4980
```

```
aaatagtatt gctggtagtg gagtagtcag tggctcagtg catgcaattc acacccttcc   5040 gatcttttc ccaaatattt ttttttcttt tctcttttgg agaggacatt gatgcaatcc     5100
atttgtagtg aaactagttg ttacatgcta ctgatgttac actgcagaac caaccaaaat   5160
tatgaagagc cttttaacat tagaaaaccc tcacttataa tttttttaa tcaaacacct     5220 cacctataat ttacaaaaaa atattttgt aagtacctac aaattactt gcatgatcga     5280 gatctttgat ataaacaaaa taaattattg aactgcaagg agtttatata gaccttaaca   5340
tcccggtcag ttcaatgcta ctaataggtt tcctgcattt ctatattaag gcagctgagc   5400
acctggatat tggataggta gataacatga cactgtattt gatttcaagg ctggtgttag   5460
tttgattttt tgtaggtctc gtggagttaa accaaccatt gtattgctca ataatgcatt   5520
ttcacgaaac ccattctctg ttccagaatg gagtccacct tttacatatg gcggaatgtc   5580
tttttgtgtg tacggagggt catatatgtt gattgatggt tcaggcaata ctaccaaaga   5640
ataatcaatt gtgtgaaccg gtatgctagt ttgtgacgaa taatcttaca tttaatcaaa   5700
acaaaagttg gccaggtcat tctcgctagt aacttatcca ccttaggctc ctgcagaatc   5760
agtaacaaat cgtcaaatcc tagaataaca tttgaattaa tggtgctgct gtggtcaagc   5820
ttaggtccat tgttccactg tcgtcttcac taagcatgaa ttacatgtgt agtcctttga   5880
tgtgattgca tactaatcca aaatctcatg tcctcttcca tatgcctcag acatctggaa   5940
gacaaaggtg gctacatatc tcagggccca accttctgg aagacaagat accatgtact    6000
acgttggtaa gaaaaatgtg ccagatctga gaggtgtggg gctctctctc catctttgtc   6060
tccaaatcag atcaccttt gcttttgaca ctgggttatt ctttcagtgc ctataccaag   6120
aaaatctgaa gattctgcgt tgtttacatg taaaacgttc tgaacttgag aaaagtgaaa   6180
agcagtatct agtgtgaaat tttgggtgct gattctttca agatgaaagg agccttagat   6240
agtggaggca tctggaagct gcagcttcca tatctggtaa cttgatgctg cctgcttgcc   6300
taagttgctg tgttaatcct agtattatgt ctgttaaaaa tatgtgttgg gcgacgctac   6360
tctcttttct gatttacatg tggaccaacc atgtggtaat tggagtcgat cagcatctga   6420
aacttgttta gagtaataag ttaattatgc ttttactgt gttctctact ggtatacgaa    6480
agtttgacgg ttcattcaac ctaacaagaa ggaattttcg gttttcaatt agggaagatg   6540
taagtgtaaa ttccacatct agtcgtgtat ggtctgcgcc tatgctcact aaatccaaaa   6600
ggtccatttg cctttttttt ttggattcat g                                  6631
```

<210> SEQ ID NO 22
<211> LENGTH: 2256
<212> TYPE: DNA
<213> ORGANISM: Oryza sativa

<400> SEQUENCE: 22

```
atggcgcacc atgcacagga gtcgggaagg ggcggcgctc aggaggggc ggcgttggga     60 ggcggaggta gaggcgacgg tgcttggggg gcggcacggc ggcggcgctc ggggagggggt   120 ggcacggcgg cagcgcacgg gaggggtggc gcggaggggc ggcgcggcgg cggacagatg   180
acggcgcgac ggcacacggg aggggtgca cgacggcgcg gcggcgcacg ggagggagca     240
ggcggcggcg gcgcacggga ggggcggcgg cggcacacgg gagggggcgg cgtgggtac    300 ccgttgggca tgcccgtgcc cgtcgggcat gggcacgggc atggagtttt gcccgataga    360
gctggcgggc gtgggtcggg cacgggcatg tgggtctcgg gtcgggcatg gaatcgctct    420
```

-continued

| | |
|---|---|
| gcccgtgccc gacccgaccc actgccatcc ctaaggtttg gtagcaccca ttcgctgcct | 480 |
| ttcgccagag atcaattctt ggcgagtgaa gtcgtcgacg gcgagtacat gctctaccat | 540 |
| cttcgccgac gacgtcacct cctcctccgc gaccgccatg tcgtccttcc tttcgtctcc | 600 |
| gtctccgggc gcggtgcgga tggtgacggc gaccccagag gagcacggtc ggaggaagtg | 660 |
| ggggagccgc ggcggccgga gatggaggag gtgaggcgca tacccagtgg ggtagcgcgg | 720 |
| tggccggcgg ccggaagaag aaagaggagg cgtggttgga ggaggaaggg ggagcggcag | 780 |
| ccaccagagg aggggagaag gggggaagag cggcggtcgg agatggagga gagaatgact | 840 |
| ttcacaaaga actgtgaaac ttgtgcttcc aagaacccg cgccgccgca gccgcagccg | 900 |
| ttgccgctgt cctggctgtc gccgaggcgg caatggcggt ggcggagcga ctacggcgac | 960 |
| gccgacgccg ccgaagaaga atcaccggcc ccgctcgtcg aggacggggt atccggtgga | 1020 |
| ggggagaaga agagcttctg gcggcggtg agcctcatcg tcgaacggc ggtggggccg | 1080 |
| gggatgctgg ggctgccgtc cgccaccatc cgctccgggc cggtcccgtc cacggcggcg | 1140 |
| atcgtgctct cgtgggtcta cgtggtgtcc tccatcgtcc tcgtcgcgga gctcagcttc | 1200 |
| gccgcgatgg aggacggcgg cgtcgacgag gtcagcttca cgggacttgc gtcgagcacc | 1260 |
| ttgggggcga cgctcggggc ggtcgtggcc gtcgtctacg ccgccctcag cttctccctg | 1320 |
| ctcgtcgcct cgtcgccgg catcggctcg ctggtgtccc agctcttccc ggcggtggat | 1380 |
| ccggccttgg ccaacgccat cttcccgtgc ttcgccggga cgctcatcgc gttcttcccc | 1440 |
| ttcaaggccg tcgacggcgc caaccgcgcg ctctgcggcc tgatgctcgc ctccatcacc | 1500 |
| gcgcttgttg tcaccggcgt ttccgtcggc cggagcagca tgctgagatc gctcggctac | 1560 |
| gcctgctggc gccctgctac catcctgcct gcaattccgg tgaccgtcct gacgcttggg | 1620 |
| ttccatgtca tcacgccgtt catctgcaag attgtggggg attcagtgta cgatgcgcgg | 1680 |
| cgcgcaatac tgatcggcgg tgccgtccca ttggccatgg tgttgtcctg gaatgccgtc | 1740 |
| attctcgggt tggcaagttc cagtggcggt gcgagattcg atgatccaat taagctgctg | 1800 |
| ctctcggtga atccagcagc attgcctgcc gttcgaggct ttgcgtttgc cgcattggcg | 1860 |
| acgagcttga taggatacgc ggtgagcttt ccgaagcagc tggctgatac agtggagttg | 1920 |
| attgggcaga ggttttctcc gaagcgagga attgggcagc tctctgaatc tagcggtggc | 1980 |
| catgaagaa atggggctat tctcacatgg attgtgctga ttattcctat cgttattgcg | 2040 |
| tcgttcttct cagcggcctt ctccaaggca ctggattttg ctggggttta tgcaaactgc | 2100 |
| ttccttttg ggatcctccc tcctgtcatg gcctggattc accggtcaca gaagagaaag | 2160 |
| agatcgtctg gttcatgtga agatattttg cctggtggga atgttgcttt gttgatactt | 2220 |
| ttcagtattg ctgtggtcct agcattctgg cactag | 2256 |

<210> SEQ ID NO 23
<211> LENGTH: 751
<212> TYPE: PRT
<213> ORGANISM: Oryza sativa

<400> SEQUENCE: 23

Met Ala His His Ala Gln Glu Ser Gly Arg Gly Gly Ala Gln Glu Gly
1               5                   10                  15

Ala Ala Leu Gly Gly Gly Gly Arg Gly Asp Gly Ala Trp Gly Ala Ala
            20                  25                  30

Arg Arg Arg Arg Ser Gly Gly Gly Gly Thr Ala Ala Ala His Gly Arg
        35                  40                  45

Gly Gly Ala Glu Gly Arg Arg Gly Gly Gln Met Thr Ala Arg Arg
50                  55                  60

His Thr Gly Gly Val Ala Arg Arg Gly Gly Ala Arg Glu Gly Ala
65                  70                  75                  80

Gly Gly Gly Gly Ala Arg Glu Gly Arg Arg His Thr Gly Gly Ala
            85                  90                  95

Ala Arg Gly Tyr Pro Leu Gly Met Pro Val Pro Val Gly His Gly His
            100                 105                 110

Gly His Gly Val Leu Pro Asp Arg Ala Gly Gly Arg Gly Ser Gly Thr
            115                 120                 125

Gly Met Trp Val Ser Gly Arg Ala Trp Asn Arg Ser Ala Arg Ala Arg
130                 135                 140

Pro Asp Pro Leu Pro Ser Leu Arg Phe Gly Ser Thr His Ser Leu Pro
145                 150                 155                 160

Phe Ala Arg Asp Gln Phe Leu Ala Ser Glu Val Val Asp Gly Glu Tyr
                165                 170                 175

Met Leu Tyr His Leu Arg Arg Arg His Leu Leu Leu Arg Asp Arg
            180                 185                 190

His Val Val Leu Pro Phe Val Ser Val Ser Gly Arg Gly Ala Asp Gly
            195                 200                 205

Asp Gly Asp Pro Arg Gly Ala Arg Ser Glu Glu Val Gly Glu Pro Arg
210                 215                 220

Arg Pro Glu Met Glu Glu Val Arg Arg Ile Pro Ser Gly Val Ala Arg
225                 230                 235                 240

Trp Pro Ala Ala Gly Arg Arg Lys Arg Arg Gly Trp Arg Arg Lys
                245                 250                 255

Gly Glu Arg Gln Pro Pro Glu Glu Gly Arg Arg Gly Glu Glu Arg Arg
            260                 265                 270

Ser Glu Met Glu Glu Arg Met Thr Phe Thr Lys Asn Cys Glu Thr Cys
            275                 280                 285

Ala Ser Lys Asn Pro Ala Pro Pro Gln Pro Gln Pro Leu Pro Leu Ser
            290                 295                 300

Trp Leu Ser Pro Arg Arg Gln Trp Arg Trp Arg Ser Asp Tyr Gly Asp
305                 310                 315                 320

Ala Asp Ala Ala Glu Glu Ser Pro Ala Pro Leu Val Glu Asp Gly
                325                 330                 335

Val Ser Gly Gly Gly Glu Lys Lys Ser Phe Trp Ala Ala Val Ser Leu
            340                 345                 350

Ile Val Gly Thr Ala Val Gly Pro Gly Met Leu Gly Leu Pro Ser Ala
            355                 360                 365

Thr Ile Arg Ser Gly Pro Val Pro Ser Thr Ala Ala Ile Val Leu Ser
370                 375                 380

Trp Val Tyr Val Val Ser Ser Ile Val Leu Val Ala Glu Leu Ser Phe
385                 390                 395                 400

Ala Ala Met Glu Asp Gly Gly Val Asp Glu Val Ser Phe Thr Gly Leu
                405                 410                 415

Ala Ser Ser Thr Leu Gly Ala Thr Leu Gly Ala Val Val Ala Val Val
            420                 425                 430

Tyr Ala Ala Leu Ser Phe Ser Leu Val Ala Cys Val Ala Gly Ile
            435                 440                 445

Gly Ser Leu Val Ser Gln Leu Phe Pro Ala Val Asp Pro Ala Leu Ala
450                 455                 460

Asn Ala Ile Phe Pro Cys Phe Ala Gly Thr Leu Ile Ala Phe Phe Pro

```
               465                 470                 475                 480
           Phe Lys Ala Val Asp Gly Ala Asn Arg Ala Leu Cys Gly Leu Met Leu
                           485                 490                 495

Ala Ser Ile Thr Ala Leu Val Val Thr Gly Val Ser Val Gly Arg Ser
                           500                 505                 510

Ser Met Leu Arg Ser Leu Gly Tyr Ala Cys Trp Arg Pro Ala Thr Ile
                           515                 520                 525

Leu Pro Ala Ile Pro Val Thr Val Leu Thr Leu Gly Phe His Val Ile
                           530                 535                 540

Thr Pro Phe Ile Cys Lys Ile Val Gly Asp Ser Val Tyr Asp Ala Arg
           545                 550                 555                 560

Arg Ala Ile Leu Ile Gly Gly Ala Val Pro Leu Ala Met Val Leu Ser
                           565                 570                 575

Trp Asn Ala Val Ile Leu Gly Leu Ala Ser Ser Gly Gly Ala Arg
                           580                 585                 590

Phe Asp Asp Pro Ile Lys Leu Leu Leu Ser Val Asn Pro Ala Ala Leu
                           595                 600                 605

Pro Ala Val Arg Gly Phe Ala Phe Ala Ala Leu Ala Thr Ser Leu Ile
                           610                 615                 620

Gly Tyr Ala Val Ser Phe Pro Lys Gln Leu Ala Asp Thr Val Glu Leu
           625                 630                 635                 640

Ile Gly Gln Arg Phe Ser Pro Lys Arg Gly Ile Gly Gln Leu Ser Glu
                           645                 650                 655

Ser Ser Gly Gly His Gly Arg Asn Gly Ala Ile Leu Thr Trp Ile Val
                           660                 665                 670

Leu Ile Ile Pro Ile Val Ile Ala Ser Phe Phe Ser Ala Ala Phe Ser
                           675                 680                 685

Lys Ala Leu Asp Phe Ala Gly Val Tyr Ala Asn Cys Phe Leu Phe Gly
                           690                 695                 700

Ile Leu Pro Pro Val Met Ala Trp Ile His Arg Ser Gln Lys Arg Lys
           705                 710                 715                 720

Arg Ser Ser Gly Ser Cys Glu Asp Ile Leu Pro Gly Gly Asn Val Ala
                           725                 730                 735

Leu Leu Ile Leu Phe Ser Ile Ala Val Val Leu Ala Phe Trp His
                           740                 745                 750

<210> SEQ ID NO 24
<211> LENGTH: 23
<212> TYPE: DNA
<213> ORGANISM: Artificial Sequence
<220> FEATURE:
<223> OTHER INFORMATION: Forward primer for cloning gDNA of OsDN-LTP4
      gene

<400> SEQUENCE: 24
atggagttcg ggaggcctgc ttg                                         23

<210> SEQ ID NO 25
<211> LENGTH: 29
<212> TYPE: DNA
<213> ORGANISM: Artificial Sequence
<220> FEATURE:
<223> OTHER INFORMATION: Reverse primer for cloning gDNA of OsDN-LTP4
      gene

<400> SEQUENCE: 25
tcacctatac tggtcaacag tgaatctcc                                   29
```

<210> SEQ ID NO 26
<211> LENGTH: 27
<212> TYPE: DNA
<213> ORGANISM: Artificial Sequence
<220> FEATURE:
<223> OTHER INFORMATION: Forward primer for cloning gDNA of OsDN-LTP6
      gene

<400> SEQUENCE: 26
gatccaacag acaactctaa cactagg                                           27

<210> SEQ ID NO 27
<211> LENGTH: 27
<212> TYPE: DNA
<213> ORGANISM: Artificial Sequence
<220> FEATURE:
<223> OTHER INFORMATION: Reverse primer for cloning gDNA of OsDN-LTP6
      gene

<400> SEQUENCE: 27
gatccaacag acaactctaa cactagg                                           27

<210> SEQ ID NO 28
<211> LENGTH: 25
<212> TYPE: DNA
<213> ORGANISM: Artificial Sequence
<220> FEATURE:
<223> OTHER INFORMATION: Forward primer for cloning cDNA of OsDN-LTP7
      gene

<400> SEQUENCE: 28
gcttggcttc gacgacctta tcatc                                             25

<210> SEQ ID NO 29
<211> LENGTH: 30
<212> TYPE: DNA
<213> ORGANISM: Artificial Sequence
<220> FEATURE:
<223> OTHER INFORMATION: Reverse primer for cloning cDNA of OsDN-LTP7
      gene

<400> SEQUENCE: 29
tcctcacaaa atcatgacaa gataaactga                                        30

<210> SEQ ID NO 30
<211> LENGTH: 20
<212> TYPE: DNA
<213> ORGANISM: Artificial Sequence
<220> FEATURE:
<223> OTHER INFORMATION: Forward primer for cloning cDNA of OsBAK1L gene

<400> SEQUENCE: 30
gcacgaggca ccaccgcagc                                                   20

<210> SEQ ID NO 31
<211> LENGTH: 27
<212> TYPE: DNA
<213> ORGANISM: Artificial Sequence
<220> FEATURE:
<223> OTHER INFORMATION: Reverse primer for cloning cDNA of OsBAK1L gene

<400> SEQUENCE: 31
ccgccgccgt cctcttcttt ttattcg                                           27

<210> SEQ ID NO 32
<211> LENGTH: 28

```
<212> TYPE: DNA
<213> ORGANISM: Artificial Sequence
<220> FEATURE:
<223> OTHER INFORMATION: Forward primer for cloning cDNA of OsEIL2 gene

<400> SEQUENCE: 32
aattcgtttc agtagaacca gttggatc                                        28

<210> SEQ ID NO 33
<211> LENGTH: 20
<212> TYPE: DNA
<213> ORGANISM: Artificial Sequence
<220> FEATURE:
<223> OTHER INFORMATION: Reverse primer for cloning cDNA of OsEIL2 gene

<400> SEQUENCE: 33
ccgccatcgc caagtaccag                                                 20

<210> SEQ ID NO 34
<211> LENGTH: 29
<212> TYPE: DNA
<213> ORGANISM: Artificial Sequence
<220> FEATURE:
<223> OTHER INFORMATION: Forward primer for cloning cDNA of OsPPO3 gene

<400> SEQUENCE: 34
ggccagtaat cacatacaca gtttgacac                                       29

<210> SEQ ID NO 35
<211> LENGTH: 26
<212> TYPE: DNA
<213> ORGANISM: Artificial Sequence
<220> FEATURE:
<223> OTHER INFORMATION: Reverse primer for cloning cDNA of OsPPO3 gene

<400> SEQUENCE: 35
ccaccgtctt tctcggagaa cgcttc                                          26

<210> SEQ ID NO 36
<211> LENGTH: 27
<212> TYPE: DNA
<213> ORGANISM: Artificial Sequence
<220> FEATURE:
<223> OTHER INFORMATION: Forward primer for cloning gDNA of OsTTP1 gene

<400> SEQUENCE: 36
atgcccgacc cgaaaatgtg cctgtag                                         27

<210> SEQ ID NO 37
<211> LENGTH: 28
<212> TYPE: DNA
<213> ORGANISM: Artificial Sequence
<220> FEATURE:
<223> OTHER INFORMATION: Reverse primer for cloning gDNA of OsTTP1 gene

<400> SEQUENCE: 37
catgaatcca aaaaaaaaag gcaaatgg                                        28

<210> SEQ ID NO 38
<211> LENGTH: 20
<212> TYPE: DNA
<213> ORGANISM: Artificial Sequence
<220> FEATURE:
<223> OTHER INFORMATION: Forward primer for real-time RT-PCR analysis of
      OsDN-LTP4 gene

<400> SEQUENCE: 38
```
gatgtgccat atctttgttc                                               20

<210> SEQ ID NO 39
<211> LENGTH: 19
<212> TYPE: DNA
<213> ORGANISM: Artificial Sequence
<220> FEATURE:
<223> OTHER INFORMATION: Reverse primer for real-time RT-PCR analysis of
      OsDN-LTP4 gene

<400> SEQUENCE: 39
gaggaaatga actgctctc                                                19

<210> SEQ ID NO 40
<211> LENGTH: 17
<212> TYPE: DNA
<213> ORGANISM: Artificial Sequence
<220> FEATURE:
<223> OTHER INFORMATION: Forward primer for real-time RT-PCR analysis of
      OsDN-LTP6 gene

<400> SEQUENCE: 40
cttctccgtc ctcctcg                                                  17

<210> SEQ ID NO 41
<211> LENGTH: 17
<212> TYPE: DNA
<213> ORGANISM: Artificial Sequence
<220> FEATURE:
<223> OTHER INFORMATION: Reverse primer for real-time RT-PCR analysis of
      OsDN-LTP6 gene

<400> SEQUENCE: 41
gtgtgccctc catgtcc                                                  17

<210> SEQ ID NO 42
<211> LENGTH: 23
<212> TYPE: DNA
<213> ORGANISM: Artificial Sequence
<220> FEATURE:
<223> OTHER INFORMATION: Forward primer for real-time RT-PCR analysis of
      OsDN-LTP7 gene

<400> SEQUENCE: 42
gaccagagct cgtaccctaa ccc                                           23

<210> SEQ ID NO 43
<211> LENGTH: 22
<212> TYPE: DNA
<213> ORGANISM: Artificial Sequence
<220> FEATURE:
<223> OTHER INFORMATION: Reverse primer for real-time RT-PCR analysis of
      OsDN-LTP7 gene

<400> SEQUENCE: 43
ggaggcaagc aaggaggtta tc                                            22

<210> SEQ ID NO 44
<211> LENGTH: 20
<212> TYPE: DNA
<213> ORGANISM: Artificial Sequence
<220> FEATURE:
<223> OTHER INFORMATION: Forward primer for real-time RT-PCR analysis of
      OsBAK1L gene

<400> SEQUENCE: 44
ccttttaact gggccaatcc                                              20

<210> SEQ ID NO 45
<211> LENGTH: 19
<212> TYPE: DNA
<213> ORGANISM: Artificial Sequence
<220> FEATURE:
<223> OTHER INFORMATION: Reverse primer for real-time RT-PCR analysis of
      OsBAK1L gene

<400> SEQUENCE: 45
ggagggaagt gatcgaacg                                               19

<210> SEQ ID NO 46
<211> LENGTH: 19
<212> TYPE: DNA
<213> ORGANISM: Artificial Sequence
<220> FEATURE:
<223> OTHER INFORMATION: Forward primer for real-time RT-PCR analysis of
      OsEIL2 gene

<400> SEQUENCE: 46
gcacatcttc gagccactc                                               19

<210> SEQ ID NO 47
<211> LENGTH: 20
<212> TYPE: DNA
<213> ORGANISM: Artificial Sequence
<220> FEATURE:
<223> OTHER INFORMATION: Reverse primer for real-time RT-PCR analysis of
      OsEIL2 gene

<400> SEQUENCE: 47
tcgcggatga agaaattagc                                              20

<210> SEQ ID NO 48
<211> LENGTH: 20
<212> TYPE: DNA
<213> ORGANISM: Artificial Sequence
<220> FEATURE:
<223> OTHER INFORMATION: Forward primer for real-time RT-PCR analysis of
      OsPPO3 gene

<400> SEQUENCE: 48
catgggcatg ttctactcgg                                              20

<210> SEQ ID NO 49
<211> LENGTH: 18
<212> TYPE: DNA
<213> ORGANISM: Artificial Sequence
<220> FEATURE:
<223> OTHER INFORMATION: Reverse primer for real-time RT-PCR analysis of
      OsPPO3 gene

<400> SEQUENCE: 49
gtcggtgaag tcggtgtc                                                18

<210> SEQ ID NO 50
<211> LENGTH: 22
<212> TYPE: DNA
<213> ORGANISM: Artificial Sequence
<220> FEATURE:
<223> OTHER INFORMATION: Forward primer for real-time RT-PCR analysis of
      OsTTP1 gene

<400> SEQUENCE: 50
catggattgt gctgattatt cc                                           22

```
<210> SEQ ID NO 51
<211> LENGTH: 21
<212> TYPE: DNA
<213> ORGANISM: Artificial Sequence
<220> FEATURE:
<223> OTHER INFORMATION: Reverse primer for real-time RT-PCR analysis of
      OsTTP1 gene

<400> SEQUENCE: 51
ctcttctgtg accggtgaat c                                              21
```

PLANTS HAVING ALTERED AGRONOMIC CHARACTERISTICS UNDER ABIOTIC STRESS CONDITIONS AND RELATED CONSTRUCTS AND METHODS INVOLVING ABIOTIC STRESS TOLERANCE GENES

FIELD

The field relates to plant breeding and genetics and, in particular, relates to recombinant DNA constructs useful in plants for conferring nitrogen use efficiency, tolerance to nitrogen limiting conditions and/or drought and/or tolerance.

BACKGROUND

Abiotic stresses such as drought, high salinity and deficiency of nutrient elements adversely affect the growth and productivity of plants including crops, which significantly limit crop production worldwide. Cumulatively, these factors are estimated to be responsible for an average 70% reduction in agricultural production. Plants are sessile and have to adjust to the prevailing environmental conditions of their surroundings. This has led to their development of a great plasticity in gene regulation, morphogenesis, and metabolism. Adaptation and defense strategies involve the activation of genes encoding proteins important in the acclimation or defense towards the different stressors.

Drought (insufficient available water) is one of the major abiotic stresses that limit crop productivity worldwide, and exposure of plants to a water-limiting environment during various developmental stages appears to activate various physiological and developmental changes. Although many reviews on molecular mechanisms of abiotic stress responses and genetic regulatory networks of drought stress tolerance have been published (Valliyodan, B., and Nguyen, H. T. (2006) Curr. Opin. Plant Biol. 9:189-195; Wang, W., et al. (2003) Planta 218:1-14; Vinocur, B., and Altman, A. (2005) Curr. Opin. Biotechnol. 16:123-132; Chaves, M. M., and Oliveira, M. M. (2004) J. Exp. Bot. 55:2365-2384; Shinozaki, K., et al. (2003) Curr. Opin. Plant Biol. 6:410-417; Yamaguchi-Shinozaki, K., and Shinozaki, K. (2005) Trends Plant Sci. 10:88-94), it remains a major challenge in biology to understand the basic biochemical and molecular mechanisms for drought stress perception, signal transduction and tolerance. Genetic research has shown that drought tolerance is a quantitative trait, controlled by many genes. Molecular marker-assisted breeding has led to improved drought tolerance in crops. However, marker accuracy and breeding efficiency remain problematic (Ashraf M. (2010) Biotechnol. Adv. 28:169-183). Transgenic approaches to engineering drought tolerance in crops have made progress (Vinocur B. and Altman A. (2005) Curr. Opin. Biotechnol. 16:123-132; Lawlor D W. (2013) J. Exp. Bot. 64:83-108).

The absorption of nitrogen by plants plays an important role in their growth (Gallais et al., J. Exp. Bot. 55(396):295-306 (2004)). Plants synthesize amino acids from inorganic nitrogen in the environment. Consequently, nitrogen fertilization has been a powerful tool for increasing the yield of cultivated plants, such as rice, maize and soybean. Lack of sufficient plant-available nitrogen for optimum growth and development may be considered as an abiotic stress. In order to avoid pollution by nitrates and to maintain a sufficient profit margin, today farmers desire to reduce the use of nitrogen fertilizer. If a plant variety has increased nitrogen assimilation capacity, it would also be expected to have increased growth and yield. In summary, plant varieties that have better nitrogen use efficiency (NUE) are desirable.

Activation tagging can be utilized to identify genes with the ability to affect a trait. This approach has been used in the model plant species Arabidopsis thaliana (Weigel et al., Plant Physiol. 122:1003-1013 (2000)). Insertions of transcriptional enhancer elements can dominantly activate and/or elevate the expression of nearby endogenous genes. This method can be used to identify genes of interest for a particular trait (e.g. nitrogen use efficiency in a plant), that when placed in an organism as a transgene, can alter that trait.

SUMMARY

The following embodiments are among those encompassed by the disclosure:

One embodiment, includes an isolated polynucleotide, comprising: (a) a polynucleotide with nucleotide sequence of at least 85% sequence identity to SEQ ID NO: 3, 6, 9, 12, 15, 18 or 21; (b) a polynucleotide with nucleotide sequence of at least 85% sequence identity to SEQ ID NO: 4, 7, 10, 13, 16, 19 or 22; (c) a polynucleotide encoding a polypeptide with amino acid sequence of at least 90% sequence identity to SEQ ID NO: 5, 8, 11, 14, 17, 20 or 23; or (d) the full complement of the nucleotide sequence of (a), (b) or (c), wherein over-expression of the polynucleotide in a plant enhances nitrogen stress tolerance. The nucleotide sequence comprises SEQ ID NO: 3, SEQ ID NO: 4, SEQ ID NO: 6, SEQ ID NO: 7, SEQ ID NO: 9, SEQ ID NO: 10, SEQ ID NO: 12, SEQ ID NO: 13, SEQ ID NO: 15, SEQ ID NO: 16, SEQ ID NO: 18, SEQ ID NO: 19, SEQ ID NO: 21 or SEQ ID NO: 22. The amino acid sequence of the polypeptide comprises SEQ ID NO: 5, SEQ ID NO: 8, SEQ ID NO: 11, SEQ ID NO: 14, SEQ ID NO: 17, SEQ ID NO: 20 or SEQ ID NO: 23.

Another embodiment, includes a recombinant DNA construct comprising the isolated polynucleotide operably linked to at least one regulatory sequence, wherein the polynucleotide comprises (a) a polynucleotide with nucleotide sequence of at least 85% sequence identity to S SEQ ID NO: 3, 4, 6, 7, 9, 10, 12, 13, 15, 16, 18, 19, 21 or 22; (b) a polynucleotide encoding a polypeptide with amino acid sequence of at least 90% sequence identity to SEQ ID NO: 5, 8, 11, 14, 17, 20 or 23; or (c) the full complement of the nucleotide sequence of (a) or (b); the at least one regulatory sequence is a promoter functional in a plant.

A third embodiment, includes a plant or seed comprising a recombinant DNA construct comprising the polynucleotide operably linked to at least one regulatory sequence, wherein the polynucleotide comprises (a) a polynucleotide with nucleotide sequence of at least 85% sequence identity to SEQ ID NO: 3, 4, 6, 7, 9, 10, 12, 13, 15, 16, 18, 19, 21 or 22; (b) a polynucleotide encoding a polypeptide with amino acid sequence of at least 90% sequence identity to SEQ ID NO: 5, 8, 11, 14, 17, 20 or 23; or (c) the full complement of the nucleotide sequence of (a) or (b); the at least one regulatory sequence is a promoter functional in a plant.

Another embodiment, includes a plant comprising in its genome a recombinant DNA construct comprising a polynucleotide operably linked to at least one regulatory element, wherein the polynucleotide comprises (a) a polynucleotide with nucleotide sequence of at least 85% sequence identity to SEQ ID NO: 3, 4, 6, 7, 9, 10, 12, 13, 15, 16, 18, 19, 21 or 22; (b) a polynucleotide encoding a polypeptide with amino acid sequence of at least 90% sequence identity to SEQ ID NO: 5, 8, 11, 14, 17, 20 or 23; or (c) the full complement of the nucleotide sequence of (a) or (b); the said plant exhibits improved nitrogen use efficiency (NUE) when compared to a control plant.

Another embodiment, includes an isolated polynucleotide, comprising: (a) a polynucleotide with nucleotide sequence of at least 85% sequence identity to SEQ ID NO: 15; (b) a polynucleotide with nucleotide sequence of at least 85% sequence identity to SEQ ID NO: 16; (c) a polynucleotide encoding a polypeptide with amino acid sequence of at least 90% sequence identity to SEQ ID NO: 17; or (d) the full complement of the nucleotide sequence of (a), (b) or (c), wherein over-expression of the polynucleotide in a plant enhances drought and cold tolerance. The nucleotide sequence comprises SEQ ID NO: 15 or SEQ ID NO: 16. The amino acid sequence of the polypeptide comprises SEQ ID NO: 17.

Another embodiment, includes a plant comprising in its genome a recombinant DNA construct comprising a polynucleotide operably linked to at least one regulatory element, wherein the polynucleotide comprises (a) a polynucleotide with nucleotide sequence of at least 85% sequence identity to SEQ ID NO: 15 or 16; (b) a polynucleotide encoding a polypeptide with amino acid sequence of at least 90% sequence identity to SEQ ID NO: 17; or (c) the full complement of the nucleotide sequence of (a) or (b); the said plant exhibits improved drought and cold tolerance when compared to a control plant.

A further embodiment, includes any of the plants of the disclosure, wherein the plant is selected from the group consisting of rice, maize, soybean, sunflower, sorghum, canola, wheat, alfalfa, cotton, barley, millet, sugar cane and switchgrass.

In another embodiment, a method of increasing nitrogen stress tolerance or NUE in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity when compared to SEQ ID NO: 5, 8, 11, 14, 17, 20 or 23; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased nitrogen stress tolerance or NUE when compared to a control plant not comprising the recombinant DNA construct.

In another embodiment, a method of evaluating nitrogen stress tolerance or NUE in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity when compared to SEQ ID NO: 5, 8, 11, 14, 17, 20 or 23; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for nitrogen stress tolerance or NUE compared to a control plant not comprising the recombinant DNA construct.

In another embodiment, a method of increasing drought and cold tolerance in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity when compared to SEQ ID NO: 17; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased drought and cold tolerance when compared to a control plant not comprising the recombinant DNA construct.

In another embodiment, a method of evaluating drought and cold tolerance in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity when compared to SEQ ID NO: 17; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for drought and cold tolerance compared to a control plant not comprising the recombinant DNA construct.

In another embodiment, a method of determining an alteration of an agronomic characteristic in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity when compared to SEQ ID NO: 5, 8, 11, 14, 17, 20 or 23; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) determining whether the progeny plant exhibits an alteration of at least one agronomic characteristic when compared to a control plant not comprising the recombinant DNA construct, wherein said determining step (d) comprises determining whether the transgenic plant exhibits an alteration of at least one agronomic characteristic when compared, under nitrogen limiting conditions and/or water limiting conditions, to a control plant not comprising the recombinant DNA construct.

In another embodiment, the present disclosure concerns a recombinant DNA construct comprising any of the isolated polynucleotides of the present disclosure operably linked to at least one regulatory sequence, and a cell, a plant, and a seed comprising the recombinant DNA construct. The cell may be eukaryotic, e.g., a yeast, insect or plant cell, or prokaryotic, e.g., a bacterium.

BRIEF DESCRIPTION OF THE FIGURES AND TABLES

The disclosure can be more fully understood from the following detailed description and the accompanying drawings and tables which form a part of this application.

FIG. 1 provides relative expression levels by real-time PCR analyses of OsDN-LTP4 gene in leaves of separate over-expressed transgenic rice lines. The base level of expression in DP0036.05 was set at 1.00, and the expression levels in other OsDN-LTP4 lines were shown as fold-increases compared to DP0036.05. ZH11 is wild type rice Zhonghua11.

FIG. 2 shows the relative expression levels of OsDN-LTP6 gene in leaves of different transgenic rice lines by real-time PCR analyses. The base expression level in DP0046.20 is set at 1.00, the numbers on the top of the columns are fold-changes compared to DP0046.20 rice.

FIG. 3 shows the relative expression levels of OsDN-LTP7 gene in leaves of different transgenic rice lines by real-time PCR analyses. The base expression level in DP0005 is set at 1.00, the numbers on the top of the columns are fold-changes compared to DP0005 rice. DP0005 is rice plants transformed with empty vector DP0005.

FIG. 4 shows the relative expression levels of OsBAK1L gene in leaves of different transgenic rice lines by real-time PCR analyses. The base expression level in ZH11-TC is set at 1.00, the numbers on the top of the columns are fold-changes compared to ZH11-TC rice. ZH11-TC is tissue cultured ZH11rice, and DP0158 is rice plants transformed with empty vector DP0158.

Figure 1:
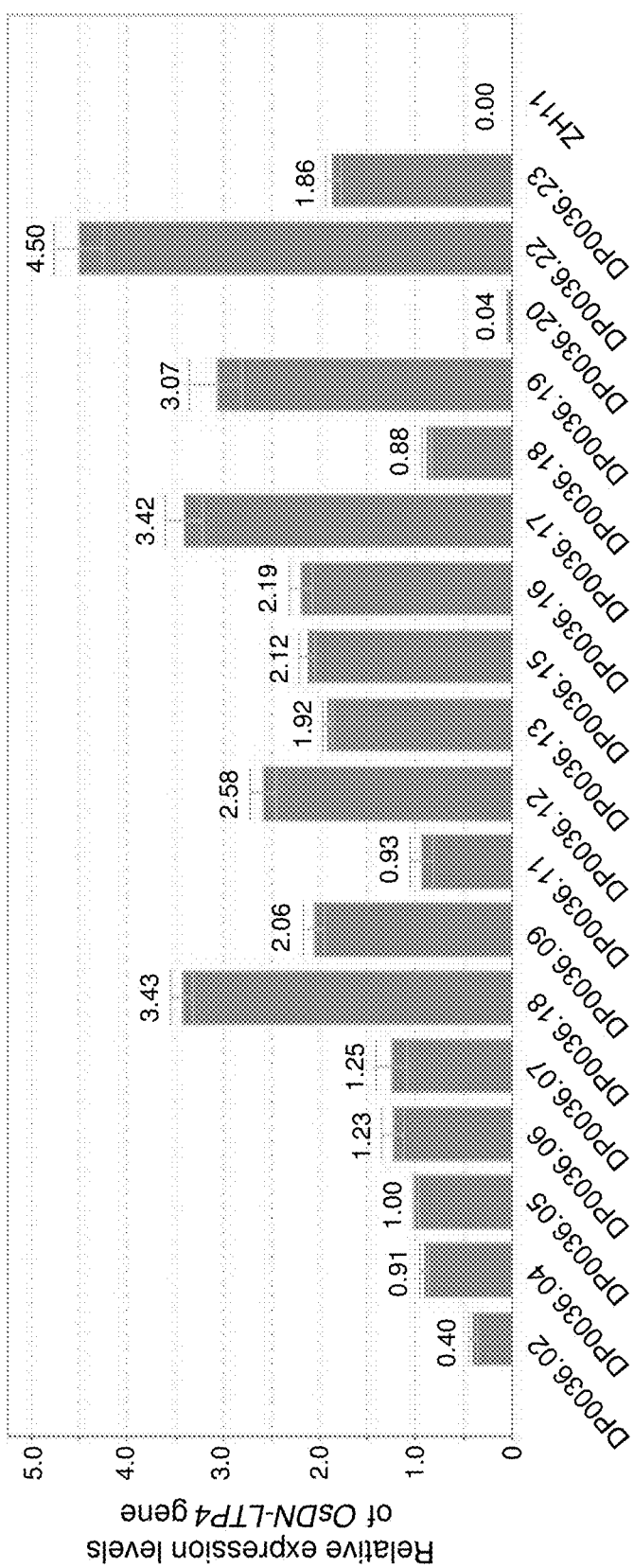

Table 1. SEQ ID NOs for nucleotide and amino acid sequences provided in the sequence listing Table 2. Rice gene names, Gene IDs (from TIGR) and Construct IDs Table 3. Primers for cloning rice abiotic stress tolerance genes Table 4. PCR reaction mixture for cloning abiotic stress tolerance genes Table 5. PCR cycle conditions for abiotic stress tolerance genes Table 6. Modified Hoagland's nutrient solution for culturing rice Table 7. Low nitrogen tolerance assay of OsDN-LTP4 transgenic rice plants under greenhouse low nitrogen conditions ($1^{st}$ experiment)

Table 8. Low nitrogen tolerance assay of OsDN-LTP4 transgenic rice plants under greenhouse low nitrogen conditions ($2^{nd}$ experiment, ZH11-TC as control)

Table 9. Low nitrogen tolerance assay of OsDN-LTP4 transgenic rice plants under greenhouse low nitrogen conditions ($2^{nd}$ experiment, DP0158 as control)

Table 10. Low nitrogen tolerance assay of OsDN-LTP4 transgenic rice plants under greenhouse low nitrogen conditions ($3^{rd}$ experiment, ZH11-TC as control)

Table 11. Low nitrogen tolerance assay of OsDN-LTP4 transgenic rice plants under greenhouse low nitrogen conditions ($3^{rd}$ experiment, DP0158 as control)

Table 12. Low nitrogen tolerance assay of OsDN-LTP6 transgenic rice plants under greenhouse low nitrogen conditions ($1^{st}$ experiment)

Table 13. Low nitrogen tolerance assay of OsDN-LTP6 transgenic rice plants under greenhouse low nitrogen conditions ($2^{nd}$ experiment)

Table 14. Low nitrogen tolerance assay of OsDN-LTP6 transgenic rice plants under greenhouse low nitrogen conditions ($3^{rd}$ experiment, ZH11-TC as control)

Table 15. Low nitrogen tolerance assay of OsDN-LTP6 transgenic rice plants under greenhouse low nitrogen conditions ($3^{rd}$ experiment, DP0158 as control)

Table 16. Low nitrogen tolerance assay of OsDN-LTP7 transgenic rice plants under greenhouse low nitrogen conditions ($1^{st}$ experiment)

Table 17. Low nitrogen tolerance assay of OsDN-LTP7 transgenic rice plants under greenhouse low nitrogen conditions ($2^{nd}$ experiment)

Table 18. Low nitrogen tolerance assay of OsDN-LTP7 transgenic rice plants under greenhouse low nitrogen conditions ($3^{rd}$ experiment, ZH11-TC as control)

Table 19. Low nitrogen tolerance assay of OsDN-LTP7 transgenic rice plants under greenhouse low nitrogen conditions ($4^{th}$ experiment, ZH11-TC as control)

Table 20. Low nitrogen tolerance assay of OsBAK1L transgenic rice plants under greenhouse low nitrogen conditions ($1^{st}$ experiment)

Table 21. Low nitrogen tolerance assay of OsBAK1L transgenic rice plants under greenhouse low nitrogen conditions ($2^{nd}$ experiment)

Table 22. Low nitrogen tolerance assay of OsBAK1L transgenic rice plants under greenhouse low nitrogen conditions ($3^{rd}$ experiment, ZH11-TC as control)

Table 23. Low nitrogen tolerance assay of OsBAK1L transgenic rice plants under greenhouse low nitrogen conditions ($4^{th}$ experiment, ZH11-TC as control)

Table 24. Low nitrogen tolerance assay of OsEIL2 transgenic rice plants under greenhouse low nitrogen conditions ($1^{st}$ experiment, ZH11-TC as control)

Table 25. Low nitrogen tolerance assay of OsEIL2 transgenic rice plants under greenhouse low nitrogen conditions ($1^{st}$ experiment, DP0158 as control)

Table 26. Low nitrogen tolerance assay of OsEIL2 transgenic rice plants under greenhouse low nitrogen conditions ($2^{nd}$ experiment, ZH11-TC as control)

Table 27. Low nitrogen tolerance assay of OsEIL2 transgenic rice plants under greenhouse low nitrogen conditions ($2^{nd}$ experiment, DP0158 as control)

Table 28. Low nitrogen tolerance assay of OsPPO3 transgenic rice plants under greenhouse low nitrogen conditions Table 29. Low nitrogen tolerance assay of OsPPO3 transgenic rice plants under greenhouse low nitrogen conditions ($2^{nd}$ experiment, ZH11-TC as control)

Table 30. Low nitrogen tolerance assay of OsPPO3 transgenic rice plants under greenhouse low nitrogen conditions ($2^{nd}$ experiment, DP0158 as control)

Table 31. Low nitrogen tolerance assay of OsPPO3 transgenic rice plants under greenhouse low nitrogen conditions ($3^{rd}$ experiment, ZH11-TC as control)

Table 32. Low nitrogen tolerance assay of OsPPO3 transgenic rice plants under greenhouse low nitrogen conditions ($3^{rd}$ experiment, DP0158 as control)

Table 33. Low nitrogen tolerance assay of OsTTP1 transgenic rice plants under greenhouse low nitrogen conditions ($1^{st}$ experiment)

Table 34. Low nitrogen tolerance assay of OsTTP1 transgenic rice plants under greenhouse low nitrogen conditions ($2^{nd}$ experiment, ZH11-TC as control)

Table 35. Low nitrogen tolerance assay of OsTTP1 transgenic rice plants under greenhouse low nitrogen conditions (2$^{nd}$ experiment, DP0158 as control)

Table 36. Chlorate sensitive assay of OsDN-LTP6 transgenic rice seedlings at transgenic line level (1$^{st}$ experiment)

Table 37. Chlorate sensitive assay of OsDN-LTP6 transgenic rice seedlings at transgenic line level (2$^{nd}$ experiment)

Table 38. Chlorate sensitive assay of OsBAK1L transgenic rice seedlings at transgenic line level (1$^{st}$ experiment)

Table 39. Chlorate sensitive assay of OsBAK1L transgenic rice seedlings at transgenic line level (2$^{nd}$ experiment)

Table 40. Chlorate sensitive assay of OsEIL2 transgenic rice seedlings at transgenic line level (1$^{st}$ experiment)

Table 41. Chlorate sensitive assay of OsEIL2 transgenic rice seedlings at transgenic line level (2$^{nd}$ experiment)

Table 42. Chlorate sensitive assay of OsPPO3 transgenic rice seedlings at transgenic line level (1$^{st}$ experiment)

Table 43. Chlorate sensitive assay of OsPPO3 transgenic rice seedlings at transgenic line level (2$^{nd}$ experiment)

Table 44. Grain yield analysis of OsDN-LTP4 transgenic rice under field low nitrogen condition Table 45. Grain yield analysis of OsDN-LTP4 transgenic rice under field normal nitrogen condition Table 46. Biomass analysis of OsDN-LTP4 transgenic rice under field low nitrogen condition Table 47. Plant height analysis of OsDN-LTP4 transgenic rice under field low nitrogen condition Table 48. Plant height analysis of OsDN-LTP4 transgenic rice under field normal nitrogen condition Table 49. The effective panicle number analysis of OsDN-LTP4 transgenic rice under field low nitrogen condition Table 50. The effective panicle number analysis of OsDN-LTP4 transgenic rice under field normal nitrogen condition Table 51. Grain yield analysis of OsDN-LTP7 transgenic rice under field low nitrogen condition Table 52. Grain yield analysis of OsDN-LTP7 transgenic rice under field normal nitrogen condition Table 53. Flag leaf SPAD value analysis of OsDN-LTP7 transgenic rice under field low nitrogen condition Table 54. Top second leaf SPAD value analysis of OsDN-LTP7 transgenic rice under field low nitrogen condition Table 55. Grain yield analysis of OsBAK1L transgenic rice under field low nitrogen condition Table 56. Grain yield analysis of OsBAK1L transgenic rice under field normal nitrogen condition Table 57. The effective panicle number analysis of OsBAK1L transgenic rice under field low nitrogen condition Table 58. The effective panicle number analysis of OsBAK1L transgenic rice under field normal nitrogen condition Table 59. Grain yield analysis of OsEIL2 transgenic rice under field low nitrogen condition Table 60. Grain yield analysis of OsEIL2 transgenic rice under field normal nitrogen condition Table 61. The effective panicle number analysis of OsEIL2 transgenic rice under field low nitrogen condition Table 62. The effective panicle number analysis of OsEIL2 transgenic rice under field normal nitrogen condition Table 63. Grain yield analysis of OsPPO3 transgenic rice under field low nitrogen condition Table 64. Grain yield analysis of OsPPO3 transgenic rice under field normal nitrogen condition Table 65. Flag leaf SPAD value analysis of OsPPO3 transgenic rice under field low nitrogen condition Table 66. Top second leaf SPAD value analysis of OsPPO3 transgenic rice under field low nitrogen condition Table 67. Grain yield analysis of OsTTP1 transgenic rice under field low nitrogen condition Table 68. Grain yield analysis of OsTTP1 transgenic rice under field normal nitrogen condition Table 69. Effective panicle number analysis of OsTTP1 transgenic rice under field low nitrogen condition Table 70. Effective panicle number analysis of OsTTP1 transgenic rice under field normal nitrogen condition Table 71. Flag leaf SPAD value analysis of OsTTP1 transgenic rice under field low nitrogen condition Table 72. Top second leaf SPAD value analysis of OsTTP1 transgenic rice under field low nitrogen condition Table 73. Enhanced drought tolerance of OsEIL2 transgenic rice plants under greenhouse conditions (construct level)

Table 74. Enhanced drought tolerance of OsEIL2 transgenic rice plants under greenhouse conditions (line level)

Table 75. Paraquat tolerance assay of OsEIL2 transgenic rice plants at transgenic line level (1$^{st}$ experiment)

Table 76. Paraquat tolerance assay of OsEIL2 transgenic rice plants at transgenic line level (2$^{nd}$ experiment)

Table 77. Enhanced cold tolerance of OsEIL2 transgenic rice plants under low temperature conditions (1$^{st}$ experiment)

Table 78. Enhanced cold tolerance of OsEIL2 transgenic rice plants under low temperature conditions (2$^{nd}$ experiment)

Table 79. Modified Hoagland's nutrient solution for culturing *Arabidopsis*

BRIEF DESCRIPTION OF THE SEQUENCE LISTINGS

The disclosure can be more fully understood from the following detailed description and Sequence Listing which form a part of this application.

TABLE 1

SEQ ID NOs for nucleotide and amino acid sequences provided in the sequence listing

| Source species | Clone Designation | SEQ ID NO: (Nucleotide) | SEQ ID NO: (Amino Acid) |
|---|---|---|---|
| Artificial | DP0005 vector | 1 | n/a |
| Artificial | DsRED expression cassette | 2 | n/a |
| Oryza sativa | OsDN-LTP4 | 3, 4 | 5 |
| Oryza sativa | OsDN-LTP6 | 6, 7 | 8 |
| Oryza sativa | OsDN-LTP7 | 9, 10 | 11 |
| Oryza sativa | OsBAK1L | 12, 13 | 14 |
| Oryza sativa | OsEIL2 | 15, 16 | 17 |
| Oryza sativa | OsPPO3 | 18, 19 | 20 |
| Oryza sativa | OsTTP1 | 21, 22 | 23 |
| Artificial | Primers | 24-51 | n/a |

The sequence descriptions and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. § 1.822.

SEQ ID NO: 1 is the nucleotide sequence of vector DP0005.

SEQ ID NO: 2 is the nucleotide sequence of DsRed expression cassette.

SEQ ID NO: 3 is the nucleotide sequence of gDNA of OsDN-LTP4 gene.

SEQ ID NO: 4 is the nucleotide sequence of CDS of OsDN-LTP4 gene.

SEQ ID NO: 5 is the amino acid sequence of OsDN-LTP4.

SEQ ID NO: 6 is the nucleotide sequence of gDNA of OsDN-LTP6 gene.

SEQ ID NO: 7 is the nucleotide sequence of CDS of OsDN-LTP6 gene.

SEQ ID NO: 8 is the amino acid sequence of OsDN-LTP6.

SEQ ID NO: 9 is the nucleotide sequence of cDNA of OsDN-LTP7 gene.

SEQ ID NO: 10 is the nucleotide sequence of CDS of OsDN-LTP7 gene.

SEQ ID NO: 11 is the amino acid sequence of OsDN-LTP7.

SEQ ID NO: 12 is the nucleotide sequence of cDNA of OsBAK1L gene.

SEQ ID NO: 13 is the nucleotide sequence of CDS of OsBAK1L gene.

SEQ ID NO: 14 is the amino acid sequence of OsBAK1L.

SEQ ID NO: 15 is the nucleotide sequence of cDNA of OsEIL2 gene.

SEQ ID NO: 16 is the nucleotide sequence of CDS of OsEIL2 gene.

SEQ ID NO: 17 is the amino acid sequence of OsEIL2.

SEQ ID NO: 18 is the nucleotide sequence of cDNA of OsPPO3 gene.

SEQ ID NO: 19 is the nucleotide sequence of CDS of OsPPO3 gene.

SEQ ID NO: 20 is the amino acid sequence of OsPPO3.

SEQ ID NO: 21 is the nucleotide sequence of gDNA of OsTTP1 gene.

SEQ ID NO: 22 is the nucleotide sequence of CDS of OsTTP1 gene.

SEQ ID NO: 23 is the amino acid sequence of OsTTP1.

SEQ ID NO: 24 is forward primer for cloning gDNA of OsDN-LTP4 gene.

SEQ ID NO: 25 is reverse primer for cloning gDNA of OsDN-LTP4 gene.

SEQ ID NO: 26 is forward primer for cloning gDNA of OsDN-LTP6 gene.

SEQ ID NO: 27 is reverse primer for cloning gDNA of OsDN-LTP6 gene.

SEQ ID NO: 28 is forward primer for cloning cDNA of OsDN-LTP7 gene.

SEQ ID NO: 29 is reverse primer for cloning cDNA of OsDN-LTP7 gene.

SEQ ID NO: 30 is forward primer for cloning cDNA of OsBAK1L gene.

SEQ ID NO: 31 is reverse primer for cloning cDNA of OsBAK1L gene.

SEQ ID NO: 32 is forward primer for cloning cDNA of OsEIL2 gene.

SEQ ID NO: 33 is reverse primer for cloning cDNA of OsEIL2 gene.

SEQ ID NO: 34 is forward primer for cloning cDNA of OsPPO3 gene.

SEQ ID NO: 35 is reverse primer for cloning cDNA of OsPPO3 gene.

SEQ ID NO: 36 is forward primer for cloning gDNA of OsTTP1 gene.

SEQ ID NO: 37 is reverse primer for cloning gDNA of OsTTP1 gene.

SEQ ID NO: 38 is forward primer for real-time RT-PCR analysis of OsDN-LTP4 gene.

SEQ ID NO: 39 is reverse primer for real-time RT-PCR analysis of OsDN-LTP4 gene.

SEQ ID NO: 40 is forward primer for real-time RT-PCR analysis of OsDN-LTP6 gene.

SEQ ID NO: 41 is reverse primer for real-time RT-PCR analysis of OsDN-LTP6 gene.

SEQ ID NO: 42 is forward primer for real-time RT-PCR analysis of OsDN-LTP7 gene.

SEQ ID NO: 43 is reverse primer for real-time RT-PCR analysis of OsDN-LTP7 gene.

SEQ ID NO: 44 is forward primer for real-time RT-PCR analysis of OsBAK1L gene.

SEQ ID NO: 45 is reverse primer for real-time RT-PCR analysis of OsBAK1L gene.

SEQ ID NO: 46 is forward primer for real-time RT-PCR analysis of OsEIL2 gene.

SEQ ID NO: 47 is reverse primer for real-time RT-PCR analysis of OsEIL2 gene.

SEQ ID NO: 48 is forward primer for real-time RT-PCR analysis of OsPPO3 gene.

SEQ ID NO: 49 is reverse primer for real-time RT-PCR analysis of OsPPO3 gene.

SEQ ID NO: 50 is forward primer for real-time RT-PCR analysis of OsTTP1 gene.

SEQ ID NO: 51 is reverse primer for real-time RT-PCR analysis of OsTTP1 gene.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The term "OsDN-LTP4 (low nitrogen tolerance protein 4)" refers to a rice polypeptide that confers a low nitrogen tolerance phenotype and is encoded by the rice gene locus LOC_Os07g12310. "DN-LTP4 polypeptide" refers herein to the OsDN-LTP4 polypeptide and its homologs from other organisms.

The OsDN-LTP4 polypeptide (SEQ ID NO: 5) is encoded by the coding sequence (CDS) (SEQ ID NO: 4) or nucleotide sequence (SEQ ID NO: 3) at rice gene locus LOC_Os07g12310. This polypeptide is annotated as "hypothetical protein" in TIGR, however does not have any prior assigned function.

The term "OsDN-LTP6 (low nitrogen tolerance protein 6)" refers to a rice polypeptide that confers a low nitrogen tolerance phenotype and is encoded by the rice gene locus LOC_Os09g10280. "DN-LTP6 polypeptide" refers herein to the OsDN-LTP6 polypeptide and its homologs from other organisms.

The OsDN-LTP6 polypeptide (SEQ ID NO: 8) is encoded by the coding sequence (CDS) (SEQ ID NO: 7) or nucleotide sequence (SEQ ID NO: 6) at rice gene locus LOC_Os09g10280. This polypeptide is annotated as "hypothetical protein" in TIGR.

The term "OsDN-LTP7 (low nitrogen tolerance protein 7)" refers to a rice polypeptide that confers a low nitrogen tolerance phenotype and is encoded by the rice gene locus LOC_Os09g10274. "DN-LTP7 polypeptide" refers herein to the OsDN-LTP7 polypeptide and its homologs from other organisms.

The OsDN-LTP7 polypeptide (SEQ ID NO: 11) is encoded by the coding sequence (CDS) (SEQ ID NO: 10) or nucleotide sequence (SEQ ID NO: 9) at rice gene locus LOC_Os09g10274. This polypeptide is annotated as "expressed protein" in TIGR.

The term "OsBAK1L (brassinosteroid insensitive 1-associated receptor kinase 1 like protein)" refers to a rice polypeptide that confers a low nitrogen tolerance phenotype and is encoded by the rice gene locus LOC_Os05g41230. "BAK1L polypeptide" refers herein to the OsBAK1L polypeptide and its homologs from other organisms.

The OsBAK1L polypeptide (SEQ ID NO: 14) is encoded by the coding sequence (CDS) (SEQ ID NO: 13) or nucleotide sequence (SEQ ID NO: 12) at rice gene locus LOC_Os05g41230. This polypeptide is annotated as "BRASSINOSTEROID INSENSITIVE 1-associated receptor kinase 1 precursor, putative, expressed" in TIGR, however does not have any prior assigned function.

The term "OsEIL2 (ethylene-insensitive 3 like protein 2)" refers to a rice polypeptide that confers a low nitrogen tolerance phenotype and is encoded by the rice gene locus LOC_Os07g48630. "EIL2 polypeptide" refers herein to the OsEIL2 polypeptide and its homologs from other organisms.

The OsEIL2 polypeptide (SEQ ID NO: 17) is encoded by the coding sequence (CDS) (SEQ ID NO: 16) or nucleotide sequence (SEQ ID NO: 15) at rice gene locus LOC_Os07g48630. This polypeptide is annotated as "ethylene-insensitive 3, putative, expressed" in TIGR.

The term "OsPPO3 (polyphenol oxidase protein 3)" refers to a rice polypeptide that confers a low nitrogen tolerance phenotype and is encoded by the rice gene locus LOC_Os04g53290. "PPO3 polypeptide" refers herein to the OsPPO3 polypeptide and its homologs from other organisms.

The OsPPO3 polypeptide (SEQ ID NO: 20) is encoded by the coding sequence (CDS) (SEQ ID NO: 19) or nucleotide sequence (SEQ ID NO: 18) at rice gene locus LOC_Os04g53290. This polypeptide is annotated as "polyphenol oxidase protein, putative" in TIGR.

The term "OsTTP1 (tryptophan/tyrosine permease protein 1)" refers to a rice polypeptide that confers a low nitrogen tolerance phenotype and is encoded by the rice gene locus LOC_Os07g12330. "TTP1 polypeptide" refers herein to the OsTTP1 polypeptide and its homologs from other organisms.

The OsTTP1 polypeptide (SEQ ID NO: 23) is encoded by the coding sequence (CDS) (SEQ ID NO: 22) or nucleotide sequence (SEQ ID NO: 21) at rice gene locus LOC_Os07g12330. This polypeptide is annotated as "tryptophan/tyrosine permease family protein, putative, expressed" in TIGR.

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

The term "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar or nitrogen concentrations, or by the observation of the expression level of a gene or genes, or by agricultural observations such as osmotic stress tolerance or yield.

"Agronomic characteristic" is a measurable parameter including but not limited to, greenness, yield, growth rate, biomass, fresh weight, dry weight at maturation, fruit yield, seed yield, total plant nitrogen content, fruit nitrogen content, seed nitrogen content, nitrogen content in vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, and ear length, early seedling vigor, and seedling emergence under low temperature stress.

"Harvest index" refers to the grain weight divided by the total plant weight.

Increased biomass can be measured, for example, as an increase in plant height, plant total leaf area, plant fresh weight, plant dry weight or plant grain yield, as compared with control plants.

The ability to increase the biomass or size of a plant would have several important commercial applications. Crop cultivars may be developed to produce higher yield of the vegetative portion of the plant, to be used in food, feed, fiber, and/or biofuel.

Increased leaf size may be of particular interest. Increased leaf biomass can be used to increase production of plant-derived pharmaceutical or industrial products.

Increased tiller number may be of particular interest and can be used to increase yield. An increase in total plant photosynthesis is typically achieved by increasing leaf area of the plant. Additional photosynthetic capacity may be used to increase the yield derived from particular plant tissue, including the leaves, roots, fruits or seed, or permit the growth of a plant under decreased light intensity or under high light intensity.

Modification of the biomass of another tissue, such as root tissue, may be useful to improve a plant's ability to grow under harsh environmental conditions, including nutrient deprivation, because larger roots may better reach or take up nutrients.

"Environmental conditions" refer to conditions under which the plant is grown, such as the availability of water, availability of nutrients (for example nitrogen), or the presence of insects or disease.

"Nitrogen limiting conditions" refers to conditions where the amount of total available nitrogen (e.g., from nitrates, ammonia, or other known sources of nitrogen) is not sufficient to sustain optimal plant growth and development. One skilled in the art would recognize conditions where total available nitrogen is sufficient to sustain optimal plant growth and development. One skilled in the art would recognize what constitutes sufficient amounts of total available nitrogen, and what constitutes soils, media and fertilizer inputs for providing nitrogen to plants. Nitrogen limiting conditions will vary depending upon a number of factors, including but not limited to, the particular plant and environmental conditions.

The terms "nitrogen stress tolerance", "low nitrogen tolerance" and "nitrogen deficiency tolerance" are used interchangeably herein, which indicate a trait of a plant and refer to the ability of the plant to survive under nitrogen limiting conditions or low nitrogen conditions.

"Increased nitrogen stress tolerance" of a polypeptide indicates that over-expression of the polypeptide in a transgenic plant confers increased nitrogen stress tolerance of the transgenic plant relative to a reference or control plant.

"Increased nitrogen stress tolerance" of a plant is measured relative to a reference or control plant, reflects ability of the plant to survive and/or grow better under nitrogen limiting conditions, and means that the nitrogen stress tolerance of the plant is increased by any amount or measured when compared to the nitrogen stress tolerance of the reference or control plant.

A "nitrogen stress tolerant plant" is a plant that exhibits nitrogen stress tolerance. A nitrogen stress tolerant plant can be a plant that exhibits an increase in at least one agronomic characteristic relative to a control plant under nitrogen limiting conditions.

"NUE" is nitrogen utilization efficiency and refers to a plant's ability to utilize nitrogen in low or high levels of fertilizer. It reflects the plant's ability to uptake, assimilate, and/or otherwise utilize nitrogen.

Soil plant analyses development (SPAD) value is SPAD reading which is measured by SPAD-502 plus (a chlorophyll meter, made by KONICA MINOLTA). the SPAD value is relative content of leaf chlorophyll and an important indicator of plant health. Many studies indicated that a significant and positive correlation was observed between leaf nitrogen content and SPAD value (Swain D. K. and Sandip S. J. (2010) *Journal of Agronomy* 9 (2):38-44), and leaf SPAD value is used as index of nitrogen status diagnosis in crops (Cai H.-G. et al. (2010) *Acta metallurgica sinica* 16 (4): 866-873).

The response and tolerance of rice plants to low nutrition stress is an integrated and comprehensive physiological and biochemical process. The resistance of plants will be reflected in different aspect under different plant development phase and different stress conditions. The environment factors such as illumination and temperature are critical factors which effect rice growth, and the variation of these environment factors will influence the growth and development of rice plants. Researches demonstrated that low nitrogen treated rice plants display low chlorophyll content in leaf, deduced tiller number, or reduced biomass. In our experiment, the leaf color (which can be indicated by chlorophyll, SPAD value), plant fresh weight, and tiller number are measured, and the low nitrogen resistance plants are selected by combining the three parameters.

"Chlorate" refers to a chemical compound containing chlorate anion, a salt of chloric acid. It is a nitrate analog which can be uptake by plant with same transport system like nitrate, and then converted by nitrate reductase to chlorite which is toxic and leads to plant damage, withering, and plant death. Potassium chlorate is used in this disclosure.

"Chlorate sensitivity" is a trait of plant, reflects the level of damage, even death after chlorate uptake, transport or reduction when treated with chlorate solution, compared to a reference or control plant.

"Increased Chlorate sensitivity" of a plant is measured relative to a reference or control plant, and reflects higher ability of the plant to chlorate or nitrate uptake, transport or reduction than a reference or control plant in chlorate or nitrate solution. In general, chlorate sensitivity can be used as a marker of NUE. The more sensitive plants are to chlorate, the higher the NUE.

"Chlorate sensitive seedlings" are the damaged seedlings with phenotype of withered leaves in whole and without green leaf, and considered as dead after treated with chlorate solution.

"Drought" refers to a decrease in water availability to a plant that, especially when prolonged or when occurring during critical growth periods, can cause damage to the plant or prevent its successful growth (e.g., limiting plant growth or seed yield).

"Drought tolerance" reflects a plant's ability to survive under drought without exhibiting substantial physiological or physical deterioration, and/or its ability to recover when water is restored following a period of drought.

"Drought tolerance activity" of a polypeptide indicates that over-expression of the polypeptide in a transgenic plant confers increased drought tolerance of the transgenic plant relative to a reference or control plant.

"Increased drought tolerance" of a plant is measured relative to a reference or control plant, and reflects ability of the plant to survive under drought conditions with less physiological or physical deterioration than a reference or control plant grown under similar drought conditions, or ability of the plant to recover more substantially and/or more quickly than would a control plant when water is restored following a period of drought.

"Environmental conditions" refer to conditions under which the plant is grown, such as the availability of water, availability of nutrients, or the presence of insects or disease.

"Paraquat" (1,1-dimethyl-4,4-bipyridinium dichloride), is a foliar-applied and non-selective bipyridinium herbicides, and causes photooxidative stress which further cause damage to plant or prevent its successful growth.

"Paraquat tolerance" is a trait of a plant, reflects the ability to survive and/or grow better when treated with Paraquat solution, compared to a reference or control plant.

"Increased paraquat tolerance" of a plant is measured relative to a reference or control plant, and reflects ability of the plant to survive with less physiological or physical deterioration than a reference or control plant after treated with paraquat solution. In general, tolerance to relative low level of paraquat can be used as a marker of abiotic stress tolerance, such as drought tolerance.

"Oxidative stress" reflects an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control" or "control plant" or "control plant cell" provides a reference point for measuring changes in phenotype of a subject plant or plant cell which was genetically altered by, such as transformation, and has been affected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to a condition or stimulus that would induce expression of the gene of interest; or (e) the subject plant or plant cell itself, under conditions in which the gene of interest is not expressed.

In this disclosure, ZH11-TC, event null, and empty vector plants indicate control plants. ZH11-TC represents rice plants generated from tissue cultured Zhonghua 11, line null represents segregated null plants, and empty vector represents plants transformed with empty vector DP0005 or DP0158.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. The heterologous polynucleotide can be stably integrated within the genome such that the polynucleotide is passed on to successive generations. The heterologous polynucleotide may be integrated into the genome alone or as part of a recombinant DNA construct. A $T_0$ plant is directly recovered from the transformation and regeneration process. Progeny of $T_0$ plants are referred to as $T_1$ (first progeny generation), $T_2$ (second progeny generation), etc.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenine, adenylate or deoxyadenylate (for RNA or DNA, respectively), "C" for cytosine, cytidylate or deoxycytidylate, "G" for guanine, guanylate or deoxyguanylate, "U" for uridine, uridylate, "T" for thymine, deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" and "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632). A "mitochondrial signal peptide" is an amino acid sequence which directs a precursor protein into the mitochondria (Zhang and Glaser (2002) *Trends Plant Sci* 7:14-21).

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, *CABIOS.* 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to the embodiments:

Embodiments include isolated polynucleotides and polypeptides, recombinant DNA constructs useful for conferring improved nitrogen use efficiency, compositions (such as plants or seeds) comprising these recombinant DNA constructs, and methods utilizing these recombinant DNA constructs.

Isolated Polynucleotides and Polypeptides

The present disclosure includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 5, 8, 11, 14, 17, 20 or 23; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. The polypeptide is low nitrogen tolerance protein. Over-expression of these polypeptide increase plant low nitrogen tolerance activity and/or drought and/or cold tolerance activity.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 5, 8, 11, 14, 17, 20 or 23. The polypeptide is low nitrogen tolerance protein.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 3, 4, 6, 7, 9, 10, 12, 13, 15, 16, 18, 19, 21 or 22; or (ii) a full complement of the nucleic acid sequence of (i). Any of the foregoing isolated polynucleotides may be utilized in any recombinant DNA constructs of the present disclosure. The isolated polynucleotide encodes low nitrogen tolerance protein. Over-expression of this polypeptide increase plant low nitrogen tolerance activity and/or drought and/or cold tolerance.

Recombinant DNA Constructs

In one aspect, the present disclosure includes recombinant DNA constructs.

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 5, 8, 11, 14, 17, 20 or 23; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 3, 4, 6, 7, 9, 10, 12, 13, 15, 16, 18, 19, 21 or 22; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide encodes low nitrogen tolerance polypeptide. These polypeptides have low nitrogen tolerance activity, and may be from, for example, *Oryza sativa, Oryza australiensis, Oryza barthii, Oryza glaberrima* (African rice), *Oryza latifolia, Oryza longistaminata, Oryza meridionalis, Oryza officinalis, Oryza punctata, Oryza rufipogon* (brownbeard or red rice), *Oryza nivara*(Indian wild rice), *Arabidopsis thaliana, Zea mays, Glycine max, Glycine tabacina, Glycine soja* or *Glycine tomentella*.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Regulatory Sequences:

A recombinant DNA construct of the present disclosure may comprise at least one regulatory sequence.

A regulatory sequence may be a promoter.

A number of promoters can be used in recombinant DNA constructs of the present disclosure. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High level, constitutive expression of the candidate gene under control of the 35S or UBI promoter may (or may not) have pleiotropic effects, although candidate gene efficacy may be estimated when driven by a constitutive promoter. Use of tissue-specific and/or stress-specific promoters may eliminate undesirable effects, but retain the ability to enhance nitrogen tolerance. This type of effect has been observed in *Arabidopsis* for drought and cold tolerance (Kasuga et al., *Nature Biotechnol.* 17:287-91 (1999)).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569, 597; 5,466,785; 5,399,680; 5,268,463; 5,608,142; and 6,177,611.

In choosing a promoter to use in the methods of the disclosure, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present disclosure which causes the desired temporal and spatial expression.

Promoters which are seed or embryo-specific and may be useful in the disclosure include soybean Kunitz trypsin inhibitor (Kti3, Jofuku and Goldberg, *Plant Cell* 1:1079-1093 (1989)), patatin (potato tubers) (Rocha-Sosa, M., et al., *EMBO J.* 8:23-29 (1989)), convicilin, vicilin, and legumin (pea cotyledons) (Rerie, W. G., et al., *Mol. Gen. Genet.* 259:149-157 (1991); Newbigin, E. J., et al., *Planta* 180:461-470 (1990); Higgins, T. J. V., et al., *Plant. Mol. Biol.* 11:683-695 (1988)), zein (maize endosperm) (Schemthaner, J. P., et al., *EMBO J.* 7:1249-1255 (1988)), phaseolin (bean cotyledon) (Segupta-Gopalan, C., et al., *Proc. Natl. Acad. Sci.* U.S.A. 82:3320-3324 (1995)), phytohemagglutinin (bean cotyledon) (Voelker, T. et al., *EMBO J.* 6:3571-3577 (1987)), B-conglycinin and glycinin (soybean cotyledon) (Chen, Z-L, et al., *EMBO J.* 7:297-302 (1988)), glutelin (rice endosperm), hordein (barley endosperm) (Marris, C., et al., *Plant Mol. Biol.* 10:359-366 (1988)), glutenin and gliadin (wheat endosperm) (Colot, V., et al., *EMBO J.* 6:3559-3564 (1987)), and sporamin (sweet potato tuberous root) (Hattori, T., et al., *Plant Mol. Biol.* 14:595-604 (1990)). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., *Bio/Technology* 7:L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J.* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in the current disclosure include the following: 1) the stress-inducible RD29A promoter (Kasuga et al., *Nature Biotechnol.* 17:287-91 (1999)); 2) the barley promoter, B22E; expression of B22E is specific to the pedicel in developing maize kernels ("Primary Structure of a Novel Barley Gene Differentially Expressed in Immature Aleurone Layers", Klemsdal et al., *Mol. Gen. Genet.* 228 (1/2):9-16 (1991)); and 3) maize promoter, Zag2 ("Identification and molecular characterization of ZAG1, the maize homolog of the *Arabidopsis* floral homeotic gene AGAMOUS", Schmidt et al., *Plant Cell* 5(7):729-737 (1993); "Structural characterization, chromosomal localization and phylogenetic evaluation of two pairs of AGAMOUS-like MADS-box genes from maize", Theissen et al., *Gene* 156 (2):155-166 (1995); NCBI GenBank Accession No. X80206)). Zag2 transcripts can be detected five days prior to pollination to seven to eight days after pollination ("DAP"), and directs expression in the carpel of developing female inflorescences and CimI which is specific to the nucleus of developing maize kernels. CimI transcript is detected four to five days before pollination to six to eight DAP. Other useful promoters include any promoter which can be derived from a gene whose expression is maternally associated with developing female florets.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all of its final mass, and various storage products (i.e., starch, protein, oil) are produced. Finally, the maturation phase occurs from about 40 DAP to harvest. During this phase of kernel development the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, Cim1 that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp. (WO 00/12733), herein incorporated by reference. Additional early kernel/embryo promoters that find use in certain methods of the present disclosure include the seed-preferred promoter ltp2 (U.S. Pat. No. 5,525,716); maize Zm40 promoter (U.S. Pat. No. 6,403,862); maize nuc1c (U.S. Pat. No. 6,407,315); maize ckx1-2 promoter (U.S. Pat. No. 6,921,815 and US Patent Application Publication Number 2006/0037103); maize lec1 promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007). Additional promoters for regulating the expression of the nucleotide sequences of the present disclosure in plants are stalk-specific promoters. Such stalk-specific promoters include the alfalfa S2A promoter (GenBank Accession No. EF030816; Abrahams et al., *Plant Mol. Biol.* 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (GenBank Accession No. EF030817), and the constitutive promoter GOS2 from *Zea mays*. Other promoters include root preferred promoters, such as the maize NAS2 promoter, the maize Cyclo promoter (US Publication No. 2006/0156439, published Jul. 13, 2006), the maize ROOT-MET2 promoter (WO 2005/063998, published Jul. 14, 2005), the CR1B10 promoter (WO 2006/055487, published May 26, 2006), the CRWAQ81 (WO 2005/035770, published Apr. 21, 2005) and the maize ZRP2.47 promoter (NCBI Accession No. U38790; NCBI GI No. 1063664).

Recombinant DNA constructs of the present disclosure may also include other regulatory sequences including, but not limited to, translation leader sequences, introns, and polyadenylation recognition sequences. In another embodiment of the present disclosure, a recombinant DNA construct of the present disclosure further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395-4405 (1988); Callis et al., *Genes Dev.* 1:1183-1200 (1987)).

Any plant can be selected for the identification of regulatory sequences and genes to be used in recombinant DNA constructs of the present disclosure. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, *eucalyptus*, fennel, figs, garlic, gourd, grape, grapefruit, honey dew, jicama, kiwifruit, lettuce, leeks, lemon, lime, Loblolly pine, linseed, maize, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

Compositions

A composition of the present disclosure is a plant comprising in its genome any of the recombinant DNA constructs of the present disclosure (such as any of the constructs discussed above). Compositions also include any progeny of the plant, and any seed obtained from the plant or its progeny, wherein the progeny or seed comprises within its genome the recombinant DNA construct. Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct. These seeds can be grown to produce plants that would exhibit an altered agronomic characteristic (e.g., an increased agronomic characteristic optionally under nitrogen limiting conditions), or used in a breeding program to produce hybrid seed, which can be grown to produce plants that would exhibit such an altered agronomic characteristic. The seeds may be maize seeds, or rice seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley or millet.

The recombinant DNA construct is stably integrated into the genome of the plant.

Embodiments include but are not limited to the following:

1. A transgenic plant (for example, a rice, maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 5, 8, 11, 14, 17, 20 or 23; and wherein said plant exhibits increased nitrogen stress tolerance and/or drought and/or cold tolerance when compared to a control plant not comprising said recombinant DNA construct. The plant may further exhibit an alteration of at least one agronomic characteristic when compared to the control plant.

2. A transgenic plant (for example, a rice, maize or soybean plant) comprising in its genome a recombinant DNA construct comprising a polynucleotide operably linked to at least one regulatory sequence, wherein said polynucleotide encodes a low nitrogen tolerance polypeptide, and wherein said plant exhibits increased nitrogen stress tolerance and/or drought and/or cold tolerance when compared to a control plant not comprising said recombinant DNA construct. The plant may further exhibit an alteration of at least one agronomic characteristic when compared to the control plant.

3. Any progeny of the above plants in embodiment 1-2, any seeds of the above plants in embodiment 1-2, any seeds of progeny of the above plants in embodiment 1-2, and cells from any of the above plants in embodiment 1-2 and progeny thereof.

In any of the foregoing embodiment 1-3 or any other embodiments of the present disclosure, the recombinant DNA construct may comprise at least a promoter functional in a plant as a regulatory sequence.

In any of the foregoing embodiment 1-3 or any other embodiments of the present disclosure, the alteration of at least one agronomic characteristic is either an increase or decrease.

In any of the foregoing embodiment 1-3 or any other embodiments of the present disclosure, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear length, early seedling vigor, and seedling emergence under low temperature stress. For example, the alteration of at least one agronomic characteristic may be an increase in yield, greenness, or biomass.

In any of the foregoing embodiment 1-3 or any other embodiments of the present disclosure, the plant may exhibit the alteration of at least one agronomic characteristic when compared, under nitrogen stress conditions, to a control plant not comprising said recombinant DNA construct.

One of ordinary skill in the art is familiar with protocols for simulating nitrogen conditions, whether limiting or non-limiting, and for evaluating plants that have been subjected to simulated or naturally-occurring nitrogen conditions, whether limiting or non-limiting. For example, one can simulate nitrogen conditions by giving plants less nitrogen than normally required or no nitrogen over a period of time, and one can evaluate such plants by looking for differences in agronomic characteristics, e.g., changes in physiological and/or physical condition, including (but not limited to) vigor, growth, size, or root length, or in particular, leaf color or leaf area size. Other techniques for evaluating such plants include measuring chlorophyll fluorescence, photosynthetic rates, root growth or gas exchange rates.

The examples below describe some representative protocols and techniques for simulating nitrogen limiting conditions and/or evaluating plants under such conditions.

One can also evaluate nitrogen stress tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring low or high nitrogen conditions (e.g., by measuring for substantially equivalent yield under low or high nitrogen conditions compared to normal nitrogen conditions, or by measuring for less yield loss under low or high nitrogen conditions compared to a control or reference plant).

SPAD value can be measured during low or high nitrogen condition in the field and greenhouse test by a chlorophyll meter. The SPAD value is a parameter indicating the plant health, and reflects plant nitrogen content by predicting the chlorophyll content. The plants with higher low nitrogen tolerance will have higher SPAD value compared to a control or reference plant.

One of ordinary skill in the art would readily recognize a suitable control or reference plant to be utilized when assessing or measuring an agronomic characteristic or phenotype of a transgenic plant in any embodiment of the present disclosure in which a control is utilized (e.g., compositions or methods as described herein). For example, by way of non-limiting illustrations:

1. Progeny of a transformed plant which is hemizygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct (i.e., the progeny not comprising the recombinant DNA construct is the control or reference plant).

2. Introgression of a recombinant DNA construct into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A plant comprising a recombinant DNA construct: the plant may be assessed or measured relative to a control plant not comprising the recombinant DNA construct but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct. There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Methods

Methods include but are not limited to methods for increasing nitrogen stress tolerance in a plant, methods for evaluating nitrogen stress tolerance in a plant, methods for increasing chlorate sensitive in a plant, methods for altering an agronomic characteristic in a plant, methods for determining an alteration of an agronomic characteristic in a plant, and methods for producing seed. The plant may be a monocotyledonous or dicotyledonous plant, for example, a rice, maize, *Arabidopsis*, soybean plant. The plant may also be sunflower, sorghum, canola, wheat, alfalfa, cotton, barley or millet. The seed may be a rice, maize, *Arabidopsis* or soybean seed, for example a maize hybrid seed or maize inbred seed.

Methods include but are not limited to the following:

A method for transforming a cell comprising transforming a cell with any of the isolated polynucleotides of the present disclosure. The cell transformed by this method is also included. In particular embodiments, the cell is eukaryotic cell, e.g., a yeast, insect or plant cell, or prokaryotic, e.g., a bacterium.

A method for producing a transgenic plant comprising transforming a plant cell with any of the isolated polynucleotides or recombinant DNA constructs of the present disclosure and regenerating a transgenic plant from the transformed plant cell. The disclosure is also directed to the transgenic plant produced by this method, and transgenic seed obtained from this transgenic plant.

A method for isolating a polypeptide of the disclosure from a cell or culture medium of the cell, wherein the cell comprises a recombinant DNA construct comprising a polynucleotide of the disclosure operably linked to at least one regulatory sequence, and wherein the transformed host cell is grown under conditions that are suitable for expression of the recombinant DNA construct.

A method of altering the level of expression of a polypeptide of the disclosure in a host cell comprising: (a) transforming a host cell with a recombinant DNA construct of the present disclosure; and (b) growing the transformed host cell under conditions that are suitable for expression of the recombinant DNA construct wherein expression of the recombinant DNA construct results in production of altered levels of the polypeptide of the disclosure in the transformed host cell.

A method of increasing nitrogen stress tolerance and/or chlorate sensitivity in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 5, 8, 11, 14, 17, 20 or 23; and (b) regenerating a transgenic plant from the regenerable plant cell after step (a), wherein the transgenic plant comprises in its genome the recombinant DNA construct and exhibits increased nitrogen stress tolerance and/or chlorate sensitivity when compared to a control plant not comprising the recombinant DNA construct. The method may further comprise (c) obtaining a progeny plant derived from the transgenic plant, wherein said progeny plant comprises in its genome the recombinant DNA construct and exhibits increased nitrogen tolerance and/or chlorate sensitivity when compared to a control plant not comprising the recombinant DNA construct.

A method of evaluating nitrogen stress tolerance and/or chlorate sensitivity in a plant, comprising (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 5, 8, 11, 14, 17, 20 or 23; (b) regenerating a transgenic plant from the regenerable plant cell after step (a), wherein the transgenic plant comprises in its genome the recombinant DNA construct; and (c) evaluating the transgenic plant for nitrogen stress tolerance and/or chlorate sensitivity compared to a control plant not comprising the recombinant DNA construct. The method may further comprise (d) obtaining a progeny plant derived from the transgenic plant, wherein the progeny plant comprises in its genome the recombinant DNA construct; and (e) evaluating the progeny plant for nitrogen stress tolerance and/or chlorate sensitivity compared to a control plant not comprising the recombinant DNA construct.

A method of increasing drought and/or cold tolerance and/or paraquat tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 17; and (b) regenerating a transgenic plant from the regenerable plant cell after step (a), wherein the transgenic plant comprises in its genome the recombinant DNA construct and exhibits increased drought and/or cold and/or paraquat tolerance when compared to a control plant not comprising the recombinant DNA construct. The method may further comprise (c) obtaining a progeny plant derived from the transgenic plant, wherein said progeny plant comprises in its genome the recombinant DNA construct and exhibits increased drought and/or cold and/or paraquat tolerance when compared to a control plant not comprising the recombinant DNA construct. A method of determining an alteration of an agronomic characteristic in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 5, 8, 11, 14, 17, 20 or 23; (b) regenerating a transgenic plant from the regenerable plant cell after step (a), wherein the transgenic plant comprises in its genome said recombinant DNA construct; and (c) determining whether the transgenic plant exhibits an alteration of at least one agronomic characteristic when compared, optionally under nitrogen limiting conditions and/or drought tolerance, to a control plant not comprising the recombinant DNA construct. The method may further comprise (d) obtaining a progeny plant derived from the transgenic plant, wherein the progeny plant comprises in its genome the recombinant DNA construct; and (e) determining whether the progeny plant exhibits an alteration of at least one agronomic characteristic when compared, optionally under nitrogen limiting conditions and/or drought tolerance, to a control plant not comprising the recombinant DNA construct.

A method of producing seed comprising any of the preceding methods, and further comprising obtaining seeds from said progeny plant, wherein said seeds comprise in their genome said recombinant DNA construct.

In any of the preceding methods or any other embodiments of methods of the present disclosure, the step of determining an alteration of an agronomic characteristic in a transgenic plant, if applicable, may comprise determining whether the transgenic plant exhibits an alteration of at least one agronomic characteristic when compared, under varying environmental conditions, to a control plant not comprising the recombinant DNA construct.

In any of the preceding methods or any other embodiments of methods of the present disclosure, the step of determining an alteration of an agronomic characteristic in a progeny plant, if applicable, may comprise determining whether the progeny plant exhibits an alteration of at least one agronomic characteristic when compared, under varying environmental conditions, to a control plant not comprising the recombinant DNA construct.

In any of the preceding methods or any other embodiments of methods of the present disclosure, in said introducing step said regenerable plant cell may comprises a callus cell, an embryogenic callus cell, a gametic cell, a meristematic cell, or a cell of an immature embryo. The regenerable plant cells may derive from an inbred maize plant.

In any of the preceding methods or any other embodiments of methods of the present disclosure, said regenerating step may comprise: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present disclosure, the plant may exhibit the alteration of at least one agronomic characteristic when compared, under nitrogen stress conditions, to a control plant not comprising said recombinant DNA construct.

In any of the preceding methods or any other embodiments of methods of the present disclosure, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant disclosure.

The introduction of recombinant DNA constructs of the present disclosure into plants may be carried out by any suitable technique, including but not limited to direct DNA uptake, chemical treatment, electroporation, microinjection, cell fusion, infection, vector mediated DNA transfer, bombardment, or Agrobacterium mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

In general, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" or engineered endonucleases such as meganucleases produced to modify plant genomes (see e.g., WO 2009/114321; Gao et al. (2010) Plant Journal 1:176-187). Another site-directed engineering is through the use of zinc finger domain recognition coupled with the restriction properties of restriction enzyme. See e.g., Urnov, et al., (2010) Nat Rev Genet. 11(9):636-46; Shukla, et al., (2009) Nature 459 (7245):437-41. A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The CRISPR/Cas system allows targeted cleavage of genomic DNA guided by a customizable small noncoding RNA.

EXAMPLES

The present disclosure is further illustrated in the following examples, in which parts and percentages are by weight and degrees are Celsius, unless otherwise stated. It should be understood that these examples, while indicating embodiments of the disclosure, are given by way of illustration only. From the above discussion and these examples, one skilled in the art can ascertain the essential characteristics of this disclosure, and without departing from the spirit and scope thereof, can make various changes and modifications of the disclosure to adapt it to various usages and conditions. Furthermore, various modifications of the disclosure in addition to those shown and described herein will be apparent to those skilled in the art from the foregoing description. Such modifications are also intended to fall within the scope of the appended claims.

Example 1

Abiotic Stress Tolerance Genes Cloning and Over-Expression Vectors Construction

Based on preliminary screening of rice activation tagging population and the sequences information of gene ID shown in the Table 2, primers were designed for cloning rice genes OsDN-LTP4, OsDN-LTP6, OsDN-LTP7, OsBAK1L, OsEIL2, OsPPO3 and OsTTP1. The primers and the expected-lengths of the amplified genes are shown in Table 3.

For OsDN-LTP7, OsBAK1L, OsEIL2 and OsPPO3, their cDNA were cloned by PCR using pooled cDNA from leaf, stem and root tissues of Zhonghua 11 plant as the template. For OsDN-LTP4, OsDN-LTP6 and OsTTP1, their gDNAs was cloned, and amplified using genomic DNA of Zhonghua 11 as the template. The PCR reaction mixtures and PCR procedures are shown in Table 4 and Table 5.

TABLE 2

Rice gene names, Gene IDs (from TIGR) and Construct IDs

| Gene name | Gene LOC ID | Construct ID |
| --- | --- | --- |
| OsDN-LTP4 | LOC_Os07g12310 | DP0036 |
| OsDN-LTP6 | LOC_Os09g10280 | DP0046 |

TABLE 2-continued

Rice gene names, Gene IDs (from TIGR) and Construct IDs

| Gene name | Gene LOC ID | Construct ID |
|---|---|---|
| OsDN-LTP7 | LOC_Os09g10274 | DP0063 |
| OsBAK1L | LOC_Os05g41230 | DP0066 |
| OsEIL2 | LOC_Os07g48630 | DP0069 |
| OsPPO3 | LOC_Os04g53290 | DP0097 |
| OsTTP1 | LOC_Os07g12330 | DP0299 |

TABLE 3

Primers for cloning rice abiotic stress tolerance genes

| Primer | Sequence | SEQ ID NO: | Gene name | Length of amplified fragment (bp) |
|---|---|---|---|---|
| gc-226 | 5'-ATGGAGTTCGGGAGGCCTGCTTG-3' | 24 | OsDN-LTP4 | 2132 |
| gc-227 | 5'-TCACCTATACTGGTCAACAGTGAATCTCC-3 | 25 | | |
| gc-476 | 5'-GATCCAACAGACAACTCTAACACTAGG-3' | 26 | OsDN-LTP6 | 894 |
| gc-477 | 5'-CGTCCCGAAGCCTTGCACTCATG-3' | 27 | | |
| DEgc-471 | 5'-GCTTGGCTTCGACGACCTTATCATC-3' | 28 | OsDN-LTP7 | 547 |
| DEgc-472 | 5'-TCCTCACAAAATCATGACAAGATAAACTGA-3' | 29 | | |
| DEgc-556 | 5'-GCACGAGGCACCACCGCAGC-3' | 30 | OsBAK1L | 740 |
| DEgc-557 | 5'-CCGCCGCCGTCCTCTTCTTTTTATTCG-3' | 31 | | |
| gc-304 | 5'-AATTCGTTTCAGTAGAACCAGTTGGATC-3' | 32 | OsEIL2 | 1868 |
| gc-305 | 5'-CCGCCATCGCCAAGTACCAG-3' | 33 | | |
| gc-601 | 5'-GGCCAGTAATCACATACACAGTTTGACAC-3' | 34 | OsPPO3 | 829 |
| gc-602 | 5'-CCACCGTCTTTCTCGGAGAACGCTTC-3' | 35 | | |
| GC-48 up | 5'-ATGCCCGACCCGAAAATGTGCCTGTAG-3' | 36 | OsTTP1 | 6631 |
| GC-48 down | 5'-CATGAATCCAAAAAAAAAAGGCAAATGG-3' | 37 | | |

TABLE 4

PCR reaction mixture for cloning abiotic stress tolerance genes

| Reaction mix | 50 μL |
|---|---|
| Template | 1 μL |
| TOYOBO KOD-FX (1.0 U/μL) | 1 μL |
| 2xPCR buffer for KOD-FX | 25 μL |
| 2 mM dNTPs (0.4 mM each) | 10 μL |
| Primer-F/R (10 μM) | 2 μL each |
| ddH$_2$O | 9 μL |

TABLE 5

PCR cycle conditions for abiotic stress tolerance genes

| 94° C. | 3 min | |
|---|---|---|
| 98° C. | 10 s | |
| 58° C. | 30 s | ×30 |
| 68° C. | (1 Kb/min) 1 min | |
| 68° C. | 5 min | |

The PCR amplified products were extracted after the agarose gel electrophoresis using a column kit and then ligated with TA cloning vectors. The sequences and orientation in these constructs were confirmed by sequencing. Then these genes were cloned into plant binary construct DP0005 (pCAMBIA1300-AsRed) (SEQ ID NO: 1) or DP0158 which was generated by transferring DsRed gene expression cassette (SEQ ID NO: 2 in the sequence list) into construct DP0005.

OsDN-LTP4, OsDN-LTP6, OsDN-LTP7, OsBAK1L and OsEIL2 were cloned into construct of DP0005. The generated over-expression vectors were listed in Table 2. The cloned nucleotide sequence in construct of DP0036 and coding sequence of OsDN-LTP4 are provided as SEQ ID NO: 3 and 4, the encoded amino acid sequence of OsDN-LTP4 is shown in SEQ ID NO: 5; the cloned nucleotide sequence in construct of DP0046 and coding sequence of OsDN-LTP6 are provided as SEQ ID NO: 6 and 7, the encoded amino acid sequence of OsDN-LTP6 is shown in SEQ ID NO: 8; the cloned nucleotide sequence in construct of DP0063 and coding sequence of OsDN-LTP7 are provided as SEQ ID NO: 9 and 10, the encoded amino acid sequence of OsDN-LTP7 is shown in SEQ ID NO: 11; the cloned nucleotide sequence in construct of DP0066 and coding sequence of OsBAK1L are provided as SEQ ID NO: 12 and 13, the encoded amino acid sequence of OsBAK1L is shown in SEQ ID NO: 14; and the cloned nucleotide sequence in construct of DP0069 and coding sequence of OsEIL2 are provided as SEQ ID NO: 15 and 16, the encoded amino acid sequence of OsEIL2 is shown in SEQ ID NO: 17.

OsPPO3 and OsTTP1 were cloned into construct of DP0158. The cloned nucleotide sequence in construct of DP0097 and coding sequence of OsPPO3 are provided as SEQ ID NO: 18 and 19, the encoded amino acid sequence of OsPPO3 is shown in SEQ ID NO: 20; and the cloned nucleotide sequence in construct of DP0299 and coding sequence of OsTTP1 are provided as SEQ ID NO: 21 and 22, the encoded amino acid sequence of OsTTP1 is shown in SEQ ID NO: 23.

Example 2

Generation of Transgenic Rice Plants

The over-expression vectors and empty vectors (DP0005 and DP0158) were transformed into the Zhonghua 11 (*Oryza*

*sativa* L.) by Agrobacteria-mediated method described by Lin and Zhang ((2005) *Plant Cell Rep.* 23:540-547). Zhonghua 11 was cultivated by the Institute of Crop Sciences, Chinese Academy of Agricultural Sciences. The first batch of seeds used in this research was provided by Beijing Weiming Kaituo Agriculture Biotech Co., Ltd. The calli induced from embryos was transformed with Agrobacteria with the vector. The transgenic seedlings ($T_0$) generated in transformation laboratory are transplanted in the field to get $T_1$ seeds. The $T_1$ and $T_2$ seeds are stored at cold room (4° C.), and $T_2$ seeds were used for following trait screening.

OsDN-LTP4, OsDN-LTP6, OsDN-LTP7, OsBAK1L and OsEIL2 transgenic seeds did not show red color under green fluorescent light. The $T_1$ transgenic plants were selected by hygromycin by culturing the rice plants (from 1-2 cm in height) in 50 mg/L hygromycin solution, the survived plants (hygromycin-resistant) were planted in field to produce $T_2$ seeds. Only the hygromycin-resistant $T_2$ transgenic rice plants were used in trait screen.

OsPPO3 and OsTTP1 transgenic seeds which showed red color under green fluorescent light (transgenic seeds) were used in the following assays.

Example 3

Gene Expression Analysis

The gene expression levels in the transgenic rice plants were analyzed. A standard RT-PCR or a real-time PCR procedure, such as the QuantiTect® Reverse Transcription Kit from Qiagen® and Real Time-PCR(SYBR®Premix Ex Taq™, TaKaRa), was used. EF1α gene was used as an internal control to show that the amplification and loading of samples from the transgenic rice and wild-type were similar. Gene expression was normalized based on the EF1α mRNA levels.

As shown in FIG. 1, OsDN-LTP4 gene over-expressed in the leaves of transgenic rice plants, whereas, the expression level of OsDN-LTP4 gene in the leaves of ZH11 was not detected. The primers used for the RT-PCR assay are as below:

```
DP0036-1:
                                    (SEQ ID NO: 38)
5'-GATGTGCCATATCTTTGTTC-3'

DP0036-2:
                                    (SEQ ID NO: 39)
5'-GAGGAAATGAACTGCTCTC-3'
```

Figure 2:
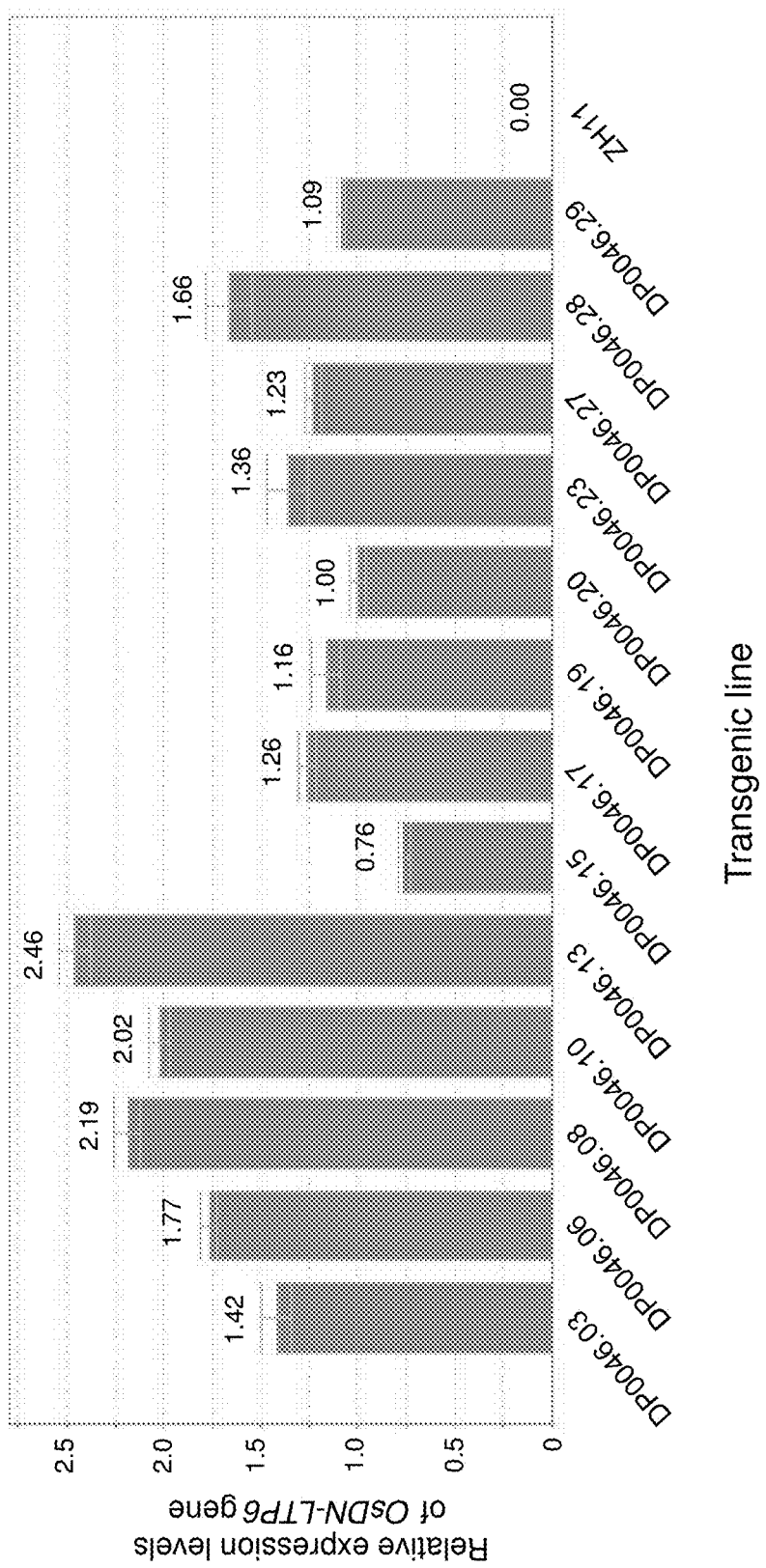

As shown in FIG. 2, the expression level of OsDN-LTP6 gene in DP0046.20 rice plant is set at 1.00, OsDN-LTP6 over-expressed in all the tested transgenic rice lines, while the expression of OsDN-LTP6 was not detected in ZH11 plants. The primers used for the real-time PCR are as below:

```
DP0046-f:
                                    (SEQ ID NO: 40)
5'-CTTCTCCGTCCTCCTCG-3'

DP0046-r:
                                    (SEQ ID NO: 41)
5'-GTGTGCCCTCCATGTCC-3'
```

Figure 3:
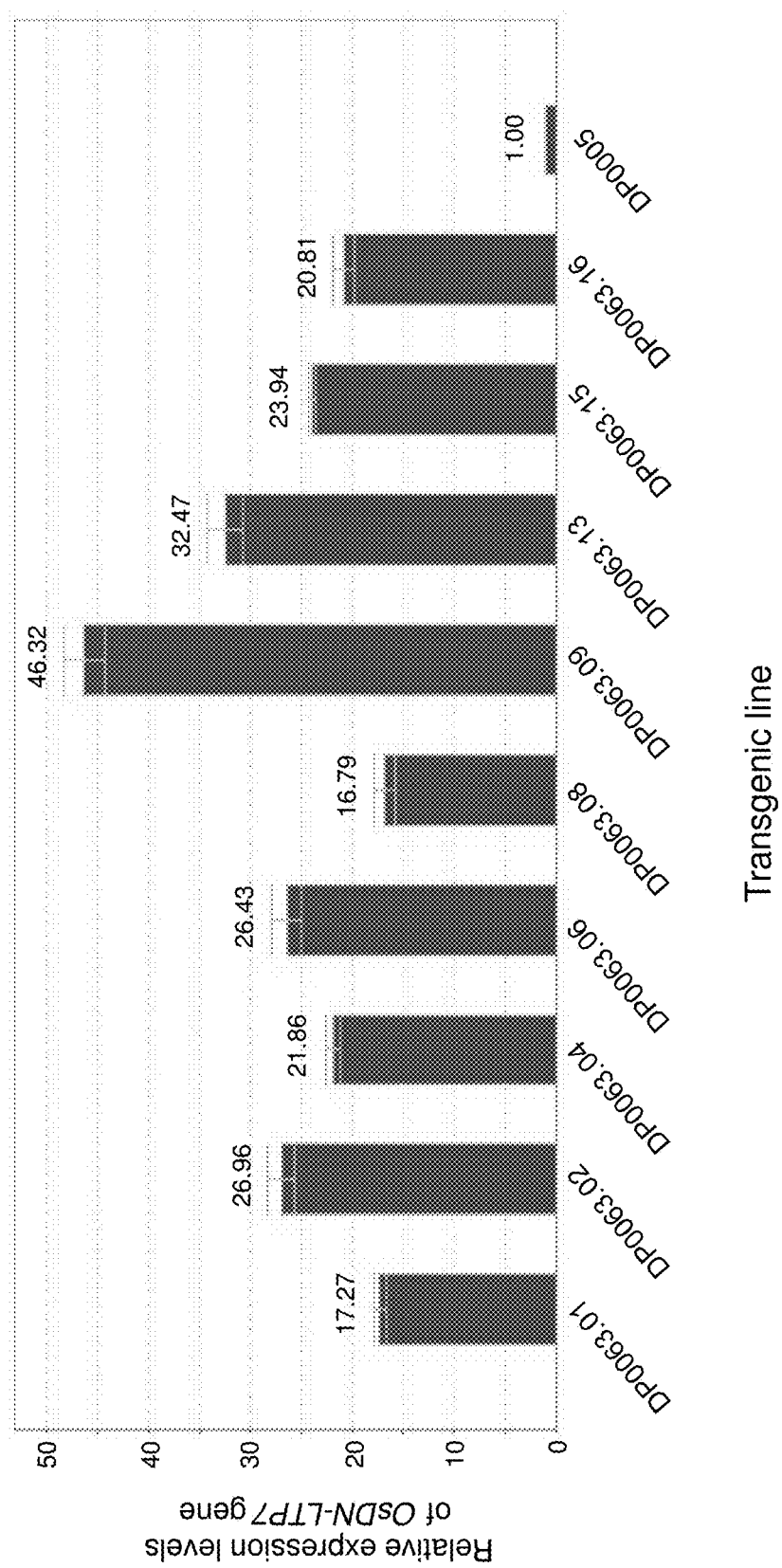

As shown in FIG. 3, the expression level of OsDN-LTP7 gene in empty vector transgenic (DP0005) rice is set at 1.00, OsDN-LTP7 over-expressed in all the transgenic lines, while the expression levels of OsDN-LTP4 were very low in DP0005 control

```
DP0063-1:
                                    (SEQ ID NO: 42)
5'-GACCAGAGCTCGTACCCTAACCC-3'

DP0063-2:
                                    (SEQ ID NO: 43)
5'-GGAGGCAAGCAAGGAGGTTATC-3'
```

Figure 4:
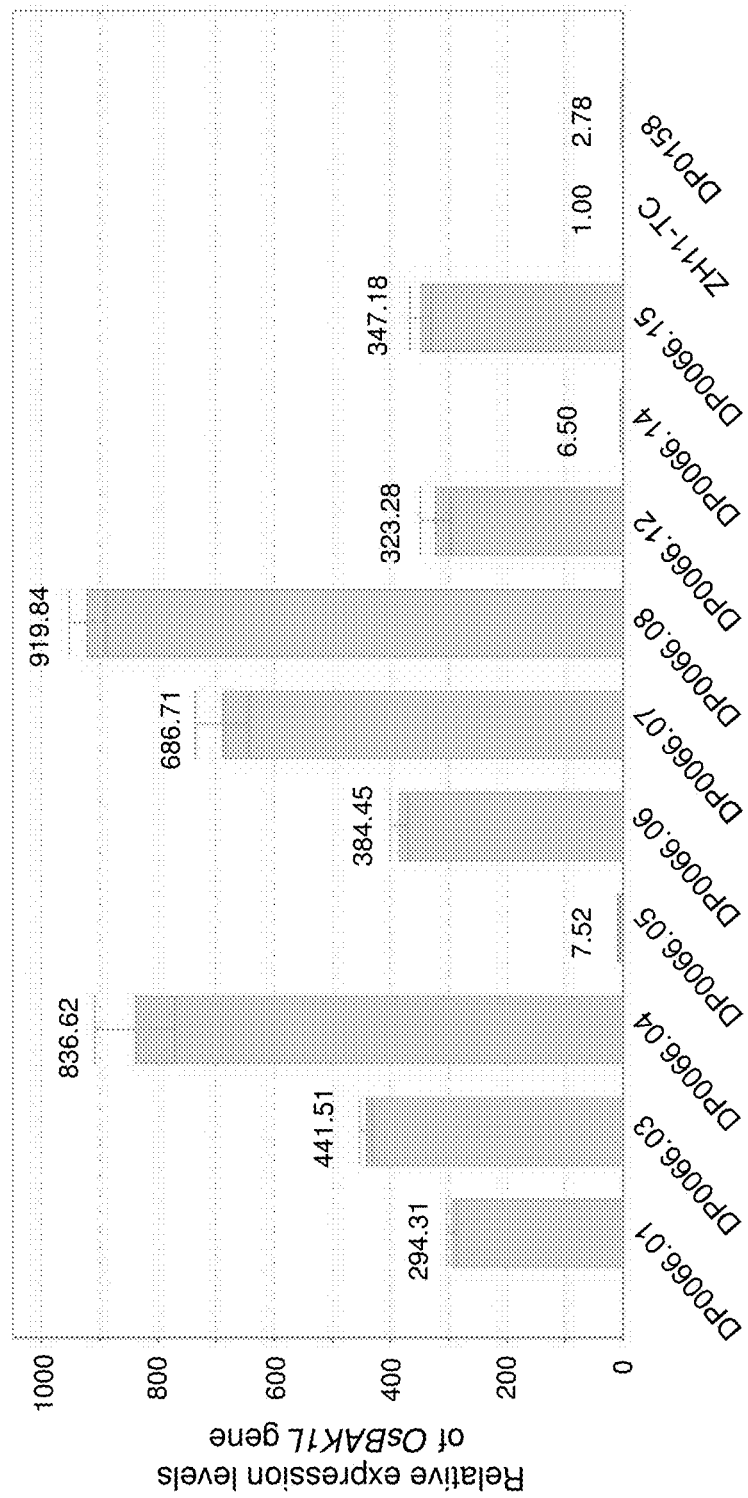

The expression level of OsBAK1L gene in ZH11-TC rice is set at 1.00, OsBAK1L over-expressed in all the ten transgenic rice lines, whereas, the expression levels of OsBAK1L gene were not detected in ZH11-TC and DP0158 plants (FIG. 4).

```
DP0066-F1:
                                    (SEQ ID NO: 44)
5'-CCTTTTAACTGGGCCAATCC-3'

DP0066-R1:
                                    (SEQ ID NO: 45)
5'-GGAGGGAAGTGATCGAACG-3'
```

Figure 5:
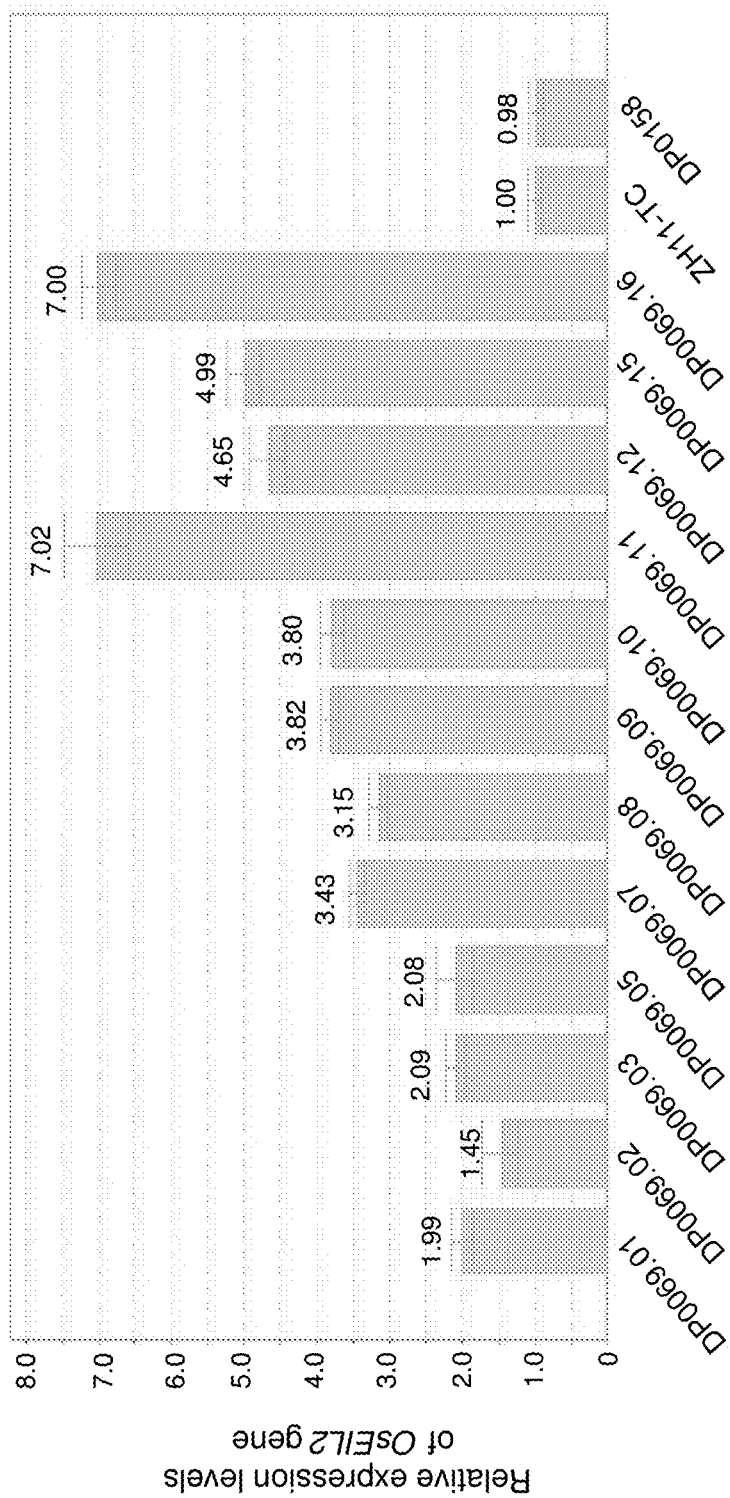
FIG. 5 shows the relative expression levels of OsEIL2 gene in leaves of different transgenic rice lines by real-time PCR analyses. The base expression level in ZH11-TC is set at 1.00, the numbers on the top of the columns are fold-changes compared to ZH11-TC rice.

The expression level of OsEIL2 gene in ZH11-TC rice is set at 1.00, OsEIL2 over-expressed in all the tested transgenic rice lines, while the expression levels of OsEIL2 gene were low in ZH11-TC and DP0158 plants (FIG. 5).

```
DP0069-F1:
                                    (SEQ ID NO: 46)
5'-GCACATCTTCGAGCCACTC-3'

DP0069-R1:
                                    (SEQ ID NO: 47)
5'-TCGCGGATGAAGAAATTAGC-3'
```

Figure 6:
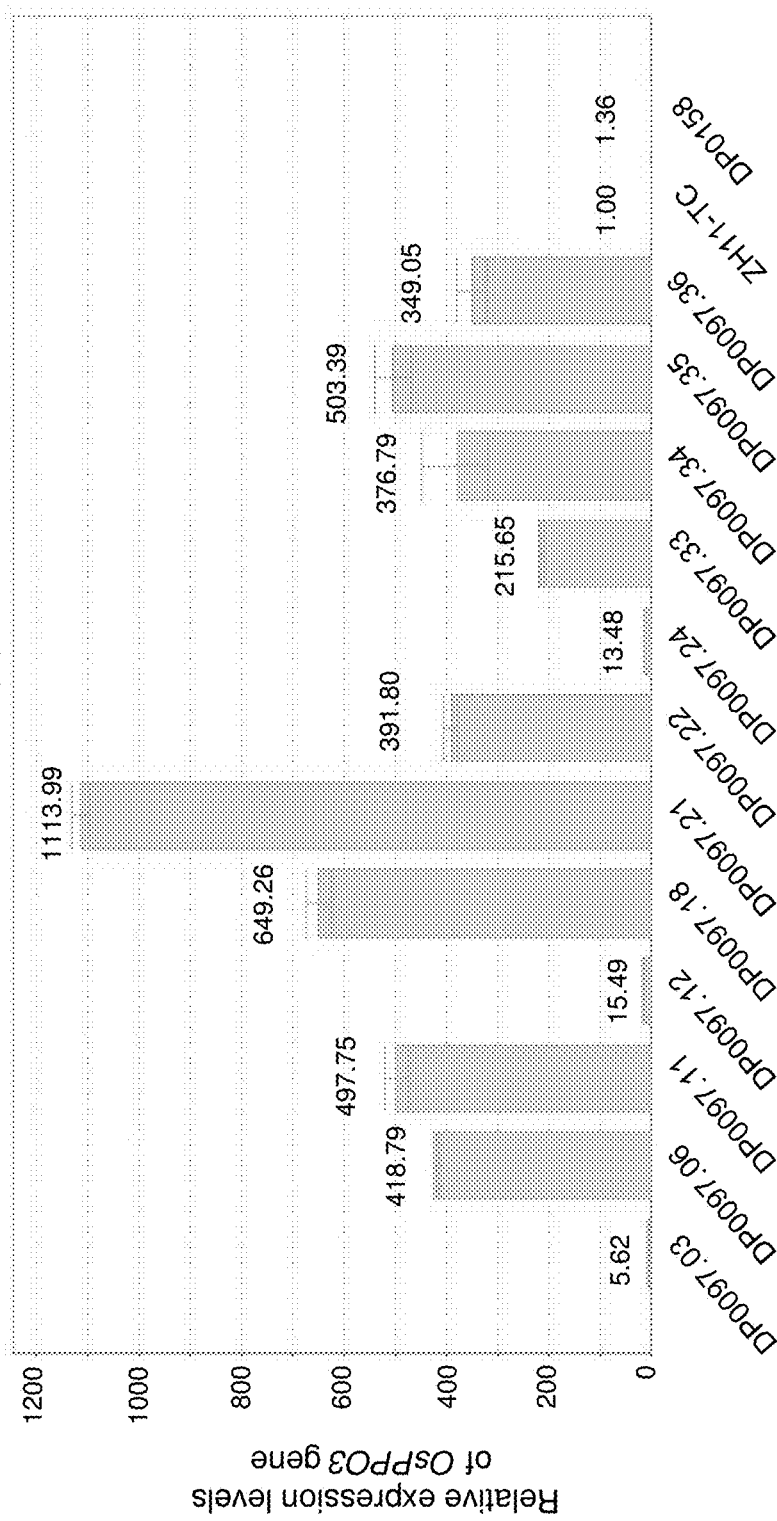
FIG. 6 shows the relative expression levels of OsPPO3 gene in leaves of different transgenic rice lines by real-time PCR analyses. The base expression level in ZH11-TC is set at 1.00, the numbers on the top of the columns are fold-changes compared to ZH11-TC rice.

The expression level of OsPPO3 gene in ZH11-TC rice is set at 1.00, OsPPO3 over-expressed in all the tested transgenic rice lines. The expression levels of OsPPO3 were low in ZH11-TC and DP0158 rice plants (FIG. 6).

```
DP0097-F1:
                                    (SEQ ID NO: 48)
5'-CATGGGCATGTTCTACTCGG-3'

DP0097-R1:
                                    (SEQ ID NO: 49)
5'-GTCGGTGAAGTCGGTGTC-3'
```

Figure 7:
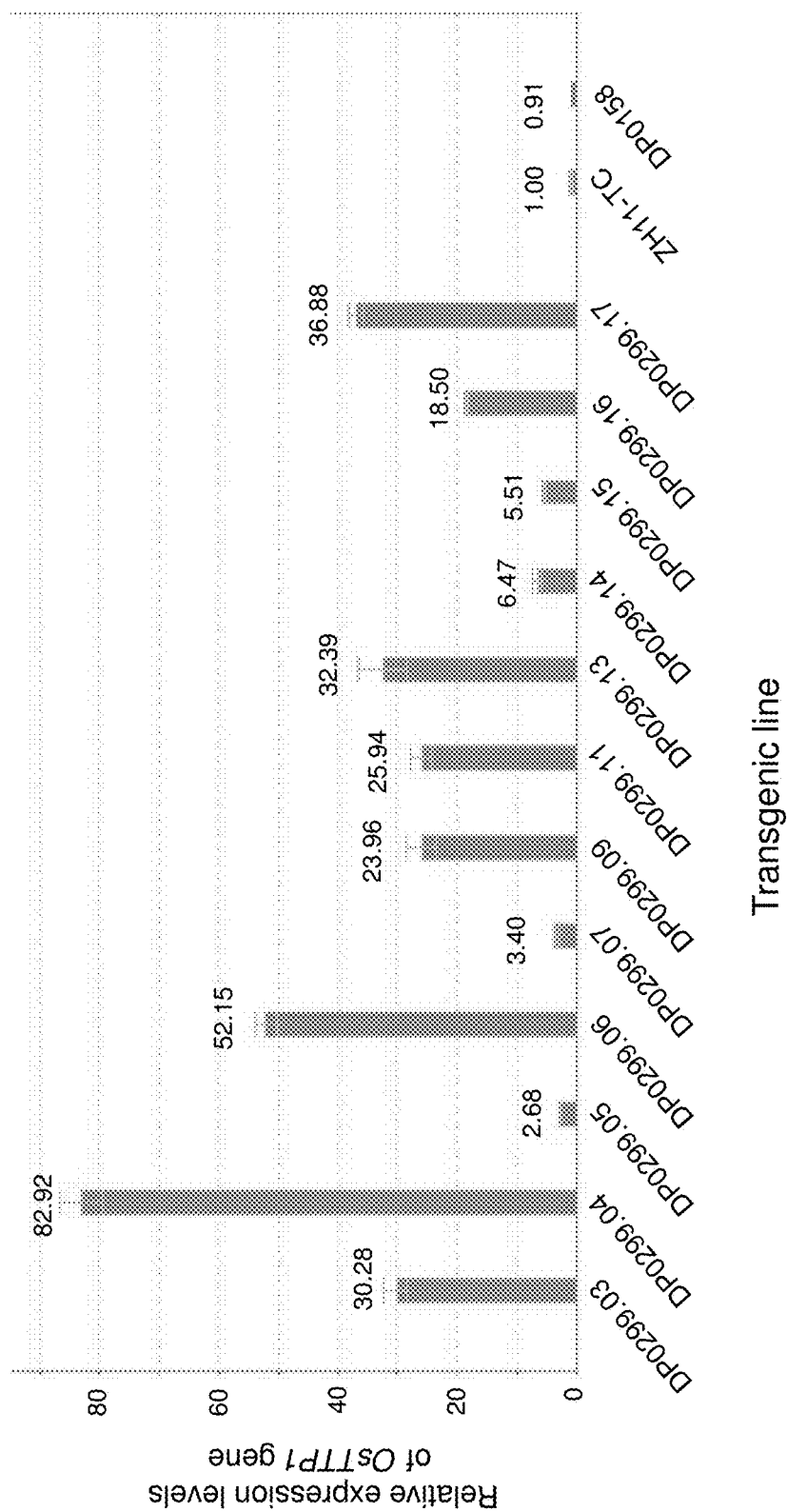
FIG. 7 shows the relative expression levels of OsTTP1 gene in leaves of different transgenic rice lines by real-time PCR analyses. The base expression level in ZH11-TC is set at 1.00, the numbers on the top of the columns are fold-changes compared to ZH11-TC rice.

As shown in FIG. 7, the expression level of OsTTP1 gene in ZH11-TC rice is set at 1.00, OsTTP1 over-expressed in all the transgenic lines. The expression levels of OsTTP1 were very low in both ZH11-TC and DP0158 plants.

```
DP0299-F1:
                                    (SEQ ID NO: 50)
5'-CATGGATTGTGCTGATTATTCC-3'

DP0299-R1:
                                    (SEQ ID NO: 51)
5'-CTCTTCTGTGACCGGTGAATC-3'
```

Example 4

Greenhouse NUE Assay of Transgenic Rice Plants

In order to investigate whether the genes could improve low nitrogen tolerance or nitrogen use efficiency (NUE) in rice plants, the transgenic rice plants were tested in greenhouse low nitrogen assays. In the greenhouse, two types of lamps are provided as light source, i.e. sodium lamp and metal halide lamp, the ratio is 1:1. Lamps provide the 16 h/8 h period of day/night, and are placed approximately 1.5 m above the seedbed. The light intensity 30 cm above the seedbed is measured as 10,000-20,000 lx in sunny day, while 6,000-10,000 lx in cloudy day, the relative humidity ranges from 30% to 90%, and the temperature ranges from 20 to 35° C.

NUE Test Method:

Transgenic $T_2$ seeds were sterilized by 800 ppm carbendazol for 8 h at 32° C. and washed 3-5 times, then soaked in water for 16 h at 32° C., germinated for 18 h at 35-37° C. in an incubator. The germinated seeds were selected and planted in pot filled with vermiculite. Randomized block design was used in this trait screen. Every screen unit has 4 blocks which include 2 controls (ZH11-TC and empty vector, or line null) and 4 transgenic lines. 8 seedlings of each transgenic line were planted in 4 pots and located in different positions of the 4 blocks. 9-12 transgenic lines of each gene were screened.

After cultured for 7-10 days, water was replaced by modified Hoagland solution containing 0.75 mM nitrogen ($KNO_3$) (Table 6). To make aerobic condition, the nutrition solution was drained off every Monday, Wednesday, and Friday for 2-3 h, and then new modified Hoagland containing low nitrogen solution was added. After cultured in low nitrogen solution for 35-40 days, tiller (including the stem and all tillers) numbers were counted, SPAD value was measured by a SPAD meter (SPAD 502 Plus, made by KONICA MINOLTA) with three different positions of the second leaf from the top, and the SPAD value was the average of three readings; and, the fresh weight of the seedlings (cutting from the joint of root and stem) was measured by one percent of the balance. After statistical analysis of these data (tiller number, SPAD value and fresh weight), the positive lines were selected by a cut-off of P<0.1.

TABLE 6

Modified Hoagland's nutrient solution for culturing rice

| Molecular formula | Mass concentration(g/L) |
|---|---|
| $KH_2PO_4$ | 34.38 |
| $MgSO_4 \cdot 7H_2O$ | 246.50 |
| $CaCl_2 \cdot 2H_2O$ | 146.88 |
| KCl | 242.29 |
| $KNO_3$ | 101.00 |
| $Na_2SiO_3 \cdot 9H_2O$ | 142.00 |
| $H_3BO_3$ | 1.85 |
| $MnCl_2 \cdot 4H_2O$ | 1.98 |
| $ZnSO_4 \cdot 7H_2O$ | 2.87 |
| $CuSO_4 \cdot 5H_2O$ | 0.25 |
| $(NH_4)_6MoO_{24} \cdot 2H_2O$ | 0.24 |
| EDTA—2Na | 7.45 |
| $FeSO_4 \cdot 7H_2O$ | 5.57 |

NUE Assay Results

1) GH NUE Validation Results of OsDN-LTP4 (DP0036) Transgenic Rice

For OsDN-LTP4 transgenic rice plants, 12 transgenic lines were tested and their line null were used as controls in the first experiment. As shown in Table 7, the average SPAD values of eight transgenic lines were greater than that of their corresponding controls and two of them had significantly higher average SPAD values. Six lines had higher average fresh weights and three lines had significantly higher fresh weights than the controls. Two lines had greater average SPAD values and fresh weights. These results indicate that OsDN-LTP4 transgenic rice grown better than their line null controls under low nitrogen conditions.

TABLE 7

Low nitrogen tolerance assay of OsDN-LTP4 transgenic rice plants under greenhouse low nitrogen conditions (1st experiment)

| | Tiller number | | | SPAD value | | | Fresh weight | | |
|---|---|---|---|---|---|---|---|---|---|
| Line ID | Average tiller number | P value | P ≤ 0.1 | Average SPAD value | P value | P ≤ 0.1 | Average fresh weight | P value | P ≤ 0.1 |
| DP0036.04 | 1.0 | 1.0000 | | 32.54 | 0.4171 | | 2.393 | 0.9245 | |
| DP0036.04-Null | 1.0 | | | 30.74 | | | 2.349 | | |
| DP0036.05 | 1.0 | 1.0000 | | 33.25 | 0.7803 | | 2.575 | 0.4324 | |
| DP0036.05-Null | 1.0 | | | 32.64 | | | 2.941 | | |
| DP0036.07 | 1.0 | 1.0000 | | 35.75 | 0.1601 | | 3.711 | 0.0195 | Y |
| DP0036.07-Null | 1.0 | | | 32.56 | | | 2.524 | | |
| DP0036.08 | 1.0 | 1.0000 | | 33.68 | 0.4354 | | 3.349 | 0.2968 | |
| DP0036.08-Null | 1.0 | | | 31.96 | | | 2.843 | | |
| DP0036.13 | 1.0 | 1.0000 | | 33.66 | 0.4386 | | 2.978 | 0.5205 | |
| DP0036.13-Null | 1.0 | | | 31.96 | | | 2.669 | | |
| DP0036.15 | 1.0 | 1.0000 | | 33.19 | 0.6294 | | 3.380 | 0.7208 | |
| DP0036.15-Null | 1.0 | | | 32.15 | | | 3.624 | | |
| DP0036.16 | 1.0 | 1.0000 | | 32.11 | 0.8157 | | 3.193 | 0.6239 | |
| DP0036.16-Null | 1.0 | | | 32.61 | | | 3.528 | | |
| DP0036.19 | 1.0 | 1.0000 | | 38.71 | 0.0224 | Y | 5.363 | 0.0033 | Y |
| DP0036.19-Null | 1.0 | | | 34.16 | | | 3.486 | | |
| DP0036.23 | 1.0 | 1.0000 | | 36.09 | 0.0427 | Y | 4.021 | 0.0427 | Y |
| DP0036.23-Null | 1.0 | | | 32.19 | | | 2.901 | | |

In the second experiment, ten lines were tested, ZH11-TC and DP0158 seedlings were used as controls, and randomized block design was used. Twelve rice plants from each transgenic line, ZH11-TC and DP0158 were planted in one container. When the rice plants grew to 3-leaf stage, Hoagland solution containing 0.75 mM potassium nitrate was applied to these plants. After low nitrogen stressed for 34 days, tiller number, SPAD value and fresh weight were measured. The average tiller number, SPAD value and fresh weight of all the OsDN-LTP4 transgenic rice were greater than both ZH11-TC and DP0158 controls at the construct level. The average SPAD value of OsDN-LTP4 transgenic rice was significantly greater than DP0158 control at the construct level.

As shown in Table 8, ten lines exhibited greater SPAD value, eight lines exhibited greater fresh weight than ZH11-TC control. As shown in Table 9, ten lines exhibited greater SPAD value, and eight lines exhibited greater fresh weight than DP0158 control. These results demonstrate OsDN-LTP4 transgenic rice obtained enhanced low nitrogen tolerance or improved NUE, and over-expression of OsDN-LTP4 enhances NUE of transgenic plants.

In the third experiment, the same ten lines were tested, and the experiment design and the treatment were same to that in the second experiment. After low nitrogen stressed for 34 days, tiller number, SPAD value and fresh weight were measured. The average SPAD value of the OsDN-LTP4 transgenic rice was more than that of ZH11-TC and DP0158 controls, and the average tiller number, and fresh weight were greater than DP0158 control at construct level.

As shown in Table 10, all the transgenic lines showed greater SPAD values than ZH11-TC control. All the ten lines showed greater tiller number, eight lines showed greater SPAD value, and nine lines showed greater fresh weight (Table 11). These results further indicates OsDN-LTP4 transgenic rice obtained enhanced low nitrogen tolerance or improved NUE, and OsDN-LTP4 plays a role in enhancing NUE of transgenic plants.

TABLE 8

Low nitrogen tolerance assay of OsDN-LTP4 transgenic rice plants under greenhouse low nitrogen conditions ($2^{nd}$ experiment, ZH11-TC as control)

| Line ID | Tiller number | | | SPAD value | | | Fresh weight | | |
| --- | --- | --- | --- | --- | --- | --- | --- | --- | --- |
| | Average tiller number | P value | P ≤ 0.05 | Average SPAD value | P value | P ≤ 0.05 | Average fresh weight | P value | P ≤ 0.05 |
| DP0036.05 | 1.6 | 0.2385 | | 35.15 | 0.1841 | | 3.225 | 0.3558 | |
| DP0036.07 | 1.2 | 0.9595 | | 35.13 | 0.2001 | | 2.950 | 0.9664 | |
| DP0036.08 | 1.4 | 0.4917 | | 35.12 | 0.1939 | | 3.132 | 0.5526 | |
| DP0036.11 | 1.5 | 0.3947 | | 36.11 | 0.0251 | Y | 3.416 | 0.1113 | |
| DP0036.13 | 1.8 | 0.0458 | Y | 36.12 | 0.0244 | Y | 3.574 | 0.0317 | Y |
| DP0036.15 | 1.4 | 0.4917 | | 35.59 | 0.0809 | | 3.604 | 0.0243 | Y |
| DP0036.16 | 1.4 | 0.4917 | | 35.06 | 0.2146 | | 3.224 | 0.3589 | |
| DP0036.17 | 1.3 | 0.9739 | | 34.46 | 0.5045 | | 2.870 | 0.7462 | |
| DP0036.19 | 1.5 | 0.3100 | | 35.85 | 0.0467 | Y | 3.351 | 0.1724 | |
| DP0036.23 | 1.3 | 0.7189 | | 35.43 | 0.1119 | | 3.522 | 0.0495 | Y |
| ZH11-TC | 1.3 | | | 33.77 | | | 2.963 | | |
| DP0036 (construct) | 1.4 | 0.3968 | | 35.40 | 0.0773 | | 3.287 | 0.1931 | |

TABLE 9

Low nitrogen tolerance assay of OsDN-LTP4 transgenic rice plants under greenhouse low nitrogen conditions ($2^{nd}$ experiment, DP0158 as control)

| Line ID | Tiller number | | | SPAD value | | | Fresh weight | | |
| --- | --- | --- | --- | --- | --- | --- | --- | --- | --- |
| | Average tiller number | P value | P ≤ 0.05 | Average SPAD value | P value | P ≤ 0.05 | Average fresh weight | P value | P ≤ 0.05 |
| DP0036.05 | 1.6 | 0.3888 | | 35.15 | 0.1327 | | 3.225 | 0.7377 | |
| DP0036.07 | 1.2 | 0.7173 | | 35.13 | 0.1459 | | 2.950 | 0.5384 | |
| DP0036.08 | 1.4 | 0.7109 | | 35.12 | 0.1403 | | 3.132 | 0.9958 | |
| DP0036.11 | 1.5 | 0.5932 | | 36.11 | 0.0157 | Y | 3.416 | 0.3156 | |
| DP0036.13 | 1.8 | 0.0929 | | 36.12 | 0.0153 | Y | 3.574 | 0.1187 | |
| DP0036.15 | 1.4 | 0.7109 | | 35.59 | 0.0547 | | 3.604 | 0.0961 | |
| DP0036.16 | 1.4 | 0.7109 | | 35.06 | 0.1566 | | 3.224 | 0.7422 | |
| DP0036.17 | 1.3 | 0.7762 | | 34.46 | 0.3993 | | 2.870 | 0.3617 | |
| DP0036.19 | 1.5 | 0.4850 | | 35.85 | 0.0304 | Y | 3.351 | 0.4378 | |
| DP0036.23 | 1.3 | 0.9657 | | 35.43 | 0.0776 | | 3.522 | 0.1688 | |
| DP0158 | 1.3 | | | 33.58 | | | 3.130 | | |
| DP0036 | 1.4 | 0.6265 | | 35.40 | 0.0495 | Y | 3.287 | 0.5293 | |

TABLE 10

Low nitrogen tolerance assay of OsDN-LTP4 transgenic rice plants under greenhouse low nitrogen conditions (3$^{rd}$ experiment, ZH11-TC as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0036.05 | 1.6 | 0.6643 | | 36.67 | 0.0569 | | 2.406 | 0.8567 | |
| DP0036.07 | 1.4 | 0.6967 | | 36.86 | 0.0356 | Y | 2.337 | 0.8314 | |
| DP0036.08 | 1.3 | 0.4228 | | 37.19 | 0.0149 | Y | 2.423 | 0.7813 | |
| DP0036.11 | 1.6 | 0.8196 | | 36.86 | 0.0356 | Y | 2.399 | 0.8885 | |
| DP0036.13 | 1.6 | 0.8196 | | 37.65 | 0.0036 | Y | 2.390 | 0.9308 | |
| DP0036.15 | 1.2 | 0.1558 | | 36.38 | 0.1087 | | 2.412 | 0.8314 | |
| DP0036.16 | 1.6 | 0.8196 | | 35.99 | 0.2292 | | 2.357 | 0.9217 | |
| DP0036.17 | 1.2 | 0.1558 | | 35.16 | 0.7319 | | 2.192 | 0.2998 | |
| DP0036.19 | 1.4 | 0.6967 | | 37.42 | 0.0075 | Y | 2.468 | 0.5939 | |
| DP0036.23 | 1.2 | 0.2249 | | 35.33 | 0.6005 | | 2.323 | 0.7726 | |
| ZH11-TC | 1.5 | | | 34.83 | | | 2.374 | | |
| DP0036 | 1.4 | 0.6051 | | 36.55 | 0.0417 | Y | 2.371 | 0.9817 | |

TABLE 11

Low nitrogen tolerance assay of OsDN-LTP4 transgenic rice plants under greenhouse low nitrogen conditions (3$^{rd}$ experiment, DP0158 as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0036.05 | 1.6 | 0.0299 | Y | 36.67 | 0.2339 | | 2.406 | 0.3223 | |
| DP0036.07 | 1.4 | 0.1779 | | 36.86 | 0.1650 | | 2.337 | 0.5510 | |
| DP0036.08 | 1.3 | 0.3495 | | 37.19 | 0.0850 | | 2.423 | 0.2771 | |
| DP0036.11 | 1.6 | 0.0494 | Y | 36.86 | 0.1650 | | 2.399 | 0.3424 | |
| DP0036.13 | 1.6 | 0.0494 | Y | 37.65 | 0.0280 | Y | 2.390 | 0.3702 | |
| DP0036.15 | 1.2 | 0.7507 | | 36.38 | 0.3731 | | 2.412 | 0.3067 | |
| DP0036.16 | 1.6 | 0.0494 | Y | 35.99 | 0.6248 | | 2.357 | 0.4771 | |
| DP0036.17 | 1.2 | 0.7507 | | 35.16 | 0.7108 | | 2.192 | 0.8199 | |
| DP0036.19 | 1.4 | 0.1779 | | 37.42 | 0.0500 | | 2.468 | 0.1795 | |
| DP0036.23 | 1.2 | 0.6006 | | 35.33 | 0.8495 | | 2.323 | 0.6030 | |
| DP0158 | 1.1 | | | 35.52 | | | 2.232 | | |
| DP0036 | 1.4 | 0.1409 | | 36.55 | 0.2223 | | 2.371 | 0.3773 | |

2) GH NUE Validation Results of OsDN-LTP6 (DP0046) Transgenic Rice

Twelve OsDN-LTP6 transgenic lines were tested and used the corresponding line null as their controls in the first experiment. As shown in Table 12, six transgenic lines had greater/equal average tiller numbers, SPAD values and fresh weights than their corresponding controls after cultured in 0.75 mM nitrogen solution for 42 days. Three OsDN-LTP6 transgenic lines (DP0046.01, DP0046.04 and DP0046.19) showed significantly greater average SPAD values and two lines (DP0046.04 and DP0046.19) showed significantly greater average fresh weights than their corresponding controls. These results demonstrate that the OsDN-LTP6 transgenic rice plants had enhanced low nitrogen tolerance or improved NUE at seedling stage.

In the second experiment, 11 transgenic lines were tested and DP0005 and ZH11-TC seedlings were used as controls. As shown in Table 13, three transgenic lines had higher average tiller number, SPAD values and fresh weights than ZH11-TC seedlings, and DP0046.13 showed significantly higher of three parameters than ZH11-TC control at the level of P<0.1. The fresh weights of two transgenic lines were greater than that of ZH11-TC controls, and four transgenic lines had significantly greater fresh weight than DP0005 control. And most of the transgenic lines (ten lines) had higher average SPAD values than their DP0005 controls. These results demonstrate that the OsDN-LTP6 transgenic rice plants showed enhanced low nitrogen tolerance or NUE. Over-expression of OsDN-LTP6 improved low nitrogen tolerance or NUE of transgenic rice plants.

TABLE 12

Low nitrogen tolerance assay of OsDN-LTP6 transgenic rice plants
under greenhouse low nitrogen conditions (1st experiment)

| Line ID | Tiller number Average tiller number | P value | P ≤ 0.1 | SPAD value Average SPAD value | P value | P ≤ 0.1 | Fresh weight Average fresh weight | P value | P ≤ 0.1 |
|---|---|---|---|---|---|---|---|---|---|
| DP0046.01 | 1.1 | 0.2365 | | 32.73 | 0.0563 | Y | 3.494 | 0.1196 | |
| DP0046.01-Null | 1.0 | | | 29.06 | | | 2.674 | | |
| DP0046.03 | 1.0 | 1.0000 | | 33.63 | 0.6388 | | 4.083 | 0.2275 | |
| DP0046.03-Null | 1.0 | | | 32.81 | | | 3.465 | | |
| DP0046.04 | 1.0 | 0.2365 | | 35.99 | 0.0220 | Y | 4.968 | 0.0055 | Y |
| DP0046.04-Null | 1.1 | | | 31.36 | | | 3.240 | | |
| DP0046.06 | 1.3 | 0.1173 | | 32.08 | 0.2074 | | 2.824 | 0.5026 | |
| DP0046.06-Null | 1.0 | | | 28.71 | | | 2.334 | | |
| DP0046.13 | 1.0 | 1.0000 | | 31.94 | 0.6553 | | 3.198 | 0.6417 | |
| DP0046.13-Null | 1.0 | | | 33.10 | | | 2.859 | | |
| DP0046.19 | 1.3 | 0.1173 | | 31.46 | 0.0875 | Y | 3.559 | 0.0746 | Y |
| DP0046.19-Null | 1.0 | | | 25.74 | | | 2.201 | | |
| DP0046.23 | 1.0 | 1.0000 | | 25.75 | 0.6667 | | 2.288 | 0.5481 | |
| DP0046.23-Null | 1.0 | | | 23.88 | | | 1.755 | | |
| DP0046.24 | 1.0 | 1.0000 | | 32.62 | 0.4418 | | 3.878 | 0.2037 | |
| DP0046.24-Null | 1.0 | | | 28.85 | | | 2.638 | | |
| DP0046.27 | 1.0 | 1.0000 | | 25.83 | 0.6321 | | 1.688 | 0.7448 | |
| DP0046.27-Null | 1.0 | | | 23.74 | | | 1.975 | | |

TABLE 13

Low nitrogen tolerance assay of OsDN-LTP6 transgenic rice plants
under greenhouse low nitrogen conditions (2nd experiment)

| Line ID | Tiller number Average tiller number | P value | P ≤ 0.1 | SPAD value Average SPAD value | P value | P ≤ 0.1 | Fresh weight Average fresh weight | P value | P ≤ 0.1 |
|---|---|---|---|---|---|---|---|---|---|
| DP0046.04 | 1.6 | 1.0000 | | 34.36 | 0.1838 | | 4.513 | 0.8669 | |
| ZH11-TC | 1.6 | | | 31.90 | | | 4.601 | | |
| DP0046.13 | 2.3 | 0.0612 | Y | 38.09 | 0.0465 | Y | 6.013 | 0.0006 | Y |
| ZH11-TC | 1.3 | | | 35.43 | | | 4.149 | | |
| DP0046.15 | 2.3 | 0.1440 | | 35.28 | 0.8250 | | 5.986 | 0.8747 | |
| ZH11-TC | 1.4 | | | 35.00 | | | 5.876 | | |
| DP0046.17 | 1.8 | 0.5245 | | 34.43 | 0.7005 | | 5.313 | 0.2740 | |
| ZH11-TC | 1.5 | | | 33.91 | | | 4.481 | | |
| DP0046.19 | 1.4 | 0.7491 | | 35.19 | 0.3437 | | 5.483 | 0.1909 | |
| ZH11-TC | 1.5 | | | 33.91 | | | 4.481 | | |
| DP0046.24 | 1.3 | 0.4825 | | 38.11 | 0.4594 | | 5.431 | 0.0965 | Y |
| ZH11-TC | 1.5 | | | 36.48 | | | 4.339 | | |
| DP0046.27 | 1.6 | 0.7241 | | 37.89 | 0.5223 | | 5.133 | 0.2189 | |
| ZH11-TC | 1.5 | | | 36.48 | | | 4.339 | | |

In the third experiment, ten lines were tested, ZH11-TC and DP0158 seedlings were used as controls, and randomized block design was used. Twelve rice plants from each transgenic line, ZH11-TC and DP0158 were planted in one container, repeated twice. When the rice plants grew to 3-leaf stage, Hoagland solution containing 0.75 mM potassium nitrate was applied to these plants. After low nitrogen stressed for 36 days, tiller number, SPAD value and fresh weight were measured. The average SPAD value of OsDN-LTP6 transgenic rice was significantly greater than that of ZH11-TC (P value=0.0275) and greater than that of DP0158 (P value=0.0943) control; and the average fresh weight of OsDN-LTP6 transgenic rice was greater than that of ZH11-TC and DP0158 at construct level.

As shown in Table 14 and 15, ten lines exhibited greater SPAD value than ZH11-TC and DP0158; and nine lines exhibited greater fresh weight than ZH11-TC control, and seven lines exhibited greater fresh weight than DP0158 control. These results further demonstrate OsDN-LTP6 transgenic rice obtained enhanced low nitrogen tolerance or improved NUE, and over-expression of OsDN-LTP6 enhances NUE of transgenic plants.

TABLE 14

Low nitrogen tolerance assay of OsDN-LTP6 transgenic rice plants under greenhouse low nitrogen conditions (3rd experiment, ZH11-TC as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0046.01 | 1.0 | 0.4751 | | 31.46 | 0.2854 | | 3.785 | 0.8531 | |
| DP0046.03 | 1.0 | 0.4751 | | 32.98 | 0.0080 | Y | 4.443 | 0.0194 | Y |
| DP0046.04 | 1.0 | 0.4751 | | 32.78 | 0.0145 | Y | 4.557 | 0.0067 | Y |
| DP0046.06 | 1.0 | 0.4751 | | 32.05 | 0.0930 | | 3.422 | 0.3164 | |
| DP0046.13 | 1.0 | 0.4751 | | 32.87 | 0.0113 | Y | 4.422 | 0.0234 | Y |
| DP0046.17 | 1.0 | 0.4751 | | 32.40 | 0.0408 | Y | 4.457 | 0.0172 | Y |
| DP0046.19 | 1.0 | 0.4751 | | 31.84 | 0.1444 | | 4.344 | 0.0441 | Y |
| DP0046.23 | 1.0 | 0.4751 | | 31.38 | 0.3219 | | 3.915 | 0.5414 | |
| DP0046.27 | 1.0 | 0.4751 | | 33.41 | 0.0019 | Y | 4.283 | 0.0697 | |
| DP0046.28 | 1.0 | 0.4751 | | 31.66 | 0.2012 | | 3.752 | 0.9387 | |
| ZH11-TC | 1.0 | | | 30.43 | | | 3.729 | | |
| DP0046 (construct) | 1.0 | 0.4751 | | 32.28 | 0.0275 | Y | 4.138 | 0.1372 | |

TABLE 15

Low nitrogen tolerance assay of OsDN-LTP6 transgenic rice plants under greenhouse low nitrogen conditions (3rd experiment, DP0158 as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0046.01 | 1.0 | 0.4751 | | 31.46 | 0.5458 | | 3.785 | 0.9757 | |
| DP0046.03 | 1.0 | 0.4751 | | 32.98 | 0.0287 | Y | 4.443 | 0.0339 | Y |
| DP0046.04 | 1.0 | 0.4751 | | 32.78 | 0.0477 | Y | 4.557 | 0.0126 | Y |
| DP0046.06 | 1.0 | 0.4751 | | 32.05 | 0.2242 | | 3.422 | 0.2234 | |
| DP0046.13 | 1.0 | 0.4751 | | 32.87 | 0.0384 | Y | 4.422 | 0.0402 | Y |
| DP0046.17 | 1.0 | 0.4751 | | 32.40 | 0.1139 | | 4.457 | 0.0302 | Y |
| DP0046.19 | 1.0 | 0.4751 | | 31.84 | 0.3196 | | 4.344 | 0.0722 | |
| DP0046.23 | 1.0 | 0.4751 | | 31.38 | 0.5987 | | 3.915 | 0.6927 | |
| DP0046.27 | 1.0 | 0.4751 | | 33.41 | 0.0084 | Y | 4.283 | 0.1100 | |
| DP0046.28 | 1.0 | 0.4751 | | 31.66 | 0.4157 | | 3.752 | 0.8897 | |
| DP0158 | 1.0 | | | 30.88 | | | 3.795 | | |
| DP0046 (construct) | 1.0 | 0.4751 | | 32.28 | 0.0943 | | 4.138 | 0.2124 | |

3) GH NUE Validation Results of OsDN-LTP7 (DP0063) Transgenic Rice

Nine OsDN-LTP7 transgenic lines were tested and used the corresponding line null as their controls in the first experiment. As shown in Table 16, four transgenic lines had greater average tiller numbers, eight lines had greater average SPAD values than their corresponding controls after cultured in 0.75 mM nitrogen solution for 41 days. Four lines showed significantly greater average SPAD values than their corresponding controls. These results demonstrate that the OsDN-LTP7 transgenic rice plants had enhanced low nitrogen tolerance or improved NUE at seedling stage.

In the second experiment, 11 transgenic lines were tested and DP0005 and ZH11-TC seedlings were used as controls. As shown in Table 17, nine transgenic lines had higher average SPAD values and fresh weights than DP0005 seedlings. Two lines exhibited significantly higher SPAD values and three lines exhibited significantly higher fresh weights than DP0005 controls at the level of P value 0.1. When compared to ZH11-TC controls, ten lines showed higher SPAD values and eight lines showed higher fresh weights. These results demonstrate that the OsDN-LTP7 transgenic rice plants showed enhanced low nitrogen tolerance or NUE.

TABLE 16

Low nitrogen tolerance assay of OsDN-LTP7 transgenic rice plants under greenhouse low nitrogen conditions (1$^{st}$ experiment)

| | Tiller number | | | SPAD value | | | Fresh weight | | |
|---|---|---|---|---|---|---|---|---|---|
| Line ID | Average tiller number | P value | P ≤ 0.1 | Average SPAD value | P value | P ≤ 0.1 | Average fresh weight | P value | P ≤ 0.1 |
| DP0063.01 | 1.2 | 0.2829 | | 40.97 | 0.1037 | | 5.427 | 0.5850 | |
| DP0063.01-Null | 1.0 | | | 38.39 | | | 5.138 | | |
| DP0063.02 | 1.4 | 0.1705 | | 39.16 | 0.0413 | Y | 5.991 | 0.9439 | |
| DP0063.02-Null | 1.1 | | | 35.96 | | | 6.020 | | |
| DP0063.04 | 1.3 | 0.3035 | | 38.65 | 0.2041 | | 5.648 | 0.7156 | |
| DP0063.04-Null | 1.1 | | | 33.41 | | | 5.459 | | |
| DP0063.06 | 1.0 | 1.0000 | | 35.15 | 0.9104 | | 4.527 | 0.3287 | |
| DP0063.06-Null | 1.0 | | | 35.36 | | | 5.152 | | |
| DP0063.08 | 1.0 | 1.0000 | | 38.19 | 0.0303 | Y | 6.287 | 0.5547 | |
| DP0063.08-Null | 1.0 | | | 35.21 | | | 5.724 | | |
| DP0063.09 | 1.3 | 0.6349 | | 41.25 | 0.0042 | Y | 5.498 | 0.4510 | |
| DP0063.09-Null | 1.1 | | | 37.93 | | | 5.742 | | |
| DP0063.13 | 1.0 | 0.1705 | | 36.10 | 0.0382 | Y | 4.787 | 0.7385 | |
| DP0063.13-Null | 1.3 | | | 33.26 | | | 4.599 | | |
| DP0063.15 | 1.0 | 0.3861 | | 34.18 | 0.7264 | | 4.390 | 0.2599 | |
| DP0063.15-Null | 1.1 | | | 33.59 | | | 4.756 | | |

TABLE 17

Low nitrogen tolerance assay of OsDN-LTP7 transgenic rice plants under greenhouse low nitrogen conditions (2$^{nd}$ experiment)

| | Tiller number | | | SPAD value | | | Fresh weight | | |
|---|---|---|---|---|---|---|---|---|---|
| Line ID | Average tiller number | P value | P ≤ 0.1 | Average SPAD value | P value | P ≤ 0.1 | Average fresh weight | P value | P ≤ 0.1 |
| DP0063.01 | 1.1 | 1.0000 | | 42.98 | 0.1045 | | 5.685 | 0.0295 | Y |
| DP0005 | 1.1 | | | 39.65 | | | 4.043 | | |
| DP0063.02 | 1.6 | 0.0123 | Y | 41.08 | 0.9121 | | 4.731 | 0.6367 | |
| DP0005 | 1.0 | | | 41.34 | | | 4.460 | | |
| DP0063.04 | 1.1 | 1.0000 | | 38.36 | 0.0102 | Y | 3.925 | 0.1562 | |
| DP0005 | 1.1 | | | 35.04 | | | 3.320 | | |
| DP0063.05 | 1.3 | 0.7241 | | 38.70 | 0.3760 | | 4.443 | 0.7337 | |
| DP0005 | 1.4 | | | 37.44 | | | 4.265 | | |
| DP0063.06 | 1.1 | 1.0000 | | 43.99 | 0.2887 | | 5.030 | 0.1446 | |
| DP0005 | 1.1 | | | 41.44 | | | 4.133 | | |
| DP0063.08 | 1.6 | 0.0036 | Y | 41.38 | 0.0988 | Y | 4.853 | 0.0086 | Y |
| DP0005 | 1.0 | | | 37.86 | | | 3.311 | | |
| DP0063.10 | 1.0 | 1.0000 | | 35.90 | 0.7433 | | 4.116 | 0.2200 | |
| DP0005 | 1.0 | | | 35.23 | | | 3.346 | | |
| DP0063.11 | 1.0 | 1.0000 | | 38.43 | 0.2878 | | 4.121 | 0.1507 | |
| DP0005 | 1.0 | | | 37.09 | | | 3.475 | | |
| DP0063.13 | 1.0 | 1.0000 | | 37.74 | 0.9718 | | 3.970 | 0.0849 | Y |
| DP0005 | 1.0 | | | 37.69 | | | 3.295 | | |
| DP0063.16 | 1.0 | 1.0000 | | 37.44 | 0.3328 | | 4.025 | 0.4876 | |
| DP0005 | 1.0 | | | 35.48 | | | 3.741 | | |

In the third experiment, ten lines were tested, ZH11-TC and DP0158 seedlings were used as controls, and randomized block design was used. Twelve rice plants from each transgenic line, ZH11-TC and DP0158 were planted in one container, repeated twice. When the rice plants grew to 3-leaf stage, Hoagland solution containing 0.75 mM potassium nitrate was applied to these plants. After low nitrogen stressed for 36 days, tiller number, SPAD value and fresh weight were measured. The average SPAD value of OsDN-LTP7 transgenic rice was significantly greater than that of ZH11-TC; and the average fresh weight of OsDN-LTP7 transgenic rice was greater than that of ZH11-TC control at construct level. The average tiller number, SPAD value and fresh weight of the transgenic rice were equal to that of DP0158 control.

As shown in Table 18, ten lines exhibited greater tiller numbers and greater SPAD values than ZH11-TC control, and six lines exhibited greater fresh weights than ZH11-TC control. These results demonstrate OsDN-LTP7 transgenic rice obtained enhanced low nitrogen tolerance or improved NUE than ZH11-TC control, and over-expression of OsDN-LTP7 enhances NUE of transgenic plants.

TABLE 18

Low nitrogen tolerance assay of OsDN-LTP7 transgenic rice plants under greenhouse low nitrogen conditions (3rd experiment, ZH11-TC as control)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0063.01 | 1.1 | 0.1919 | | 36.15 | 0.0277 | Y | 3.212 | 0.1907 | |
| DP0063.02 | 1.2 | 0.1127 | | 36.08 | 0.0331 | Y | 3.071 | 0.4647 | |
| DP0063.04 | 1.1 | 0.3063 | | 36.08 | 0.0335 | Y | 2.934 | 0.8645 | |
| DP0063.05 | 1.1 | 0.2446 | | 36.13 | 0.0289 | Y | 2.859 | 0.8900 | |
| DP0063.06 | 1.1 | 0.4588 | | 36.07 | 0.0343 | Y | 2.712 | 0.4602 | |
| DP0063.08 | 1.1 | 0.3776 | | 35.92 | 0.0510 | | 2.581 | 0.2019 | |
| DP0063.10 | 1.2 | 0.0617 | | 36.19 | 0.0247 | Y | 3.539 | 0.0082 | Y |
| DP0063.13 | 1.1 | 0.1919 | | 36.14 | 0.0283 | Y | 3.097 | 0.4027 | |
| DP0063.15 | 1.1 | 0.4544 | | 36.16 | 0.0265 | Y | 2.819 | 0.7678 | |
| DP0063.16 | 1.1 | 0.3776 | | 36.08 | 0.0330 | Y | 2.996 | 0.6719 | |
| ZH11-TC | 1.0 | | | 34.14 | | | 2.893 | | |
| DP0158 | 1.1 | | | 36.09 | | | 3.246 | | |
| DP0063 (construct) | 1.1 | 0.2019 | | 36.10 | 0.0267 | Y | 2.982 | 0.6798 | |

In the fourth experiment, the same ten lines were tested, and the experiment design and the treatment were same to that in the second experiment. The rice plants were stressed in low nitrogen solution for 35 days. The average SPAD value and fresh weight of the OsDN-LTP7 transgenic rice were more than that of ZH11-TC control at construct level. The SPAD value was significantly greater than ZH11-TC control; and the tiller number SPAD value and fresh weight were almost the same as that of DP0158 seedlings. As shown in Table 19, all the transgenic lines showed greater SPAD value and fresh weights than ZH11-TC control. These results demonstrate OsDN-LTP7 transgenic rice obtained enhanced low nitrogen tolerance or improved NUE, and OsDN-LTP7 plays a role in enhancing NUE of transgenic plants.

TABLE 19

Low nitrogen tolerance assay of OsDN-LTP7 transgenic rice plants under greenhouse low nitrogen conditions (4th experiment, ZH11-TC as control)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0063.01 | 1.1 | 0.7145 | | 34.59 | 0.0037 | Y | 4.040 | 0.5151 | |
| DP0063.02 | 1.2 | 0.9253 | | 34.44 | 0.0053 | Y | 4.040 | 0.5152 | |
| DP0063.04 | 1.2 | 0.9697 | | 34.68 | 0.0029 | Y | 4.040 | 0.5152 | |
| DP0063.05 | 1.1 | 0.8658 | | 33.96 | 0.0164 | Y | 4.039 | 0.5164 | |
| DP0063.06 | 1.1 | 0.8658 | | 34.78 | 0.0022 | Y | 4.041 | 0.5142 | |
| DP0063.08 | 1.1 | 0.8149 | | 34.46 | 0.0051 | Y | 4.040 | 0.5152 | |
| DP0063.10 | 1.2 | 0.9179 | | 34.33 | 0.0069 | Y | 4.040 | 0.5147 | |
| DP0063.13 | 1.1 | 0.7642 | | 34.27 | 0.0082 | Y | 4.040 | 0.5156 | |
| DP0063.15 | 1.2 | 0.7719 | | 34.55 | 0.0041 | Y | 4.040 | 0.5147 | |
| DP0063.16 | 1.1 | 0.7642 | | 34.52 | 0.0044 | Y | 4.040 | 0.5147 | |
| ZH11-TC | 1.2 | | | 30.98 | | | 3.798 | | |
| DP0158 | 1.3 | | | 33.70 | | | 4.320 | | |
| DP0063 (construct) | 1.2 | 0.8901 | | 34.46 | 0.0029 | Y | 4.040 | 0.5149 | |

4) GH NUE Validation Results of OsBAK1L (DP0066) Transgenic Rice

For OsBAK1L transgenic rice, six transgenic lines were tested using their corresponding line null as controls in the first experiment. As shown in Table 20, the average tiller numbers of all the six transgenic lines were greater than/equal to that of their corresponding line null, two lines (DP0066.03 and DP0066.10) had significantly greater average SPAD values and two lines (DP0066.09 and DP0066.10) had significantly greater average fresh weights than their corresponding controls, respectively. These results show that the OsBAK1L transgenic rice had enhanced low nitrogen tolerance or improved NUE at seedling stage.

Ten OsBAK1L transgenic lines were tested in the second experiment, and the ZH11-TC and DP0158 seedlings were used as controls. As shown in Table 21, the average fresh weights of ten lines were higher than that of DP0158 controls and 3 lines showed significantly higher average fresh weights. For the parameters of average tiller number and SPAD value, most of the lines were greater than DP0158 seedlings, and three lines (DP0066.01, DP0066.04 and DP0066.15) showed significantly higher average tiller numbers than both controls of ZH11-TC and DP0158. These results further demonstrate that the OsBAK1L transgenic rice plants showed enhanced low nitrogen tolerance or NUE. Over-expression of OsBAK1L gene improves the low nitrogen tolerance or NUE of transgenic rice plants.

TABLE 20

Low nitrogen tolerance assay of OsBAK1L transgenic rice plants under greenhouse low nitrogen conditions (1st experiment)

| Line ID | Tiller number Average tiller number | P value | P ≤ 0.1 | SPAD value Average SPAD value | P value | P ≤ 0.1 | Fresh weight Average fresh weight | P value | P ≤ 0.1 |
|---|---|---|---|---|---|---|---|---|---|
| DP0066.01 | 1.2 | 1.0000 | | 32.94 | 0.7475 | | 2.538 | 0.3344 | |
| DP0066.01-Null | 1.2 | | | 33.51 | | | 3.139 | | |
| DP0066.02 | 1.0 | 1.0000 | | 24.44 | 0.6654 | | 2.441 | 0.9145 | |
| DP0066.02-Null | 1.0 | | | 23.33 | | | 2.390 | | |
| DP0066.03 | 1.4 | 0.1898 | | 32.95 | 0.0951 | Y | 2.511 | 0.9865 | |
| DP0066.03-Null | 1.1 | | | 27.75 | | | 2.523 | | |
| DP0066.09 | 1.3 | 0.3048 | | 38.51 | 0.2003 | | 4.571 | 0.0299 | Y |
| DP0066.09-Null | 1.0 | | | 32.36 | | | 2.366 | | |
| DP0066.10 | 1.0 | 1.0000 | | 32.34 | 0.0415 | Y | 3.289 | 0.0352 | Y |
| DP0066.10-Null | 1.0 | | | 25.15 | | | 2.004 | | |
| DP0066.13 | 1.0 | 1.0000 | | 25.29 | 0.6377 | | 2.380 | 0.4988 | |
| DP0066.13-Null | 1.0 | | | 26.13 | | | 1.992 | | |

TABLE 21

Low nitrogen tolerance assay of OsBAK1L transgenic rice plants under greenhouse low nitrogen conditions (2nd experiment)

| Line ID | Tiller number Average tiller number | P value | P ≤ 0.1 | SPAD value Average SPAD value | P value | P ≤ 0.1 | Fresh weight Average fresh weight | P value | P ≤ 0.1 |
|---|---|---|---|---|---|---|---|---|---|
| DP0066.01 | 3.3 | 0.0003 | Y | 37.53 | 0.1369 | | 6.213 | 0.0828 | Y |
| DP0158 | 1.5 | | | 34.11 | | | 4.543 | | |
| DP0066.03 | 1.9 | 0.1313 | | 37.55 | 0.8365 | | 5.411 | 0.7806 | |
| DP0158 | 1.3 | | | 37.80 | | | 5.208 | | |
| DP0066.04 | 2.0 | 0.0222 | Y | 39.68 | 0.3412 | | 5.929 | 0.4160 | |
| DP0158 | 1.1 | | | 38.33 | | | 5.513 | | |
| DP0066.05 | 1.6 | 0.1479 | | 40.95 | 0.1010 | | 6.078 | 0.0561 | Y |
| DP0158 | 1.1 | | | 38.15 | | | 4.546 | | |
| DP0066.06 | 1.4 | 0.2954 | | 34.64 | 0.9751 | | 4.064 | 0.4357 | |
| DP0158 | 1.1 | | | 34.68 | | | 3.656 | | |
| DP0066.08 | 1.0 | 0.7146 | | 35.43 | 0.3712 | | 5.736 | 0.1191 | |
| DP0158 | 1.1 | | | 34.14 | | | 4.584 | | |
| DP0066.12 | 1.4 | 0.1568 | | 36.93 | 0.1276 | | 5.954 | 0.0578 | Y |
| DP0158 | 1.1 | | | 34.41 | | | 4.646 | | |
| DP0066.14 | 1.0 | 1.0000 | | 36.36 | 0.6263 | | 5.248 | 0.9395 | |
| DP0158 | 1.0 | | | 35.54 | | | 5.198 | | |
| DP0066.15 | 1.4 | 0.0228 | Y | 37.55 | 0.9962 | | 5.830 | 0.5506 | |
| DP0158 | 1.1 | | | 37.56 | | | 5.318 | | |

In the third experiment, ten lines were tested, ZH11-TC and DP0158 seedlings were used as controls, and randomized block design was used. Twelve rice plants from each transgenic line, ZH11-TC and DP0158 were planted in one container. When the rice plants grew to 3-leaf stage, Hoagland solution containing 0.75 mM potassium nitrate was applied to these plants for 32 days. The average tiller number, SPAD value and fresh weight of OsBAK1L transgenic rice was greater than that of ZH11-TC control; and the average tiller number was significantly greater than that of DP0158 control at the construct level. As shown in Table 22, ten lines exhibited greater SPAD values, and nine lines exhibited greater fresh weights than ZH11-TC control. These results demonstrate OsBAK1L transgenic rice obtained enhanced low nitrogen tolerance or improved NUE than ZH11-TC control, and over-expression of OsBAK1L enhances NUE of transgenic plants.

TABLE 22

Low nitrogen tolerance assay of OsBAK1L transgenic rice plants under greenhouse low nitrogen conditions (3$^{rd}$ experiment, ZH11-TC as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0066.01 | 1.6 | 0.8053 | | 32.83 | 0.0166 | Y | 3.400 | 0.6235 | |
| DP0066.03 | 1.6 | 0.8053 | | 33.80 | 0.0018 | Y | 3.434 | 0.5551 | |
| DP0066.04 | 1.6 | 0.8053 | | 32.94 | 0.0132 | Y | 3.237 | 0.9808 | |
| DP0066.05 | 1.6 | 0.8053 | | 33.39 | 0.0049 | Y | 3.397 | 0.6279 | |
| DP0066.06 | 1.6 | 0.8053 | | 32.75 | 0.0197 | Y | 3.331 | 0.7681 | |
| DP0066.07 | 1.6 | 0.8053 | | 31.69 | 0.1238 | | 3.216 | 0.9725 | |
| DP0066.08 | 1.6 | 0.8053 | | 32.70 | 0.0215 | Y | 3.539 | 0.3737 | |
| DP0066.12 | 1.6 | 0.8053 | | 32.46 | 0.0343 | Y | 3.451 | 0.5240 | |
| DP0066.14 | 1.6 | 0.8053 | | 33.42 | 0.0045 | Y | 3.245 | 0.9613 | |
| DP0066.15 | 1.6 | 0.8053 | | 32.94 | 0.0133 | Y | 3.533 | 0.3830 | |
| ZH11-TC | 1.5 | | | 29.65 | | | 3.228 | | |
| DP0158 | 1.0 | | | 33.03 | | | 3.497 | | |
| DP0066 (construct) | 1.6 | 0.8053 | | 32.89 | 0.0062 | Y | 3.378 | 0.6358 | |

In the fourth experiment, the same ten lines were tested, and the experiment design and the treatment were same to that in the second experiment. The rice plants were low nitrogen stressed for 36 days. The average tiller number, SPAD value and fresh weight of the OsBAK1L transgenic rice were more than that of ZH11-TC control at construct level. As shown in Table 23, all the transgenic lines showed greater SPAD value and fresh weights than either ZH11-TC control. These results also demonstrate OsBAK1L transgenic rice obtained enhanced low nitrogen tolerance or improved NUE, and OsBAK1L plays a role in enhancing NUE of transgenic plants.

TABLE 23

Low nitrogen tolerance assay of OsBAK1L transgenic rice plants under greenhouse low nitrogen conditions (4$^{th}$ experiment, ZH11-TC as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0066.01 | 1.2 | 0.0103 | Y | 33.57 | 0.0009 | Y | 4.126 | 0.1516 | |
| DP0066.03 | 1.1 | 0.1416 | | 33.57 | 0.0009 | Y | 4.188 | 0.1211 | |
| DP0066.04 | 1.1 | 0.3569 | | 33.57 | 0.0009 | Y | 4.249 | 0.0955 | |
| DP0066.05 | 1.1 | 0.3569 | | 33.57 | 0.0009 | Y | 4.260 | 0.0915 | |
| DP0066.06 | 1.0 | 0.7094 | | 33.57 | 0.0009 | Y | 4.235 | 0.1011 | |
| DP0066.07 | 1.0 | 0.7094 | | 33.57 | 0.0009 | Y | 4.210 | 0.1114 | |
| DP0066.08 | 1.0 | 0.7094 | | 33.57 | 0.0009 | Y | 4.236 | 0.1005 | |
| DP0066.12 | 1.1 | 0.1416 | | 33.57 | 0.0009 | Y | 4.233 | 0.1017 | |
| DP0066.14 | 1.0 | 0.7094 | | 33.57 | 0.0009 | Y | 3.783 | 0.4344 | |
| DP0066.15 | 1.0 | 0.7094 | | 33.57 | 0.0009 | Y | 4.328 | 0.0694 | |
| ZH11-TC | 1.0 | | | 29.02 | | | 3.372 | | |
| DP0158 | 1.1 | | | 34.04 | | | 4.388 | | |
| DP0066 (construct) | 1.1 | 0.2914 | | 33.57 | 0.0009 | Y | 4.185 | 0.0923 | |

5) GH NUE Validation Results of OsEIL2 (DP0069) Transgenic Rice

In the second experiment, ten lines were tested, ZH11-TC and DP0158 seedlings were used as controls, and randomized block design was used. Twelve rice plants from each transgenic line, ZH11-TC and DP0158 were planted in one container, repeated twice. When the rice plants grew to 3-leaf stage, Hoagland solution containing 0.75 mM potassium nitrate was applied to these plants for 31 days. The OsEIL2 transgenic rice exhibited greater average SPAD value and fresh weight than either ZH11-TC or DP0158 control at the construct level, the SPAD value and fresh weight of OsEIL2 transgenic rice were significantly greater than ZH11-TC control.

As shown in Table 24 and 25, ten lines exhibited greater SPAD value than ZH11-TC control; and seven lines exhibited greater SPAD value than DP0158 control. These results indicate that OsEIL2 transgenic rice plants have enhanced low nitrogen tolerance or improved NUE, and over-expression of OsLRP1 enhances NUE of transgenic plants.

TABLE 24

Low nitrogen tolerance assay of OsEIL2 transgenic rice plants under greenhouse low nitrogen conditions (1st experiment, ZH11-TC as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0069.01 | 1.0 | 0.7281 | | 32.61 | 0.0116 | Y | 2.634 | 0.0494 | Y |
| DP0069.02 | 1.0 | 0.7445 | | 32.25 | 0.0232 | Y | 2.634 | 0.0494 | Y |
| DP0069.03 | 1.0 | 0.4260 | | 33.01 | 0.0044 | Y | 2.634 | 0.0494 | Y |
| DP0069.05 | 1.0 | 0.7445 | | 32.35 | 0.0187 | Y | 2.634 | 0.0494 | Y |
| DP0069.07 | 1.0 | 0.4260 | | 32.69 | 0.0092 | Y | 2.634 | 0.0494 | Y |
| DP0069.08 | 1.0 | 0.7445 | | 31.28 | 0.1221 | | 2.634 | 0.0494 | Y |
| DP0069.09 | 1.0 | 0.7445 | | 32.13 | 0.0292 | Y | 2.634 | 0.0494 | Y |
| DP0069.11 | 1.0 | 0.7445 | | 31.17 | 0.1445 | | 2.634 | 0.0494 | Y |
| DP0069.12 | 1.1 | 0.0830 | | 30.98 | 0.1884 | | 2.634 | 0.0494 | Y |
| DP0069.15 | 1.0 | 0.7445 | | 32.67 | 0.0096 | Y | 2.634 | 0.0494 | Y |
| ZH11-TC | 1.0 | | | 29.23 | | | 2.229 | | |
| DP0069 (construct) | 1.0 | 0.5268 | | 32.11 | 0.0138 | Y | 2.634 | 0.0494 | Y |

TABLE 25

Low nitrogen tolerance assay of OsEIL2 transgenic rice plants under greenhouse low nitrogen conditions (1st experiment, DP0158 as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0069.01 | 1.0 | 0.7281 | | 32.61 | 0.5968 | | 2.634 | 0.3702 | |
| DP0069.02 | 1.0 | 0.7445 | | 32.25 | 0.7968 | | 2.634 | 0.3702 | |
| DP0069.03 | 1.0 | 0.4260 | | 33.01 | 0.4053 | | 2.634 | 0.3702 | |
| DP0069.05 | 1.0 | 0.7445 | | 32.35 | 0.7355 | | 2.634 | 0.3702 | |
| DP0069.07 | 1.0 | 0.4260 | | 32.69 | 0.5545 | | 2.634 | 0.3702 | |
| DP0069.08 | 1.0 | 0.7445 | | 31.28 | 0.6401 | | 2.634 | 0.3702 | |
| DP0069.09 | 1.0 | 0.7445 | | 32.13 | 0.8666 | | 2.634 | 0.3702 | |
| DP0069.11 | 1.0 | 0.7445 | | 31.17 | 0.5796 | | 2.634 | 0.3702 | |
| DP0069.12 | 1.1 | 0.0830 | | 30.98 | 0.4852 | | 2.634 | 0.3702 | |
| DP0069.15 | 1.0 | 0.7445 | | 32.67 | 0.5647 | | 2.634 | 0.3702 | |
| DP0158 | 1.0 | | | 31.90 | | | 2.449 | | |
| DP0069 (construct) | 1.0 | 0.5268 | | 32.11 | 0.8581 | | 2.634 | 0.3702 | |

In the second experiment, the same ten lines were tested, and the experiment design and the treatment were same to that in the second experiment. After low nitrogen stressed for 35 days, tiller number, SPAD value and fresh weight were measured. The average SPAD value and fresh weight of the OsEIL2 transgenic rice were more than that of ZH11-TC and DP0158 controls at construct level. At the transgenic line level, nine line showed greater tiller number, eight lines showed greater SPAD value and nine lines showed greater fresh weight than ZH11-TC control; four lines showed greater tiller number, nine lines showed greater SPAD value and ten lines showed greater fresh weight than DP0158 control (Table 26 and 27). These results further demonstrate OsEIL2 transgenic rice obtained enhanced low nitrogen tolerance or improved NUE, and OsEIL2 plays a role in enhancing NUE of transgenic plants.

TABLE 26

Low nitrogen tolerance assay of OsEIL2 transgenic rice plants under greenhouse low nitrogen conditions (2nd experiment, ZH11-TC as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0069.01 | 2.3 | 0.0642 | | 37.84 | 0.0525 | | 4.536 | 0.0563 | |
| DP0069.03 | 2.9 | 0.0000 | Y | 38.32 | 0.0110 | Y | 4.370 | 0.1938 | |
| DP0069.05 | 2.1 | 0.2236 | | 37.70 | 0.0766 | | 4.246 | 0.3984 | |
| DP0069.07 | 2.3 | 0.0480 | Y | 37.51 | 0.1244 | | 4.146 | 0.6331 | |
| DP0069.08 | 2.6 | 0.0012 | Y | 36.74 | 0.5651 | | 4.482 | 0.0872 | |
| DP0069.09 | 2.1 | 0.2756 | | 36.53 | 0.7610 | | 4.082 | 0.8080 | |

TABLE 26-continued

Low nitrogen tolerance assay of OsEIL2 transgenic rice plants under greenhouse low nitrogen conditions (2$^{nd}$ experiment, ZH11-TC as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0069.10 | 2.0 | 0.3353 | | 36.29 | 0.9901 | | 4.160 | 0.5967 | |
| DP0069.11 | 1.9 | 0.6480 | | 36.23 | 0.9509 | | 4.195 | 0.5109 | |
| DP0069.12 | 1.7 | 0.7612 | | 34.80 | 0.0645 | | 3.974 | 0.8781 | |
| DP0069.15 | 2.1 | 0.1791 | | 37.26 | 0.2239 | | 4.068 | 0.8470 | |
| ZH11-TC | 1.8 | | | 36.28 | | | 4.016 | | |
| DP0069 (construct) | 2.2 | 0.0775 | | 36.92 | 0.3761 | | 4.226 | 0.3780 | |

TABLE 27

Low nitrogen tolerance assay of OsEIL2 transgenic rice plants under greenhouse low nitrogen conditions (2$^{nd}$ experiment, DP0158 as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0069.01 | 2.3 | 0.9253 | | 37.84 | 0.0068 | Y | 4.536 | 0.0154 | Y |
| DP0069.03 | 2.9 | 0.0175 | Y | 38.32 | 0.0009 | Y | 4.370 | 0.0696 | |
| DP0069.05 | 2.1 | 0.5892 | | 37.70 | 0.0112 | Y | 4.246 | 0.1740 | |
| DP0069.07 | 2.3 | 0.8255 | | 37.51 | 0.0213 | Y | 4.146 | 0.3211 | |
| DP0069.08 | 2.6 | 0.1368 | | 36.74 | 0.1800 | | 4.482 | 0.0261 | Y |
| DP0069.09 | 2.1 | 0.5050 | | 36.53 | 0.2848 | | 4.082 | 0.4486 | |
| DP0069.10 | 2.0 | 0.4275 | | 36.29 | 0.4366 | | 4.160 | 0.2965 | |
| DP0069.11 | 1.9 | 0.1935 | | 36.23 | 0.4815 | | 4.195 | 0.2411 | |
| DP0069.12 | 1.7 | 0.0393 | | 34.80 | 0.2787 | | 3.974 | 0.7178 | |
| DP0069.15 | 2.1 | 0.6795 | | 37.26 | 0.0475 | Y | 4.068 | 0.4791 | |
| DP0158 | 2.2 | | | 35.67 | | | 3.875 | | |
| DP0069 (construct) | 2.2 | 0.8598 | | 36.92 | 0.0830 | | 4.226 | 0.1415 | |

6) GH NUE Validation Results of OsPPO3 (DP0097) Transgenic Rice

Twelve OsPPO3 transgenic lines were tested using ZH11-TC seedlings as their corresponding controls. After cultured in low nitrogen solution for 32 days, eight lines showed greater average tiller numbers, ten lines showed greater average SPAD values and six lines showed greater average fresh weights than their controls. As shown in Table 28, two lines exhibited significantly greater tiller numbers, two lines exhibited significantly greater SPAD values, and one line exhibited significantly fresh weight than their controls. These results demonstrate that the OsPPO3 transgenic rice had enhanced low nitrogen tolerance or improved NUE at seedling stage.

TABLE 28

Low nitrogen tolerance assay of OsPPO3 transgenic rice plants under greenhouse low nitrogen conditions

| Line ID | Tiller number | | | SPAD value | | | Fresh weight | | |
|---|---|---|---|---|---|---|---|---|---|
| | Average tiller number | P value | P ≤ 0.1 | Average SPAD value | P value | P ≤ 0.1 | Average fresh weight | P value | P ≤ 0.1 |
| DP0097.03 | 1.8 | 0.7162 | | 39.69 | 0.0871 | Y | 4.984 | 0.3778 | |
| ZH11-TC | 1.6 | | | 35.50 | | | 4.390 | | |
| DP0097.11 | 1.3 | 0.7453 | | 35.85 | 0.3255 | | 3.566 | 0.4631 | |
| ZH11-TC | 1.1 | | | 33.80 | | | 4.093 | | |
| DP0097.12 | 1.4 | 0.1819 | | 38.70 | 0.3160 | | 4.738 | 0.4178 | |
| ZH11-TC | 1.0 | | | 36.16 | | | 4.081 | | |
| DP0097.18 | 2.1 | 0.0143 | Y | 39.73 | 0.2011 | | 4.640 | 0.7226 | |
| ZH11-TC | 1.3 | | | 37.45 | | | 4.471 | | |
| DP0097.21 | 1.3 | 0.7222 | | 36.81 | 0.9944 | | 3.771 | 0.3124 | |
| ZH11-TC | 1.1 | | | 36.80 | | | 4.345 | | |
| DP0097.22 | 1.1 | 0.7771 | | 37.23 | 0.0230 | Y | 4.450 | 0.0762 | Y |
| ZH11-TC | 1.0 | | | 34.40 | | | 3.813 | | |

TABLE 28-continued

Low nitrogen tolerance assay of OsPPO3 transgenic rice plants under greenhouse low nitrogen conditions

| | Tiller number | | | SPAD value | | | Fresh weight | | |
|---|---|---|---|---|---|---|---|---|---|
| Line ID | Average tiller number | P value | P ≤ 0.1 | Average SPAD value | P value | P ≤ 0.1 | Average fresh weight | P value | P ≤ 0.1 |
| DP0097.24 | 1.0 | 1.0000 | | 33.96 | 0.4027 | | 3.629 | 0.8797 | |
| ZH11-TC | 1.0 | | | 32.03 | | | 3.709 | | |
| DP0097.33 | 1.0 | 1.0000 | | 34.80 | 0.8849 | | 3.100 | 0.3303 | |
| ZH11-TC | 1.0 | | | 34.64 | | | 3.479 | | |
| DP0097.34 | 1.1 | 0.6894 | | 35.74 | 0.2728 | | 3.893 | 0.4743 | |
| ZH11-TC | 1.0 | | | 33.39 | | | 3.508 | | |
| DP0097.35 | 1.6 | 0.0706 | Y | 33.13 | 0.1332 | | 4.265 | 0.5881 | |
| ZH11-TC | 1.1 | | | 35.66 | | | 3.966 | | |
| DP0097.36 | 1.0 | 1.0000 | | 33.98 | 0.7092 | | 3.491 | 0.6967 | |
| ZH11-TC | 1.0 | | | 33.21 | | | 3.724 | | |

In the second experiment, ten lines were tested, ZH11-TC and DP0158 seedlings were used as controls, and randomized block design was used. Twelve rice plants from each transgenic line, ZH11-TC and DP0158 were planted in one container. When the rice plants grew to 3-leaf stage, Hoagland solution containing 0.75 mM potassium nitrate was applied to these plants. After low nitrogen stressed for 36 days, tiller number, SPAD value and fresh weight were measured. The average tiller number, SPAD value and fresh weight of the OsPPO3 transgenic rice was greater than that of ZH11-TC and DP0158 controls at the construct level. OsPPO3 transgenic rice plants exhibited significantly greater SPAD value and fresh weight than ZH11-TC control.

As shown in Table 29 and 30, ten lines exhibited greater fresh weights than ZH11-TC control, and eight lines exhibited fresh weights than DP0158 control. These results demonstrate OsLRP1 transgenic rice obtained enhanced low nitrogen tolerance or improved NUE, and over-expression of OsLRP1 enhances NUE of transgenic plants.

TABLE 29

Low nitrogen tolerance assay of OsPPO3 transgenic rice plants under greenhouse low nitrogen conditions (2$^{nd}$ experiment, ZH11-TC as control)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0097.03 | 1.0 | 0.7162 | | 34.37 | 0.0274 | Y | 2.702 | 0.1905 | |
| DP0097.11 | 1.1 | 0.2600 | | 34.37 | 0.0274 | Y | 2.737 | 0.1348 | |
| DP0097.12 | 1.0 | 0.7162 | | 34.37 | 0.0274 | Y | 3.001 | 0.0037 | Y |
| DP0097.18 | 1.1 | 0.1316 | | 34.37 | 0.0274 | Y | 3.065 | 0.0012 | Y |
| DP0097.21 | 1.1 | 0.4563 | | 34.37 | 0.0274 | Y | 2.922 | 0.0131 | Y |
| DP0097.22 | 1.0 | 0.7162 | | 34.37 | 0.0274 | Y | 3.042 | 0.0018 | Y |
| DP0097.24 | 1.0 | 0.7162 | | 34.37 | 0.0274 | Y | 2.936 | 0.0106 | Y |
| DP0097.33 | 1.0 | 0.7162 | | 34.37 | 0.0274 | Y | 2.720 | 0.1593 | |
| DP0097.34 | 1.0 | 0.7162 | | 34.37 | 0.0274 | Y | 2.903 | 0.0172 | Y |
| DP0097.35 | 1.0 | 0.7162 | | 34.37 | 0.0274 | Y | 2.693 | 0.2059 | |
| ZH11-TC | 1.0 | | | 31.35 | | | 2.456 | | |
| DP0097 (construct) | 1.1 | 0.5088 | | 34.37 | 0.0274 | Y | 2.872 | 0.0111 | Y |

TABLE 30

Low nitrogen tolerance assay of OsPPO3 transgenic rice plants under greenhouse low nitrogen conditions (2$^{nd}$ experiment, DP0158 as control)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0097.03 | 1.0 | 0.7162 | | 34.37 | 0.5786 | | 2.702 | 0.9541 | |
| DP0097.11 | 1.1 | 0.2600 | | 34.37 | 0.5786 | | 2.737 | 0.8975 | |
| DP0097.12 | 1.0 | 0.7162 | | 34.37 | 0.5786 | | 3.001 | 0.1242 | |
| DP0097.18 | 1.1 | 0.1316 | | 34.37 | 0.5786 | | 3.065 | 0.0608 | |
| DP0097.21 | 1.1 | 0.4563 | | 34.37 | 0.5786 | | 2.922 | 0.2652 | |
| DP0097.22 | 1.0 | 0.7162 | | 34.37 | 0.5786 | | 3.042 | 0.0794 | |

TABLE 30-continued

Low nitrogen tolerance assay of OsPPO3 transgenic rice plants under
greenhouse low nitrogen conditions (2$^{nd}$ experiment, DP0158 as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0097.24 | 1.0 | 0.7162 | | 34.37 | 0.5786 | | 2.936 | 0.2345 | |
| DP0097.33 | 1.0 | 0.7162 | | 34.37 | 0.5786 | | 2.720 | 0.9673 | |
| DP0097.34 | 1.0 | 0.7162 | | 34.37 | 0.5786 | | 2.903 | 0.3097 | |
| DP0097.35 | 1.0 | 0.7162 | | 34.37 | 0.5786 | | 2.693 | 0.9190 | |
| DP0158 | 1.0 | | | 33.61 | | | 2.713 | | |
| DP0097 | 1.1 | 0.5088 | | 34.37 | 0.5786 | | 2.872 | 0.3303 | |

In the third experiment, the same ten lines were tested, and the experiment design and the treatment were same to that in the second experiment. The rice plants were low nitrogen stressed for 35 days. The average tiller number, SPAD value and fresh weight of the OsPPO3 transgenic rice were more than that DP0158 controls at construct level. The SPAD value of OsPPO3 transgenic rice was significantly greater than DP0158 control. As shown in Table 31 and 32, nine transgenic lines showed greater SPAD values than ZH11-TC control; and ten lines exhibited greater SPAD values and fresh weights than DP0158 control. These results demonstrate OsPPO3 transgenic rice obtained enhanced low nitrogen tolerance or improved NUE, and OsPPO3 plays a role in enhancing NUE of transgenic plants.

TABLE 31

Low nitrogen tolerance assay of OsPPO3 transgenic rice plants under
greenhouse low nitrogen conditions (3$^{rd}$ experiment, ZH11-TC as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0097.03 | 1.0 | 0.8372 | | 33.34 | 0.8421 | | 4.034 | 0.6876 | |
| DP0097.11 | 1.4 | 0.0037 | Y | 34.52 | 0.2836 | | 4.281 | 0.8917 | |
| DP0097.12 | 1.0 | 0.8372 | | 33.26 | 0.8854 | | 4.022 | 0.6695 | |
| DP0097.18 | 1.0 | 0.8372 | | 33.34 | 0.8396 | | 4.126 | 0.8400 | |
| DP0097.21 | 1.0 | 0.8372 | | 34.42 | 0.3168 | | 4.145 | 0.8733 | |
| DP0097.22 | 1.0 | 0.8372 | | 31.78 | 0.3406 | | 3.888 | 0.4720 | |
| DP0097.24 | 1.0 | 0.8372 | | 33.08 | 0.9912 | | 3.941 | 0.5467 | |
| DP0097.33 | 1.0 | 0.8372 | | 34.46 | 0.3045 | | 4.188 | 0.9480 | |
| DP0097.34 | 1.1 | 0.3292 | | 33.54 | 0.7274 | | 4.151 | 0.8831 | |
| DP0097.35 | 1.1 | 0.5550 | | 33.90 | 0.5366 | | 4.180 | 0.9336 | |
| ZH11-TC | 1.0 | | | 33.07 | | | 4.218 | | |
| DP0097 (construct) | 1.1 | 0.4993 | | 33.56 | 0.6756 | | 4.096 | 0.7720 | |

TABLE 32

Low nitrogen tolerance assay of OsPPO3 transgenic rice plants under greenhouse
low nitrogen conditions (3$^{rd}$ experiment, DP0158 as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0097.03 | 1.0 | 0.8372 | | 33.34 | 0.0275 | Y | 4.034 | 0.1409 | |
| DP0097.11 | 1.4 | 0.0037 | Y | 34.52 | 0.0021 | Y | 4.281 | 0.0443 | Y |
| DP0097.12 | 1.0 | 0.8372 | | 33.26 | 0.0317 | Y | 4.022 | 0.1477 | |
| DP0097.18 | 1.0 | 0.8372 | | 33.34 | 0.0273 | Y | 4.126 | 0.0944 | |
| DP0097.21 | 1.0 | 0.8372 | | 34.42 | 0.0027 | Y | 4.145 | 0.0863 | |
| DP0097.22 | 1.0 | 0.8372 | | 31.78 | 0.2930 | | 3.888 | 0.2480 | |
| DP0097.24 | 1.0 | 0.8372 | | 33.08 | 0.0438 | Y | 3.941 | 0.2034 | |
| DP0097.33 | 1.0 | 0.8372 | | 34.46 | 0.0024 | Y | 4.188 | 0.0704 | |
| DP0097.34 | 1.1 | 0.3292 | | 33.54 | 0.0186 | Y | 4.151 | 0.0841 | |
| DP0097.35 | 1.1 | 0.5550 | | 33.90 | 0.0087 | Y | 4.180 | 0.0732 | |
| DP0158 | 1.0 | | | 30.35 | | | 3.357 | | |
| DP0097 (construct) | 1.1 | 0.4993 | | 33.56 | 0.0069 | Y | 4.096 | 0.0812 | |

7) GH NUE Validation Results of OsTTP1 (DP0299) Transgenic Rice

Twelve OsTTP1 transgenic lines were tested using ZH11-TC seedlings as controls in the first experiment. After cultured in low nitrogen solution for 45 days, seven lines had greater average tiller numbers, eleven lines had greater average SPAD values, and nine lines had greater fresh weights than their ZH11-TC controls. As shown in Table 33, two lines (DP0299.04 and DP0299.17) exhibited significantly greater tiller numbers, SPAD values and fresh weights, and four lines showed significantly greater average SPAD values than ZH11-TC control. These results indicate that the OsTTP1 transgenic rice plants had enhanced low nitrogen tolerance or improved NUE at seedling stage.

In the second experiment, ten lines were tested, ZH11-TC and DP0158 seedlings were used as controls, and randomized block design was used. Twelve rice plants from each transgenic line, ZH11-TC and DP0158 were planted in one container, repeated twice. When the rice plants grew to 3-leaf stage, Hoagland solution containing 0.75 mM potassium nitrate was applied to these plants for 36 days. The OsTTP1 transgenic rice exhibited greater average SPAD value and fresh weight than either ZH11-TC or DP0158 control at the construct level. The average tiller number of OsTTP1 transgenic rice was significantly greater than ZH11-TC control, and the SPAD value was significantly greater than ZH11-TC and DP0158 controls.

As shown in Table 34, all the ten lines exhibited greater tiller number, SPAD value and fresh weight than ZH11-TC control. As shown in Table 35, seven lines exhibited greater tiller number, ten lines exhibited greater SPAD value, and eight lines exhibited fresh weight than DP0158 control. These results further demonstrate OsTTP1 transgenic rice obtained enhanced low nitrogen tolerance or improved NUE, and over-expression of OsTTP1 enhances NUE of transgenic plants.

TABLE 33

Low nitrogen tolerance assay of OsTTP1 transgenic rice plants under greenhouse low nitrogen conditions (1$^{st}$ experiment)

| Line ID | Tiller number | | | SPAD value | | | Fresh weight | | |
|---|---|---|---|---|---|---|---|---|---|
| | Average tiller number | P value | P ≤ 0.1 | Average SPAD value | P value | P ≤ 0.1 | Average fresh weight | P value | P ≤ 0.1 |
| DP0299.03 | 1.1 | 1.0000 | | 37.28 | 0.7871 | | 4.290 | 0.5555 | |
| ZH11-TC | 1.1 | | | 36.85 | | | 3.973 | | |
| DP0299.04 | 1.5 | 0.0330 | Y | 40.74 | 0.0003 | Y | 4.499 | 0.0162 | Y |
| ZH11-TC | 1.0 | | | 36.95 | | | 3.661 | | |
| DP0299.05 | 1.1 | 1.0000 | | 37.46 | 0.2331 | | 3.674 | 0.8079 | |
| ZH11-TC | 1.1 | | | 35.24 | | | 3.563 | | |
| DP0299.06 | 1.3 | 0.5906 | | 36.90 | 0.0804 | Y | 3.801 | 0.3470 | |
| ZH11-TC | 1.1 | | | 34.81 | | | 3.273 | | |
| DP0299.07 | 1.1 | 0.5480 | | 41.80 | 0.0000 | Y | 4.306 | 0.1974 | |
| ZH11-TC | 1.0 | | | 36.20 | | | 3.868 | | |
| DP0299.09 | 1.0 | 1.0000 | | 40.13 | 0.1170 | | 4.340 | 0.5545 | |
| ZH11-TC | 1.0 | | | 37.79 | | | 4.055 | | |
| DP0299.11 | 1.1 | 0.6308 | | 41.71 | 0.0115 | Y | 4.855 | 0.1792 | |
| ZH11-TC | 1.0 | | | 36.95 | | | 3.969 | | |
| DP0299.13 | 1.3 | 0.2269 | | 39.68 | 0.0010 | Y | 4.211 | 0.1474 | |
| ZH11-TC | 1.0 | | | 35.49 | | | 3.639 | | |
| DP0299.17 | 1.6 | 0.0144 | Y | 40.19 | 0.0009 | Y | 4.303 | 0.0514 | Y |
| ZH11-TC | 1.0 | | | 35.24 | | | 3.390 | | |

TABLE 34

Low nitrogen tolerance assay of OsTTP1 transgenic rice plants under greenhouse low nitrogen conditions (2$^{nd}$ experiment, ZH11-TC as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0299.03 | 1.8 | 0.0491 | Y | 34.08 | 0.5596 | | 4.041 | 0.5030 | |
| DP0299.04 | 2.0 | 0.0135 | Y | 35.56 | 0.0329 | Y | 4.046 | 0.4914 | |
| DP0299.05 | 2.0 | 0.0135 | Y | 34.10 | 0.5492 | | 4.034 | 0.5194 | |
| DP0299.07 | 1.6 | 0.2879 | | 36.02 | 0.0088 | Y | 4.044 | 0.4967 | |
| DP0299.09 | 1.8 | 0.0773 | | 35.27 | 0.0671 | | 4.139 | 0.3097 | |
| DP0299.11 | 1.9 | 0.0387 | Y | 35.65 | 0.0258 | Y | 4.191 | 0.2302 | |
| DP0299.13 | 1.6 | 0.2879 | | 35.39 | 0.0499 | Y | 3.943 | 0.7460 | |
| DP0299.14 | 2.0 | 0.0102 | Y | 35.60 | 0.0290 | Y | 4.017 | 0.5575 | |
| DP0299.15 | 1.6 | 0.3359 | | 35.70 | 0.0224 | Y | 3.911 | 0.8334 | |
| DP0299.17 | 1.8 | 0.0619 | | 35.90 | 0.0126 | Y | 4.010 | 0.5742 | |
| ZH11-TC | 1.4 | | | 33.53 | | | 3.851 | | |
| DP0299 (construct) | 1.8 | 0.0373 | Y | 35.33 | 0.0303 | Y | 4.037 | 0.4729 | |

TABLE 35

Low nitrogen tolerance assay of OsTTP1 transgenic rice plants under greenhouse low nitrogen conditions (2$^{nd}$ experiment, DP0158 as control)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0299.03 | 1.8 | 0.6561 | | 34.08 | 0.6994 | | 4.041 | 0.9147 | |
| DP0299.04 | 2.0 | 0.3433 | | 35.56 | 0.0528 | | 4.046 | 0.9001 | |
| DP0299.05 | 2.0 | 0.3433 | | 34.10 | 0.6879 | | 4.034 | 0.9349 | |
| DP0299.07 | 1.6 | 0.6459 | | 36.02 | 0.0155 | Y | 4.044 | 0.9068 | |
| DP0299.09 | 1.8 | 0.8070 | | 35.27 | 0.1023 | | 4.139 | 0.6503 | |
| DP0299.11 | 1.9 | 0.5852 | | 35.65 | 0.0421 | Y | 4.191 | 0.5240 | |
| DP0299.13 | 1.6 | 0.6459 | | 35.39 | 0.0779 | | 3.943 | 0.8114 | |
| DP0299.14 | 2.0 | 0.2946 | | 35.60 | 0.0471 | Y | 4.017 | 0.9808 | |
| DP0299.15 | 1.6 | 0.5756 | | 35.70 | 0.0369 | Y | 3.911 | 0.7247 | |
| DP0299.17 | 1.8 | 0.7302 | | 35.90 | 0.0217 | Y | 4.010 | 0.9994 | |
| DP0158 | 1.8 | | | 33.72 | | | 4.010 | | |
| DP0299 (construct) | 1.8 | 0.7284 | | 35.33 | 0.0524 | | 4.037 | 0.9171 | |

Example 5

Laboratory Chlorate Assay of Transgenic Rice Plants

Nitrate is a major source of inorganic nitrogen utilized by higher plants. Chlorate is a nitrate analog which can be absorb, transported by the same system with nitrogen and reduced to a toxic compound (chlorite) by nitrate reductase (NR) in plants. To further confirm the nitrogen use efficiency, chlorate solution is selected to treat seedlings, and seedlings which are sensitive to chlorate will be considered to have better nitrogen use efficiency or low nitrogen tolerance.

Laboratory Chlorate Assay Method:

About ten transgenic lines from a construct were selected and tested by chlorate solution. ZH11-TC and empty vector (DP0158) transgenic plants were used as controls.

T$_2$ transgenic seeds were sterilized and germinated as description in Example 4, and this assay was performed in culture room kept temperature at 28-30° C. and humidity around ~30%. The germinated seeds were placed in a tube with a hole at the bottom, and water cultured at 30° C. for 6 days till one-leaf and one-terminal bud stage. Uniform seedlings about 5.5 cm in height were selected for chlorate screening. Randomized block design was used in this experiment. There are five blocks in one screened container. Each transgenic line was placed in one row (12 plants/line), and ZH11-TC and DP0158 seedlings were placed in 3 rows (3*12 plants) randomly in one block. Then the seedlings were treated with 0.4 mM chlorate in concentration for 3-5 days at 10 h day/14 h night, the treated seedlings first encountered night and absorb the chlorate solution which was changed at the third day. After treated for 5 days, the seedlings were then cultured in 1/10 Hoagland's solution (Table 6) for 4 days. The seedlings with withered leaves and totally without green are counted as sensitive; while the seedlings only with necrosed leaves or stem, or bleached leaves are not considered to be sensitive seedlings.

Sensitive rate was used as a parameter to for this assay, which is the percentage of the number of sensitive plants over the total plant number.

The data was analyzed at construct level (all transgenic plants compared to the control) and transgenic line level (different transgenic lines compared to the control) using a statistic model of "Y~seg+line (seg)+rep+error" with random effect of "rep" and Statistic Method of "SAS Proc Glimmix".

Chlorate Assay Results:

1) DP0046 Transgenic Rice

For OsDN-LTP6 transgenic seedlings, in the first experiment, after treated with 0.4 mM chlorate solution for 5 days and cultured in 1/10 Hoagland solution for 4 days, 344 of the 600 (57%) transgenic seedlings died, whereas 65 of the 180 (36%) ZH11-TC seedlings died and 63 of the 180 (35%) DP0158 seedlings died. The sensitive rate of OsDN-LTP6 transgenic seedlings was significantly higher than that of the ZH11-TC (P value=0.0000) and DP0158 (P value=0.0000) controls, indicating the OsDN-LTP6 transgenic seedlings had increased chlorate sensitivity.

Further analysis at transgenic line level demonstrated that all the ten transgenic lines had higher sensitive rates than both of ZH11-TC and DP0158 controls, and six lines showed significantly higher chlorate sensitive rates than ZH11-TC and DP0158 seedlings as illustrated in Table 36. These results strongly demonstrate that OsDN-LTP6 transgenic rice plants had enhanced chlorate sensitivity compared with both ZH11-TC and DP0158 seedlings at the construct and the transgenic line level at seedling stages.

TABLE 36

Chlorate sensitive assay of OsDN-LTP6 transgenic rice seedlings at transgenic line level (1$^{st}$ experiment)

| | Number of | Number of | | CK = ZH11-TC | | CK = DP0158 | |
|---|---|---|---|---|---|---|---|
| Line ID | dead seedlings | total seedlings | Sensitive rate (%) | P value | P ≤ 0.05 | P value | P ≤ 0.05 |
| DP0046.01 | 59 | 60 | 98 | 0.0000 | Y | 0.0000 | Y |
| DP0046.03 | 27 | 60 | 45 | 0.2257 | | 0.1721 | |

TABLE 36-continued

Chlorate sensitive assay of OsDN-LTP6 transgenic rice seedlings at transgenic line level (1$^{st}$ experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP0046.04 | 33 | 60 | 55 | 0.0131 | Y | 0.0087 | Y |
| DP0046.06 | 40 | 60 | 67 | 0.0002 | Y | 0.0000 | Y |
| DP0046.13 | 40 | 60 | 67 | 0.0002 | Y | 0.0000 | Y |
| DP0046.17 | 36 | 60 | 60 | 0.0022 | Y | 0.0014 | Y |
| DP0046.19 | 27 | 60 | 45 | 0.2257 |   | 0.1721 |   |
| DP0046.20 | 38 | 60 | 63 | 0.0006 | Y | 0.0004 | Y |
| DP0046.23 | 22 | 60 | 37 | 0.9383 |   | 0.8159 |   |
| DP0046.27 | 22 | 60 | 37 | 0.9387 |   | 0.8162 |   |
| ZH11-TC | 65 | 180 | 36 |   |   |   |   |
| DP0158 | 63 | 180 | 35 |   |   |   |   |

In the second experiment, after treated with 0.4 mM chlorate solution for 5 days and cultured in 1/10 Hoagland solution for 4 days, 202 of the 540 (37%) transgenic seedlings died, whereas 57 of the 240 (24%) ZH11-TC seedlings died and 56 of the 180 (31%) DP0158 seedlings died. The sensitive rate of OsDN-LTP6 transgenic seedlings was significantly higher than ZH11-TC (P value=0.0015) and higher than DP0158 (P value=0.2187) controls, indicating the OsDN-LTP6 transgenic seedlings had increased chlorate sensitivity.

Analysis at transgenic line level demonstrated that six transgenic lines exhibited higher sensitive rates than both of ZH11-TC and DP0158 controls (Table 37). All these results demonstrate that OsDN-LTP6 transgenic rice plants obtained enhanced chlorate sensitivity at seedling stages. Over-expression of OsDN-LTP6 increases the chlorate sensitivity of transgenic plants.

TABLE 37

Chlorate sensitive assay of OsDN-LTP6 transgenic rice seedlings at transgenic line level (2$^{nd}$ experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP0046.01 | 53 | 60 | 88 | 0.0000 | Y | 0.0000 | Y |
| DP0046.03 | 20 | 60 | 33 | 0.1333 |   | 0.7482 |   |
| DP0046.04 | 8 | 60 | 13 | 0.0878 |   | 0.0108 |   |
| DP0046.06 | 8 | 60 | 13 | 0.0878 |   | 0.0108 |   |
| DP0046.13 | 20 | 60 | 33 | 0.1333 |   | 0.7482 |   |
| DP0046.17 | 22 | 60 | 37 | 0.0470 | Y | 0.4269 |   |
| DP0046.19 | 32 | 60 | 53 | 0.0000 | Y | 0.0032 | Y |
| DP0046.20 | 24 | 60 | 40 | 0.0143 | Y | 0.2091 |   |
| DP0046.23 | 15 | 60 | 25 | 0.8391 |   | 0.3706 |   |
| ZH11-TC | 57 | 240 | 24 |   |   |   |   |
| DP0158 | 56 | 180 | 31 |   |   |   |   |

2) DP0066 Transgenic Rice

For OsBAK1L transgenic rice, in the first experiment, 258 of the 588 transgenic seedlings (44%) died, whereas 73 of the 180 (41%) ZH11-TC seedlings and 57 of the 192 (30%) DP0158 seedlings died, and the sensitive rate of OsBAK1L transgenic seedlings was higher than that of the ZH11-TC control and significantly (P value=0.0014) higher than that of the DP0158 control, indicating that OsBAK1L transgenic seedlings had significantly enhanced chlorate sensitive compared with the DP0158 seedlings at construct level.

Further analysis at transgenic line level is shown in Table 38. Seven of the ten transgenic lines had higher sensitive rates than ZH11-TC control, and eight transgenic lines had higher sensitive rates than DP0158 seedlings. The sensitive rates of six transgenic lines were significantly higher than DP0158 seedlings. These results demonstrate that OsBAK1L transgenic rice plants have enhanced chlorate sensitive compared with DP0158 seedlings at construct and transgenic line level at seedling stages.

TABLE 38

Chlorate sensitive assay of OsBAK1L transgenic rice seedlings at transgenic line level (1$^{st}$ experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP0066.01 | 28 | 60 | 47 | 0.4088 |   | 0.0187 | Y |
| DP0066.03 | 19 | 48 | 40 | 0.9182 |   | 0.1873 |   |
| DP0066.04 | 33 | 60 | 55 | 0.0562 |   | 0.0008 | Y |
| DP0066.05 | 31 | 60 | 52 | 0.1378 |   | 0.0031 | Y |
| DP0066.06 | 28 | 60 | 47 | 0.4088 |   | 0.0187 | Y |
| DP0066.07 | 16 | 60 | 27 | 0.0597 |   | 0.6568 |   |
| DP0066.08 | 25 | 60 | 42 | 0.8801 |   | 0.0889 |   |
| DP0066.12 | 15 | 60 | 25 | 0.0357 |   | 0.4882 |   |
| DP0066.14 | 35 | 60 | 58 | 0.0202 | Y | 0.0002 | Y |
| DP0066.15 | 28 | 60 | 47 | 0.4089 |   | 0.0187 | Y |
| ZH11-TC | 73 | 180 | 41 |   |   |   |   |
| DP0158 | 57 | 192 | 30 |   |   |   |   |

In the second experiment, 221 of the 600 transgenic seedlings (37%) died, whereas 49 of the 180 (27%) ZH11-TC seedlings and 43 of the 180 (24%) DP0158 seedlings died, and the sensitive rate of OsBAK1L transgenic seedlings was significantly higher than ZH11-TC control (P value=0.0250) and DP0158 control (P value=0.0027).

Analysis at transgenic line level showed that nine transgenic lines exhibited higher sensitive rates than ZH11-TC and DP0158 controls, and two lines and five lines exhibited higher sensitive rates than ZH11-TC and DP0158 seedlings, respectively (Table 39). These results demonstrate that OsBAK1L transgenic rice plants have enhanced chlorate sensitive compared with DP0158 seedlings at construct and transgenic line level at seedling stages.

As elucidated in example 4, over-expression of OsBAK1L improved nitrogen use efficiency of the transgenic rice. These cross-validations further confirm the increase low nitrogen tolerance or NUE of OsBAK1L transgenic rice.

3) DP0069 Transgenic Rice

For OsEIL2 transgenic seedlings, in the first experiment, after treated with 0.4 mM chlorate solution for 5 days and cultured in 1/10 Hoagland solution for 4 days, 478 of the 600 (80%) transgenic seedlings died, whereas 126 of the 180 (70%) ZH11-TC seedlings died and 106 of the 180 (59%) DP0158 seedlings died. The sensitive rate of OsEIL2 transgenic seedlings was significantly higher than that of the ZH11-TC (P value=0.0062) and DP0158 (P value=0.0000) controls, indicating the OsEIL2 transgenic seedlings had increased chlorate sensitivity.

Further analysis at transgenic line level demonstrated that all the ten transgenic lines had higher sensitive rates than both of ZH11-TC and DP0158 controls, and nine lines showed significantly higher chlorate sensitive rates than DP0158 seedlings as illustrated in Table 40. All these results strongly demonstrate that OsEIL2 transgenic rice plants had enhanced chlorate sensitivity compared with both ZH11-TC and DP0158 seedlings at construct and transgenic line level at seedling stages. Over-expression of OsEIL2 increases the chlorate sensitivity of transgenic plants.

TABLE 39

Chlorate sensitive assay of OsBAK1L transgenic rice seedlings at transgenic line level (2$^{nd}$ experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP0066.01 | 18 | 60 | 30 | 0.6792 |   | 0.3503 |   |
| DP0066.03 | 20 | 60 | 33 | 0.3688 |   | 0.1561 |   |
| DP0066.04 | 24 | 60 | 40 | 0.0684 |   | 0.0200 | Y |
| DP0066.05 | 29 | 60 | 48 | 0.0040 | Y | 0.0008 | Y |
| DP0066.06 | 15 | 60 | 25 | 0.7367 |   | 0.8620 |   |
| DP0066.07 | 19 | 60 | 32 | 0.5106 |   | 0.2386 |   |
| DP0066.08 | 29 | 60 | 48 | 0.0040 | Y | 0.0008 | Y |
| DP0066.12 | 20 | 60 | 33 | 0.3688 |   | 0.1561 |   |
| DP0066.14 | 24 | 60 | 40 | 0.0684 |   | 0.0200 | Y |
| DP0066.15 | 23 | 60 | 38 | 0.1103 |   | 0.0352 | Y |
| ZH11-TC | 49 | 180 | 27 |   |   |   |   |
| DP0158 | 43 | 192 | 24 |   |   |   |   |

TABLE 40

Chlorate sensitive assay of OsEIL2 transgenic rice
seedlings at transgenic line level (1$^{st}$ experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP0069.01 | 50 | 60 | 83 | 0.0500 | Y | 0.0015 | Y |
| DP0069.02 | 47 | 60 | 78 | 0.2181 |   | 0.0096 | Y |
| DP0069.03 | 49 | 60 | 82 | 0.0853 |   | 0.0028 | Y |
| DP0069.05 | 49 | 60 | 82 | 0.0853 |   | 0.0028 | Y |
| DP0069.07 | 45 | 60 | 75 | 0.4608 |   | 0.0301 | Y |
| DP0069.08 | 47 | 60 | 78 | 0.2181 |   | 0.0096 | Y |
| DP0069.09 | 45 | 60 | 75 | 0.4608 |   | 0.0301 | Y |
| DP0069.10 | 50 | 60 | 83 | 0.0500 | Y | 0.0015 | Y |
| DP0069.11 | 53 | 60 | 88 | 0.0083 | Y | 0.0002 | Y |
| DP0069.15 | 43 | 60 | 72 | 0.8030 |   | 0.0822 |   |
| ZH11-TC | 126 | 180 | 70 |   |   |   |   |
| DP0158 | 106 | 180 | 59 |   |   |   |   |

In the second experiment, after treated with 0.4 mM chlorate solution for 2 days and cultured in 1/10 Hoagland solution for 4 days, 470 of the 600 (80%) transgenic seedlings died, whereas 99 of the 180 (55%) ZH11-TC seedlings died and 60 of the 180 (33%) DP0158 seedlings died. The sensitive rate of OsEIL2 transgenic seedlings was significantly higher than ZH11-TC (P value=0.0000) and DP0158 (P value=0.0000) controls, indicating the OsEIL2 transgenic seedlings had increased chlorate sensitivity.

Analysis at transgenic line level demonstrated that all the ten transgenic lines exhibited significantly higher sensitive rates than both of ZH11-TC and DP0158 controls (Table 41). Most of the transgenic lines exhibited significantly higher chlorate sensitivity than DP0158 seedlings in the two experiments. All these results strongly demonstrate that OsEIL2 transgenic rice plants obtained enhanced chlorate sensitivity at seedling stages. Over-expression of OsEIL2 increases the chlorate sensitivity of transgenic plants.

4) DP0097 Transgenic Rice

For OsPPO3 transgenic seedlings, in the first experiment, after treated with 0.4 mM chlorate solution for 5 days and cultured in 1/10 Hoagland solution for 4 days, 377 of the 600 (63%) transgenic seedlings died, whereas 95 of the 180 (53%) ZH11-TC seedlings and 83 of the 180 (46%) DP0158 seedlings died. The sensitive rate of OsPPO3 transgenic seedlings was significantly higher than that of the ZH11-TC (P value=0.0140) and DP0158 (P value=0.0001) controls, indicating the OsPPO3 transgenic seedlings had increased chlorate sensitivity at construct level at seedling stage.

As shown in Table 42, further analysis at transgenic lines level demonstrated that all the ten transgenic lines exhibited higher sensitive rates than DP0158 seedlings, and five lines showed significantly higher chlorate sensitive rates, and when compared with ZH11-TC control, nine transgenic lines had the higher sensitive rates. All these results indicate that OsPPO3 transgenic rice plants had enhanced chlorate sensitivity at seedling stages. Over-expression of OsPPO3 gene increases the chlorate sensitivity of transgenic plants.

TABLE 41

Chlorate sensitive assay of OsEIL2 transgenic rice
seedlings at transgenic line level (2$^{nd}$ experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP0069.01 | 50 | 60 | 83 | 0.0004 | Y | 0.0000 | Y |
| DP0069.02 | 41 | 60 | 68 | 0.0762 | Y | 0.0000 | Y |
| DP0069.03 | 45 | 60 | 75 | 0.0091 | Y | 0.0000 | Y |
| DP0069.05 | 50 | 60 | 83 | 0.0004 | Y | 0.0000 | Y |
| DP0069.07 | 46 | 60 | 77 | 0.0050 | Y | 0.0000 | Y |
| DP0069.08 | 47 | 60 | 78 | 0.0027 | Y | 0.0000 | Y |
| DP0069.09 | 50 | 60 | 83 | 0.0004 | Y | 0.0000 | Y |
| DP0069.10 | 46 | 60 | 77 | 0.0050 | Y | 0.0000 | Y |
| DP0069.11 | 48 | 60 | 80 | 0.0014 | Y | 0.0000 | Y |
| DP0069.15 | 47 | 60 | 78 | 0.0027 | Y | 0.0000 | Y |
| ZH11-TC | 99 | 180 | 55 |   |   |   |   |
| DP0158 | 60 | 180 | 33 |   |   |   |   |

TABLE 42

Chlorate sensitive assay of OsPPO3 transgenic rice
seedlings at transgenic line level (1st experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP0097.06 | 40 | 60 | 67 | 0.0666 |   | 0.0084 | Y |
| DP0097.11 | 34 | 60 | 57 | 0.6025 |   | 0.1626 |   |
| DP0097.12 | 41 | 60 | 68 | 0.0408 | Y | 0.0046 | Y |
| DP0097.18 | 33 | 60 | 55 | 0.7657 |   | 0.2380 |   |
| DP0097.21 | 45 | 60 | 75 | 0.0043 | Y | 0.0004 | Y |
| DP0097.22 | 47 | 60 | 78 | 0.0012 | Y | 0.0000 | Y |
| DP0097.33 | 39 | 60 | 65 | 0.1052 |   | 0.0147 | Y |
| DP0097.34 | 28 | 60 | 47 | 0.4160 |   | 0.9402 |   |
| DP0097.35 | 36 | 60 | 60 | 0.3347 |   | 0.0685 |   |
| DP0097.36 | 34 | 60 | 57 | 0.6025 |   | 0.1627 |   |
| ZH11-TC | 95 | 180 | 53 |   |   |   |   |
| DP0158 | 83 | 180 | 46 |   |   |   |   |

In the second experiment, after treated with 0.4 mM chlorate solution for 5 days and cultured in 1/10 Hoagland solution for 4 days, 274 of the 600 (46%) transgenic seedlings died, whereas 52 of the 180 (29%) ZH11-TC seedlings and 40 of the 180 (22%) DP0158 seedlings died. The sensitive rate of OsPPO3 transgenic seedlings was significantly higher than ZH11-TC (P value=0.0003) and DP0158 (P value=0.0001) controls.

Analysis at transgenic lines level demonstrated that nine transgenic lines exhibited higher sensitive rates than ZH11-TC and DP0158 seedlings, and six lines and nine lines showed significantly higher chlorate sensitive rates than ZH11-TC and DP0158 seedlings, respectively (Table 43). These results further demonstrate that OsPPO3 transgenic rice plants had enhanced chlorate sensitivity at seedling stages. Over-expression of OsPPO3 gene increases the chlorate sensitivity of transgenic plants.

TABLE 43

Chlorate sensitive assay of OsPPO3 transgenic rice
seedlings at transgenic line level (2nd experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP0097.06 | 34 | 60 | 57 | 0.0003 | Y | 0.0000 | Y |
| DP0097.11 | 32 | 60 | 53 | 0.0012 | Y | 0.0000 | Y |
| DP0097.12 | 28 | 60 | 47 | 0.0146 | Y | 0.0007 | Y |
| DP0097.18 | 22 | 60 | 37 | 0.2626 |   | 0.0317 | Y |
| DP0097.21 | 37 | 60 | 62 | 0.0000 | Y | 0.0000 | Y |
| DP0097.22 | 30 | 60 | 50 | 0.0044 | Y | 0.0002 | Y |
| DP0097.33 | 34 | 60 | 57 | 0.0003 | Y | 0.0000 | Y |
| DP0097.34 | 11 | 60 | 18 | 0.1147 |   | 0.5253 |   |
| DP0097.35 | 22 | 60 | 37 | 0.2626 |   | 0.0317 | Y |
| DP0097.36 | 24 | 60 | 40 | 0.1140 |   | 0.0097 | Y |
| ZH11-TC | 52 | 180 | 29 |   |   |   |   |
| DP0158 | 40 | 180 | 22 |   |   |   |   |

Example 6

Field Low Nitrogen Tolerance Assays of Mature Transgenic Rice Plants

Field low nitrogen tolerance assays were carried out in Beijing. Two nitrogen levels: N-0 (using fertilizer without nitrogen) and N-1 (with normal fertilizer at 180 kg Nitrogen/ha) were set in the experiment. Seed germination and seedling cultivation were performed as described in Example 4. The germinated seeds were planted in a seedbed field. At 3-leaf stage, the seedlings were transplanted into two testing fields, with 4 replicates and 10 plants per replicate for each transgenic line, and the 4 replicates were planted in the same block. The ZH11-TC and DP0158 plants were planted nearby the transgenic lines in the same block, and were used as controls in the statistical analysis.

The rice plants were managed by normal practice using pesticides, but applying phosphorous fertilizer and potassium fertilizer for N-0 treatment and normal fertilizers for N-1.

The SPAD value of the fully expanded flag leaf and top second leaf were measured by SPAD-502 chlorophyll meter at about 10 day after heading. The SPAD value of each transgenic rice line is the arithmetic mean of SPAD values from three rice plants in the middle of one rice row.

The plant height which is the length from the rice stem base to the end of panicle or the end of the highest leaf was measured at 20 day after heading. Six rice plants in the middle of one rice row were measured and the arithmetic mean of these six values is the plant height of the transgenic rice line.

At the end of the season, six representative plants of each transgenic line were harvested from the middle of the row per line. The panicles which have five seeds are considered as effective panicles, and the effective panicle number is the total of the effective panicle per plant. The biomass per plant is the dry weight of the rice plant without root and panicle. The SPAD value, plant height, effective number, biomass and grain weight per plant data were statistically analyzed using mixed linear model by ASRemI program. Positive transgenic lines are selected based on the analysis (P<0.1).
1) Field NUE Validation Results of OsDN-LTP4 (DP0036) Transgenic Rice The grain yield per plant, biomass, effective panicle number and plant height of OsDN-LTP4 transgenic rice plants were measured. Table 44 shows that OsDN-LTP4 transgenic rice exhibited significantly greater grain yield per plant than ZH11-TC and DP0158 controls at the construct level; and all the eleven lines showed greater grain yield per plant than either ZH11-TC or DP0158 control at the transgenic line level under low nitrogen conditions. Table 45 shows that the OsDN-LTP4 transgenic rice exhibited less grain yield per plant than ZH11-TC control and greater grain yield than DP0158 control at the construct level; and eight lines exhibited greater grain yields per plant than DP0158 control at the transgenic line level under field normal nitrogen conditions. The OsDN-LTP4 transgenic rice exhibited 8% and 15% grain yield increase than ZH11-TC and DP0158 control under low nitrogen conditions, respectively; and exhibited 7% grain yield decrease than ZH11-TC control and 3% grain yield increase than DP0158 control under field normal nitrogen conditions. These results demonstrate that OsDN-LTP4 transgenic rice obtained low nitrogen tolerance, and over-expression of OsDN-LTP4 improves the grain yield of transgenic plants under low nitrogen conditions.

As shown in Table 46, the OsDN-LTP4 transgenic rice plants showed significantly greater biomass than either ZH11-TC or DP0158 control at the construct level; and all the eleven lines showed greater biomass at transgenic line level under low nitrogen conditions.

The OsDN-LTP4 transgenic rice plants were significantly taller than both ZH11-TC and DP0158 controls at the construct level; and eight lines were taller than ZH11-TC control, and ten lines were taller than DP0158 control at the transgenic line level under low nitrogen conditions (Table 47). Under normal nitrogen conditions, the OsDN-LTP4 transgenic rice plants were shorter than ZH11-TC control and taller than DP0158 controls at the construct level; and three lines were taller than ZH11-TC control, and six lines were taller than DP0158 control at the transgenic line level (Table 48). The OsDN-LTP4 transgenic rice plants exhibited 1% and 3% plant height increase, irrespectively, under low nitrogen conditions; and 1% decrease than ZH11-TC control and 1% increase than DP0158 control in plant height under normal nitrogen conditions. These results demonstrate that OsDN-LTP4 transgenic rice plants exhibited enhanced low nitrogen tolerance and/or NUE under low nitrogen conditions as reflected by plant height.

The table 49 shows that the OsDN-LTP4 transgenic rice plants exhibited significantly greater effective panicle number than either ZH11-TC or DP0158 control at the construct level; and all the eleven lines exhibited greater effective panicle number than either ZH11-TC or DP0158 control at the transgenic line level under low nitrogen conditions. Under normal nitrogen conditions, the effective panicle number of the OsDN-LTP4 transgenic rice plants was also more than ZH11-TC and DP0158 controls (Table 50). These results demonstrate that OsDN-LTP4 transgenic rice plants exhibited enhanced low nitrogen tolerance and/or NUE under low nitrogen conditions as reflected by the effective panicle number.

There was no significant difference between the OsDN-LTP4 transgenic rice and control for the flag leaf SPAD value and top second leaf SPAD value.

These results indicate that OsDN-LTP4 transgenic rice plants obtained greater grain yield per plant, more biomass, more plant height and more effective panicle number under low nitrogen conditions, over-expression of OsDN-LTP4 improves the plant height, effective panicle number and biomass of transgenic plants, then improves the grain yield per plant under low nitrogen conditions. OsDN-LNP4 gene plays a role in enhancing low nitrogen tolerance and/or NUE.

TABLE 44

Grain yield analysis of OsDN-LTP4 transgenic rice under field low nitrogen condition

| Line ID | Number of survival plants | Number of harvested plants | Yield per plant (g) | CK = ZH11-TC P value | P ≤ 0.1 | CK = DP0158 P value | P ≤ 0.1 |
| --- | --- | --- | --- | --- | --- | --- | --- |
| DP0036.05 | 40 | 24 | 34.33 | 0.425 |   | 0.051 | Y |
| DP0036.07 | 30 | 18 | 34.60 | 0.383 |   | 0.049 | Y |
| DP0036.08 | 40 | 24 | 37.50 | 0.025 | Y | 0.001 | Y |
| DP0036.11 | 40 | 24 | 34.32 | 0.429 |   | 0.052 | Y |
| DP0036.13 | 40 | 24 | 35.73 | 0.151 |   | 0.010 | Y |
| DP0036.15 | 40 | 24 | 37.49 | 0.025 | Y | 0.001 | Y |
| DP0036.16 | 40 | 24 | 35.98 | 0.122 |   | 0.007 | Y |
| DP0036.17 | 30 | 18 | 34.70 | 0.359 |   | 0.044 | Y |
| DP0036.19 | 40 | 23 | 35.54 | 0.177 |   | 0.012 | Y |
| DP0036.20 | 40 | 24 | 35.28 | 0.220 |   | 0.018 | Y |
| DP0036.23 | 40 | 24 | 33.28 | 0.751 |   | 0.143 |   |
| DP0036.TC | 40 | 24 | 32.59 |   |   |   |   |
| DP0158 | 40 | 24 | 30.09 |   |   |   |   |
| DP0036 (construct) |   |   | 35.34 | 0.096 | Y | 0.001 | Y |

TABLE 45

Grain yield analysis of OsDN-LTP4 transgenic rice under field normal nitrogen condition

| Line ID | Number of survival plants | Number of harvested plants | Yield per plant (g) | CK = ZH11-TC P value | CK = ZH11-TC P ≤ 0.1 | CK = DP0158 P value | CK = DP0158 P ≤ 0.1 |
|---|---|---|---|---|---|---|---|
| DP0036.05 | 40 | 24 | 44.65 | 0.653 | | 0.294 | |
| DP0036.07 | 30 | 18 | 41.53 | 0.133 | | 0.924 | |
| DP0036.08 | 40 | 24 | 40.43 | 0.045 | | 0.613 | |
| DP0036.11 | 40 | 24 | 43.14 | 0.318 | | 0.623 | |
| DP0036.13 | 40 | 24 | 42.85 | 0.267 | | 0.699 | |
| DP0036.15 | 40 | 24 | 44.70 | 0.668 | | 0.287 | |
| DP0036.16 | 40 | 24 | 43.03 | 0.295 | | 0.653 | |
| DP0036.17 | 30 | 18 | 41.55 | 0.136 | | 0.930 | |
| DP0036.19 | 38 | 24 | 43.18 | 0.322 | | 0.614 | |
| DP0036.20 | 40 | 24 | 43.99 | 0.488 | | 0.418 | |
| DP0036.23 | 40 | 20 | 44.46 | 0.604 | | 0.329 | |
| ZH11-TC | 40 | 24 | 45.87 | | | | |
| DP0158 | 40 | 24 | 41.80 | | | | |
| DP0036 (construct) | | | 43.05 | 0.114 | | 0.487 | |

TABLE 46

Biomass analysis of OsDN-LTP4 transgenic rice under field low nitrogen condition

| Line ID | Number of survival plants | Number of harvested plants | Biomass (g) | CK = ZH11-TC P value | CK = ZH11-TC P ≤ 0.1 | CK = DP0158 P value | CK = DP0158 P ≤ 0.1 |
|---|---|---|---|---|---|---|---|
| DP0036.05 | 40 | 24 | 25.50 | 0.157 | | 0.236 | |
| DP0036.07 | 30 | 18 | 25.78 | 0.130 | | 0.196 | |
| DP0036.08 | 40 | 24 | 27.60 | 0.009 | Y | 0.016 | Y |
| DP0036.11 | 40 | 24 | 25.90 | 0.100 | Y | 0.156 | |
| DP0036.13 | 40 | 24 | 25.37 | 0.182 | | 0.269 | |
| DP0036.15 | 40 | 24 | 26.96 | 0.023 | Y | 0.040 | Y |
| DP0036.16 | 40 | 24 | 26.35 | 0.057 | Y | 0.093 | Y |
| DP0036.17 | 30 | 18 | 26.28 | 0.073 | Y | 0.115 | |
| DP0036.19 | 40 | 23 | 28.10 | 0.003 | Y | 0.007 | Y |
| DP0036.20 | 40 | 24 | 25.69 | 0.128 | | 0.195 | |
| DP0036.23 | 40 | 24 | 24.44 | 0.428 | | 0.575 | |
| ZH11-TC | 40 | 24 | 23.08 | | | | |
| DP0158 | 40 | 24 | 23.48 | | | | |
| DP0036 (construct) | | | 26.18 | 0.019 | Y | 0.040 | Y |

TABLE 47

Plant height analysis of OsDN-LTP4 transgenic rice under field low nitrogen condition

| Line ID | Number of survival plants | Number of measured plants | Plant height (mm) | CK = ZH11-TC P value | CK = ZH11-TC P ≤ 0.1 | CK = DP0158 P value | CK = DP0158 P ≤ 0.1 |
|---|---|---|---|---|---|---|---|
| DP0036.05 | 40 | 24 | 112.74 | 0.828 | | 0.101 | |
| DP0036.07 | 30 | 24 | 117.15 | 0.008 | Y | 0.000 | Y |
| DP0036.08 | 40 | 24 | 115.18 | 0.104 | | 0.000 | Y |
| DP0036.11 | 40 | 24 | 113.63 | 0.686 | | 0.025 | Y |
| DP0036.13 | 40 | 24 | 110.33 | 0.046 | | 0.944 | |
| DP0036.15 | 40 | 24 | 117.85 | 0.001 | Y | 0.000 | Y |
| DP0036.16 | 40 | 24 | 116.69 | 0.006 | Y | 0.000 | Y |
| DP0036.17 | 30 | 24 | 112.35 | 0.651 | | 0.215 | |
| DP0036.19 | 40 | 24 | 114.29 | 0.369 | | 0.005 | Y |
| DP0036.20 | 40 | 24 | 116.09 | 0.027 | Y | 0.000 | Y |
| DP0036.23 | 40 | 24 | 111.77 | 0.355 | | 0.327 | |

TABLE 47-continued

Plant height analysis of OsDN-LTP4 transgenic rice under field low nitrogen condition

| Line ID | Number of survival plants | Number of measured plants | Plant height (mm) | CK = ZH11-TC P value | CK = ZH11-TC P ≤ 0.1 | CK = DP0158 P value | CK = DP0158 P ≤ 0.1 |
|---|---|---|---|---|---|---|---|
| ZH11-TC | 40 | 24 | 113.05 | | | | |
| DP0158 | 40 | 24 | 110.43 | | | | |
| DP0036 (construct) | | | 114.37 | 0.361 | | 0.006 | Y |

TABLE 48

Plant height analysis of OsDN-LTP4 transgenic rice under field normal nitrogen condition

| Line ID | Number of survival plants | Number of measured plants | Plant height (mm) | CK = ZH11-TC P value | CK = ZH11-TC P ≤ 0.1 | CK = DP0158 P value | CK = DP0158 P ≤ 0.1 |
|---|---|---|---|---|---|---|---|
| DP0036.05 | 40 | 24 | 127.79 | 0.519 | | 0.221 | |
| DP0036.07 | 30 | 24 | 127.98 | 0.653 | | 0.204 | |
| DP0036.08 | 40 | 24 | 126.66 | 0.107 | | 0.741 | |
| DP0036.11 | 40 | 24 | 126.15 | 0.037 | | 0.921 | |
| DP0036.13 | 40 | 24 | 124.90 | 0.004 | | 0.292 | |
| DP0036.15 | 40 | 24 | 130.34 | 0.131 | | 0.000 | Y |
| DP0036.16 | 40 | 24 | 133.32 | 0.000 | Y | 0.000 | Y |
| DP0036.17 | 30 | 24 | 126.16 | 0.064 | | 0.938 | |
| DP0036.19 | 38 | 24 | 128.55 | 0.976 | | 0.069 | Y |
| DP0036.20 | 40 | 24 | 130.29 | 0.161 | | 0.001 | Y |
| DP0036.23 | 40 | 24 | 124.14 | 0.000 | | 0.074 | |
| ZH11-TC | 40 | 24 | 128.58 | | | | |
| DP0158 | 40 | 24 | 126.27 | | | | |
| DP0036 (construct) | | | 127.84 | 0.579 | | 0.237 | |

TABLE 49

The effective panicle number analysis of OsDN-LTP4 transgenic rice under field low nitrogen condition

| Line ID | Number of survival plants | Number of harvested plants | Panicle number | CK = ZH11-TC P value | CK = ZH11-TC P ≤ 0.1 | CK = DP0158 P value | CK = DP0158 P ≤ 0.1 |
|---|---|---|---|---|---|---|---|
| DP0036.05 | 40 | 24 | 7.30 | 0.118 | | 0.407 | |
| DP0036.07 | 30 | 18 | 7.32 | 0.124 | | 0.403 | |
| DP0036.08 | 40 | 24 | 7.94 | 0.002 | Y | 0.020 | Y |
| DP0036.11 | 40 | 24 | 7.51 | 0.040 | Y | 0.186 | |
| DP0036.13 | 40 | 24 | 7.62 | 0.021 | Y | 0.116 | |
| DP0036.15 | 40 | 24 | 7.51 | 0.040 | Y | 0.188 | |
| DP0036.16 | 40 | 24 | 7.60 | 0.023 | Y | 0.123 | |
| DP0036.17 | 30 | 18 | 7.50 | 0.053 | Y | 0.216 | |
| DP0036.19 | 40 | 23 | 7.68 | 0.014 | Y | 0.087 | Y |
| DP0036.20 | 40 | 24 | 7.25 | 0.148 | | 0.478 | |
| DP0036.23 | 40 | 24 | 7.04 | 0.336 | | 0.822 | |
| ZH11-TC | 40 | 24 | 6.62 | | | | |
| DP0158 | 40 | 24 | 6.94 | | | | |
| DP0036 (construct) | | | 7.48 | 0.009 | Y | 0.098 | Y |

TABLE 50

The effective panicle number analysis of OsDN-LTP4 transgenic rice under field normal nitrogen condition

| Line ID | Number of survival plants | Number of harvested plants | Panicle number | CK = ZH11-TC P value | CK = ZH11-TC P ≤ 0.1 | CK = DP0158 P value | CK = DP0158 P ≤ 0.1 |
|---|---|---|---|---|---|---|---|
| DP0036.05 | 40 | 24 | 12.90 | 0.198 | | 0.353 | |
| DP0036.07 | 30 | 18 | 12.46 | 0.545 | | 0.793 | |
| DP0036.08 | 40 | 24 | 12.61 | 0.393 | | 0.617 | |
| DP0036.11 | 40 | 24 | 12.85 | 0.230 | | 0.397 | |
| DP0036.13 | 40 | 24 | 12.78 | 0.273 | | 0.458 | |
| DP0036.15 | 40 | 24 | 12.94 | 0.182 | | 0.328 | |
| DP0036.16 | 40 | 24 | 12.96 | 0.171 | | 0.311 | |
| DP0036.17 | 30 | 18 | 12.69 | 0.349 | | 0.554 | |
| DP0036.19 | 38 | 24 | 12.80 | 0.257 | | 0.437 | |
| DP0036.20 | 40 | 24 | 12.64 | 0.372 | | 0.590 | |
| DP0036.23 | 40 | 20 | 13.32 | 0.057 | Y | 0.122 | |
| ZH11-TC | 40 | 24 | 12.04 | | | | |
| DP0158 | 40 | 24 | 12.28 | | | | |
| DP0036 (construct) | | | 12.81 | 0.123 | | 0.287 | |

2) Field NUE Validation Results of OsDN-LTP7 (DP0063) Transgenic Rice

The grain yield per plant, biomass, effective panicle number and plant height of OsDN-LTP7 transgenic rice plants were measured. Table 51 shows that OsDN-LTP7 transgenic rice exhibited less grain yield per plant than ZH11-TC and DP0158 controls at the construct level under low nitrogen conditions. Table 52 shows that the OsDN-LTP7 transgenic rice exhibited less grain yield per plant than ZH11-TC control and greater grain yield than DP0158 control at the construct level under field normal nitrogen conditions. These results demonstrate that OsDN-LTP7 transgenic rice did not show low nitrogen tolerance as reflected by grain yield per plan. There was also no significant difference between the OsDN-LTP7 transgenic rice and control for the biomass, effective panicle number and plant height.

The SPAD values of the plants under low nitrogen conditions were measured. As shown in Table 53, the flag leaf SPAD value of OsDN-LTP7 transgenic rice plants was 40.44, and was significantly higher than that of ZH11-TC and DP0158 plants at construct level. At transgenic line level, eight lines exhibited significantly higher flag leaf SPAD values than ZH11-TC control, and seven lines exhibited significantly higher flag leaf SPAD values than that of DP0158 control. As shown in Table 54, the top second leaf SPAD value of OsDN-LTP7 transgenic rice plants was 38.89, and was significantly higher than that of ZH11-TC control at construct level. At transgenic line level, four lines exhibited significantly higher top second leaf SPAD values than ZH11-TC control, and three lines exhibited significantly higher top second leaf SPAD values than that of DP0158 control. These results demonstrate that OsDN-LTP7 transgenic rice plants showed better growth status than the controls under field low nitrogen conditions, OsDN-LTP7 may plays a role in improving low nitrogen tolerance and/or NUE by enhancing the chlorophyll content.

TABLE 51

Grain yield analysis of OsDN-LTP7 transgenic rice under field low nitrogen condition

| Line ID | Number of survival plants | Number of harvested plants | Yield per plant (g) | CK = ZH11-TC P value | CK = ZH11-TC P ≤ 0.1 | CK = DP0158 P value | CK = DP0158 P ≤ 0.1 |
|---|---|---|---|---|---|---|---|
| DP0063.01 | 37 | 22 | 28.94 | 0.094 | | 0.596 | |
| DP0063.02 | 38 | 21 | 30.45 | 0.325 | | 0.868 | |
| DP0063.04 | 40 | 22 | 32.14 | 0.838 | | 0.344 | |
| DP0063.05 | 39 | 19 | 28.16 | 0.042 | | 0.375 | |
| DP0063.06 | 39 | 22 | 28.50 | 0.060 | | 0.463 | |
| DP0063.08 | 38 | 22 | 30.59 | 0.358 | | 0.818 | |
| DP0063.09 | 40 | 24 | 27.20 | 0.014 | | 0.186 | |
| DP0063.10 | 39 | 22 | 31.40 | 0.584 | | 0.547 | |
| DP0063.13 | 39 | 21 | 31.29 | 0.550 | | 0.580 | |
| DP0063.15 | 38 | 23 | 30.95 | 0.451 | | 0.694 | |
| DP0063.16 | 30 | 17 | 30.86 | 0.454 | | 0.736 | |
| ZH11-TC | 39 | 23 | 32.59 | | | | |
| DP0158 | 38 | 23 | 30.09 | | | | |
| DP0063 (construct) | | | 30.04 | 0.119 | | 0.978 | |

TABLE 52

Grain yield analysis of OsDN-LTP7 transgenic rice under field normal nitrogen condition

| Line ID | Number of survival plants | Number of harvested plants | Yield per plant (g) | CK = ZH11-TC P value | P ≤ 0.1 | CK = DP0158 P value | P ≤ 0.1 |
|---|---|---|---|---|---|---|---|
| DP0063.01 | 38 | 20 | 42.65 | 0.237 | | 0.755 | |
| DP0063.02 | 35 | 21 | 45.56 | 0.909 | | 0.168 | |
| DP0063.04 | 40 | 23 | 45.04 | 0.760 | | 0.235 | |
| DP0063.05 | 38 | 17 | 41.93 | 0.177 | | 0.964 | |
| DP0063.06 | 40 | 24 | 44.65 | 0.655 | | 0.298 | |
| DP0063.08 | 38 | 23 | 39.48 | 0.019 | | 0.393 | |
| DP0063.09 | 39 | 24 | 43.58 | 0.398 | | 0.513 | |
| DP0063.10 | 37 | 24 | 43.56 | 0.396 | | 0.517 | |
| DP0063.13 | 40 | 23 | 44.33 | 0.571 | | 0.351 | |
| DP0063.15 | 40 | 23 | 46.95 | 0.689 | | 0.058 | Y |
| DP0063.16 | 34 | 21 | 41.73 | 0.126 | | 0.978 | |
| ZH11-TC | 40 | 23 | 45.87 | | | | |
| DP0158 | 40 | 24 | 41.80 | | | | |
| DP0063 (construct) | | | 43.59 | 0.201 | | 0.317 | |

TABLE 53

Flag leaf SPAD value analysis of OsDN-LTP7 transgenic rice under field low nitrogen condition

| Line ID | Number of survival plants | Number of measured plants | SPAD value | CK = ZH11-TC P value | P ≤ 0.1 | CK = DP0158 P value | P ≤ 0.1 |
|---|---|---|---|---|---|---|---|
| DP0063.01 | 37 | 12 | 40.33 | 0.053 | Y | 0.117 | |
| DP0063.02 | 38 | 12 | 39.56 | 0.394 | | 0.625 | |
| DP0063.04 | 40 | 12 | 41.30 | 0.001 | Y | 0.004 | Y |
| DP0063.05 | 39 | 12 | 40.41 | 0.042 | Y | 0.095 | Y |
| DP0063.06 | 39 | 12 | 40.42 | 0.040 | Y | 0.091 | Y |
| DP0063.08 | 38 | 12 | 40.89 | 0.007 | Y | 0.020 | Y |
| DP0063.09 | 40 | 12 | 40.44 | 0.034 | Y | 0.078 | Y |
| DP0063.10 | 39 | 12 | 39.96 | 0.158 | | 0.294 | |
| DP0063.13 | 39 | 12 | 40.85 | 0.008 | Y | 0.022 | Y |
| DP0063.15 | 38 | 12 | 40.09 | 0.103 | | 0.208 | |
| DP0063.16 | 30 | 12 | 40.56 | 0.029 | Y | 0.066 | Y |
| ZH11-TC | 39 | 12 | 38.95 | | | | |
| DP0158 | 38 | 12 | 39.21 | | | | |
| DP0063 (construct) | | | 40.44 | 0.007 | Y | 0.025 | Y |

TABLE 54

Top second leaf SPAD value analysis of OsDN-LTP7 transgenic rice under field low nitrogen condition

| Line ID | Number of survival plants | Number of measured plants | SPAD value | CK = ZH11-TC P value | P ≤ 0.1 | CK = DP0158 P value | P ≤ 0.1 |
|---|---|---|---|---|---|---|---|
| DP0063.01 | 37 | 12 | 38.80 | 0.160 | | 0.247 | |
| DP0063.02 | 38 | 12 | 38.16 | 0.504 | | 0.671 | |
| DP0063.04 | 40 | 12 | 39.46 | 0.032 | Y | 0.056 | Y |
| DP0063.05 | 39 | 12 | 38.81 | 0.160 | | 0.245 | |
| DP0063.06 | 39 | 12 | 38.91 | 0.128 | | 0.201 | |
| DP0063.08 | 38 | 12 | 39.61 | 0.021 | Y | 0.038 | Y |
| DP0063.09 | 40 | 12 | 38.60 | 0.232 | | 0.341 | |
| DP0063.10 | 39 | 12 | 38.54 | 0.272 | | 0.393 | |
| DP0063.13 | 39 | 12 | 39.44 | 0.034 | Y | 0.061 | Y |
| DP0063.15 | 38 | 12 | 38.43 | 0.319 | | 0.455 | |
| DP0063.16 | 30 | 12 | 39.05 | 0.100 | Y | 0.158 | |

TABLE 54-continued

Top second leaf SPAD value analysis of OsDN-LTP7 transgenic
rice under field low nitrogen condition

| Line ID | Number of survival plants | Number of measured plants | SPAD value | CK = ZH11-TC P value | P ≤ 0.1 | CK = DP0158 P value | P ≤ 0.1 |
|---|---|---|---|---|---|---|---|
| ZH11-TC | 39 | 12 | 37.57 | | | | |
| DP0158 | 38 | 12 | 37.79 | | | | |
| DP0063 (construct) | | | 38.89 | 0.055 | Y | 0.107 | |

3) Field NUE Validation Results of OsBAK1L (DP0066) Transgenic Rice

The grain yield per plant, biomass, effective panicle number, plant height and SPAD values of OsBAK1L transgenic rice plants were measured. Table 55 shows that OsBAK1L transgenic rice exhibited less grain yield per plant than ZH11-TC and more grain yield than DP0158 controls at the construct level; and eight lines showed greater grain yield per plant than ZH11-TC control and all the twelve lines showed greater grain yield per plant than DP0158 control at the transgenic line level under low nitrogen conditions. Table 56 shows that the OsBAK1L transgenic rice exhibited significantly greater grain yield per plant than either ZH11-TC control or DP0158 control at the construct level; and ten lines exhibited greater grain yields per plant than ZH11-TC control and all the twelve exhibited greater grain yield per plant than DP0158 control at the transgenic line level under field normal nitrogen conditions. The OsBAK1L transgenic rice exhibited 8% grain yield increase than DP0158 control under low nitrogen conditions; and exhibited 6% and 14% grain yield increase than ZH11-TC control and DP0158 control under field normal nitrogen conditions irrespectively. These results demonstrate that OsBAK1L transgenic rice did not obtain low nitrogen tolerance as reflected by grain yield per plant.

The OsBAK1L transgenic rice plants were significantly shorter than ZH11-TC control and shorter than DP0158 control at the construct level under low nitrogen conditions; and were significantly shorter than ZH11-TC control and shorter than DP0158 control at the construct level under normal nitrogen conditions. These results indicate that the plant heights of OsBAK1L transgenic rice plants were not affected by the nitrogen level.

The table 57 shows that the OsBAK1L transgenic rice plants exhibited significantly greater effective panicle number than either ZH11-TC or DP0158 control at the construct level; and all the twelve lines exhibited greater effective panicle number than either ZH11-TC or DP0158 control at the transgenic line level under low nitrogen conditions. Under normal nitrogen conditions, the effective panicle number of the OsBAK1L transgenic rice plants was also significantly greater than ZH11-TC and DP0158 controls (Table 58). These results demonstrate that OsBAK1L transgenic rice plants exhibited enhanced low nitrogen tolerance and/or NUE under low nitrogen conditions as reflected by the effective panicle number.

There was no significant difference between the OsBAK1L transgenic rice and control for biomass, the flag leaf SPAD value and top second leaf SPAD value.

These results indicate that OsBAK1L transgenic rice plants obtained greater grain yield per plant and effective panicle number under normal nitrogen condition, and obtained more effective panicle number under low nitrogen conditions. Over-expression of OsBAK1L may improve low nitrogen tolerance and/or NUE.

TABLE 55

Grain yield analysis of OsBAK1L transgenic
rice under field low nitrogen condition

| Line ID | Number of survival plants | Number of harvested plants | Yield per plant (g) | CK = ZH11-TC P value | P ≤ 0.1 | CK = DP0158 P value | P ≤ 0.1 |
|---|---|---|---|---|---|---|---|
| DP0066.01 | 39 | 23 | 34.01 | 0.514 | | 0.072 | Y |
| DP0066.03 | 39 | 23 | 33.43 | 0.698 | | 0.124 | |
| DP0066.04 | 39 | 24 | 33.46 | 0.689 | | 0.123 | |
| DP0066.05 | 38 | 20 | 31.72 | 0.691 | | 0.456 | |
| DP0066.06 | 28 | 8 | 32.96 | 0.878 | | 0.240 | |
| DP0066.07 | 39 | 24 | 30.43 | 0.323 | | 0.875 | |
| DP0066.08 | 37 | 17 | 32.76 | 0.939 | | 0.221 | |
| DP0066.11 | 38 | 22 | 32.11 | 0.827 | | 0.353 | |
| DP0066.12 | 29 | 17 | 32.78 | 0.944 | | 0.307 | |
| DP0066.13 | 37 | 23 | 31.36 | 0.592 | | 0.579 | |
| DP0066.14 | 38 | 18 | 32.67 | 0.972 | | 0.262 | |
| DP0066.15 | 36 | 10 | 32.61 | 0.992 | | 0.248 | |
| ZH11-TC | 40 | 24 | 32.59 | | | | |
| DP0158 | 40 | 24 | 30.09 | | | | |
| DP0066 (construct) | | | 32.53 | 0.969 | | 0.138 | |

TABLE 56

Grain yield analysis of OsBAK1L transgenic rice under field normal nitrogen condition

| Line ID | Number of survival plants | Number of harvested plants | Yield per plant (g) | CK = ZH11-TC P value | P ≤ 0.1 | CK = DP0158 P value | P ≤ 0.1 |
|---|---|---|---|---|---|---|---|
| DP0066.01 | 40 | 23 | 48.65 | 0.304 | | 0.011 | Y |
| DP0066.03 | 40 | 24 | 47.81 | 0.472 | | 0.026 | Y |
| DP0066.04 | 35 | 24 | 47.02 | 0.671 | | 0.054 | Y |
| DP0066.05 | 38 | 22 | 48.40 | 0.351 | | 0.015 | Y |
| DP0066.06 | 23 | 11 | 50.16 | 0.136 | | 0.004 | Y |
| DP0066.07 | 37 | 18 | 50.77 | 0.070 | Y | 0.001 | Y |
| DP0066.08 | 29 | 15 | 49.41 | 0.219 | | 0.008 | Y |
| DP0066.11 | 39 | 20 | 47.93 | 0.447 | | 0.024 | Y |
| DP0066.12 | 32 | 9 | 54.34 | 0.002 | Y | 0.000 | Y |
| DP0066.13 | 40 | 23 | 51.48 | 0.038 | Y | 0.000 | Y |
| DP0066.14 | 36 | 20 | 45.40 | 0.862 | | 0.183 | |
| DP0066.15 | 33 | 15 | 43.42 | 0.367 | | 0.551 | |
| ZH11-TC | 40 | 24 | 45.87 | | | | |
| DP0158 | 40 | 24 | 41.80 | | | | |
| DP0066 (construct) | | | 48.73 | 0.097 | Y | 0.000 | Y |

TABLE 57

The effective panicle number analysis of OsBAK1L transgenic rice under field low nitrogen condition

| Line ID | Number of survival plants | Number of harvested plants | Panicle number | CK = ZH11-TC P value | P ≤ 0.1 | CK = DP0158 P value | P ≤ 0.1 |
|---|---|---|---|---|---|---|---|
| DP0066.01 | 39 | 23 | 7.91 | 0.003 | Y | 0.024 | Y |
| DP0066.03 | 39 | 23 | 7.83 | 0.005 | Y | 0.038 | Y |
| DP0066.04 | 39 | 24 | 7.89 | 0.003 | Y | 0.027 | Y |
| DP0066.05 | 38 | 20 | 7.04 | 0.330 | | 0.816 | |
| DP0066.06 | 28 | 8 | 7.77 | 0.016 | Y | 0.082 | Y |
| DP0066.07 | 39 | 24 | 7.04 | 0.331 | | 0.818 | |
| DP0066.08 | 37 | 17 | 7.50 | 0.042 | Y | 0.195 | |
| DP0066.11 | 38 | 22 | 7.42 | 0.065 | Y | 0.270 | |
| DP0066.12 | 29 | 17 | 7.83 | 0.017 | Y | 0.079 | Y |
| DP0066.13 | 37 | 23 | 7.63 | 0.019 | Y | 0.110 | |
| DP0066.14 | 38 | 18 | 7.18 | 0.216 | | 0.598 | |
| DP0066.15 | 36 | 10 | 8.50 | 0.000 | Y | 0.000 | Y |
| ZH11-TC | 40 | 24 | 6.62 | | | | |
| DP0158 | 40 | 24 | 6.94 | | | | |
| DP0066 (construct) | | | 7.63 | 0.002 | Y | 0.034 | Y |

TABLE 58

The effective panicle number analysis of OsBAK1L transgenic rice under field normal nitrogen condition

| Line ID | Number of survival plants | Number of harvested plants | Panicle | CKZH11-TC P value | P ≤ 0.1 | CK = DP0158 P value | P ≤ 0.1 |
|---|---|---|---|---|---|---|---|
| DP0066.01 | 40 | 23 | 13.46 | 0.033 | Y | 0.076 | Y |
| DP0066.03 | 40 | 24 | 12.99 | 0.158 | | 0.290 | |
| DP0066.04 | 35 | 24 | 13.43 | 0.037 | Y | 0.085 | Y |
| DP0066.05 | 38 | 22 | 13.03 | 0.140 | | 0.260 | |
| DP0066.06 | 23 | 11 | 13.07 | 0.136 | | 0.251 | |
| DP0066.07 | 37 | 18 | 13.54 | 0.025 | Y | 0.060 | Y |
| DP0066.08 | 29 | 15 | 13.17 | 0.102 | | 0.196 | |
| DP0066.11 | 39 | 20 | 12.72 | 0.311 | | 0.511 | |
| DP0066.12 | 32 | 9 | 13.48 | 0.032 | Y | 0.073 | Y |

TABLE 58-continued

The effective panicle number analysis of OsBAK1L transgenic rice under field normal nitrogen condition

| Line ID | Number of survival plants | Number of harvested plants | Panicle | CKZH11-TC P value | P ≤ 0.1 | CK = DP0158 P value | P ≤ 0.1 |
|---|---|---|---|---|---|---|---|
| DP0066.13 | 40 | 23 | 13.75 | 0.011 | Y | 0.027 | Y |
| DP0066.14 | 36 | 20 | 12.64 | 0.372 |   | 0.593 |   |
| DP0066.15 | 33 | 15 | 12.98 | 0.162 |   | 0.296 |   |
| ZH11-TC | 40 | 24 | 12.04 |   |   |   |   |
| DP0158 | 40 | 24 | 12.28 |   |   |   |   |
| DP0066 (construct) |   |   | 13.19 | 0.020 | Y | 0.065 | Y |

4) Field NUE Validation Results of OsEIL2 (DP0069) Transgenic Rice

The grain yield per plant, biomass, effective panicle number and plant height of OsEIL2 transgenic rice plants were measured. Table 59 shows that OsEIL2 transgenic rice exhibited greater grain yield per plant than ZH11-TC control and significantly greater grain yield per plant than DP0158 control at the construct level; and nine lines showed greater grain yield per plant than ZH11-TC control and all the eleven lines showed greater grain yield per plant than DP0158 control at the transgenic line level under low nitrogen conditions. Table 60 shows that the OsEIL2 transgenic rice exhibited significantly greater grain yield per plant than ZH11-TC control and DP0158 control at the construct level; and eleven lines exhibited greater grain yields per plant than either ZH11-TC or DP0158 control at the transgenic line level under field normal nitrogen conditions. The OsEIL2 transgenic rice exhibited 5% and 12% grain yield increase than ZH11-TC and DP0158 control under low nitrogen conditions, respectively; and exhibited 9% and 17% grain yield increase than ZH11-TC control and DP0158 control under field normal nitrogen conditions, respectively. These results demonstrate that OsEIL2 transgenic rice obtained low nitrogen tolerance, and over-expression of OsEIL2 improves the grain yield of transgenic plants under low nitrogen conditions.

The table 61 shows that the OsEIL2 transgenic rice plants exhibited greater effective panicle number than either ZH11-TC or DP0158 control at the construct level; and nine lines exhibited greater effective panicle number than either ZH11-TC or DP0158 control at the transgenic line level under low nitrogen conditions. Under normal nitrogen conditions, the effective panicle number of the OsEIL2 transgenic rice plants was significantly greater than ZH11-TC and DP0158 controls (Table 62). These results demonstrate that OsEIL2 transgenic rice plants exhibited more effective panicle number under normal nitrogen conditions.

There was no significant difference between the OsEIL2 transgenic rice and control for the flag leaf SPAD value and top second leaf SPAD value.

These results indicate that OsEIL2 transgenic rice plants obtained greater grain yield per plant and more panicle number under normal nitrogen conditions, and gained more grain yield per plant under low nitrogen conditions; overexpression of OsEIL2 improves the grain yield per plant under low nitrogen conditions. OsEIL2 gene plays a role in enhancing low nitrogen tolerance and/or NUE.

TABLE 59

Grain yield analysis of OsEIL2 transgenic rice under field low nitrogen condition

| Line ID | Number of survival plants | Number of harvested plants | Yield per plant (g) | CK = ZH11-TC P value | P ≤ 0.1 | CK = DP0158 P value | P ≤ 0.1 |
|---|---|---|---|---|---|---|---|
| DP0069.01 | 40 | 24 | 33.55 | 0.655 |   | 0.111 |   |
| DP0069.02 | 38 | 22 | 32.12 | 0.832 |   | 0.351 |   |
| DP0069.03 | 40 | 23 | 34.19 | 0.460 |   | 0.060 | Y |
| DP0069.05 | 39 | 21 | 34.44 | 0.392 |   | 0.046 | Y |
| DP0069.07 | 40 | 23 | 32.83 | 0.908 |   | 0.208 |   |
| DP0069.08 | 39 | 23 | 33.98 | 0.521 |   | 0.075 | Y |
| DP0069.09 | 40 | 24 | 35.70 | 0.154 |   | 0.010 | Y |
| DP0069.10 | 30 | 18 | 35.35 | 0.227 |   | 0.022 | Y |
| DP0069.11 | 39 | 20 | 32.88 | 0.890 |   | 0.202 |   |
| DP0069.12 | 38 | 22 | 34.91 | 0.283 |   | 0.027 | Y |
| DP0069.15 | 40 | 18 | 31.35 | 0.574 |   | 0.565 |   |
| ZH11-TC | 40 | 24 | 32.59 |   |   |   |   |
| DP0158 | 40 | 21 | 30.09 |   |   |   |   |
| DP0069 (construct) |   |   | 33.76 | 0.473 |   | 0.025 | Y |

TABLE 60

Grain yield analysis of OsEIL2 transgenic rice under field normal nitrogen condition

| Line ID | Number of survival plants | Number of harvested plants | Yield per plant (g) | CK = ZH11-TC P value | P ≤ 0.1 | CK = DP0158 P value | P ≤ 0.1 |
|---|---|---|---|---|---|---|---|
| DP0069.01 | 34 | 20 | 46.35 | 0.858 | | 0.093 | Y |
| DP0069.02 | 33 | 20 | 48.44 | 0.346 | | 0.015 | Y |
| DP0069.03 | 30 | 18 | 51.02 | 0.076 | Y | 0.002 | Y |
| DP0069.05 | 37 | 19 | 51.13 | 0.070 | Y | 0.001 | Y |
| DP0069.07 | 40 | 19 | 49.91 | 0.164 | | 0.005 | Y |
| DP0069.08 | 39 | 21 | 49.91 | 0.138 | | 0.003 | Y |
| DP0069.09 | 36 | 22 | 52.02 | 0.024 | Y | 0.000 | Y |
| DP0069.10 | 28 | 18 | 50.91 | 0.084 | Y | 0.002 | Y |
| DP0069.11 | 38 | 14 | 49.40 | 0.194 | | 0.005 | Y |
| DP0069.12 | 38 | 16 | 52.62 | 0.013 | Y | 0.000 | Y |
| DP0069.15 | 39 | 21 | 51.37 | 0.043 | Y | 0.000 | Y |
| ZH11-TC | 39 | 23 | 45.87 | | | | |
| DP0158 | 40 | 23 | 41.80 | | | | |
| DP0069 (construct) | | | 50.28 | 0.015 | Y | 0.000 | Y |

TABLE 61

The effective panicle number analysis of OsEIL2 transgenic rice under field low nitrogen condition

| Line ID | Number of survival plants | Number of harvested plants | Panicle | CK = ZH11-TC P value | P ≤ 0.1 | CK = DP0158 P value | P ≤ 0.1 |
|---|---|---|---|---|---|---|---|
| DP0069.01 | 40 | 24 | 6.94 | 0.457 | | 0.999 | |
| DP0069.02 | 38 | 22 | 7.17 | 0.205 | | 0.600 | |
| DP0069.03 | 40 | 23 | 7.47 | 0.049 | Y | 0.220 | |
| DP0069.05 | 39 | 21 | 7.05 | 0.316 | | 0.792 | |
| DP0069.07 | 40 | 23 | 6.83 | 0.631 | | 0.795 | |
| DP0069.08 | 39 | 23 | 7.32 | 0.107 | | 0.383 | |
| DP0069.09 | 40 | 24 | 7.26 | 0.137 | | 0.457 | |
| DP0069.10 | 30 | 18 | 7.16 | 0.234 | | 0.630 | |
| DP0069.11 | 39 | 20 | 7.03 | 0.350 | | 0.845 | |
| DP0069.12 | 38 | 22 | 7.39 | 0.075 | Y | 0.299 | |
| DP0069.15 | 40 | 18 | 7.22 | 0.165 | | 0.518 | |
| DP0069.16 | 35 | 9 | 6.57 | 0.915 | | 0.416 | |
| ZH11-TC | 40 | 24 | 6.62 | | | | |
| DP0158 | 40 | 21 | 6.94 | | | | |
| DP0069 (construct) | | | 7.12 | 0.122 | | 0.583 | |

TABLE 62

The effective panicle number analysis of OsEIL2 transgenic rice under field normal nitrogen condition

| Line ID | Number of survival plants | Number of harvested plants | Panicle | CK = ZH11-TC P value | P ≤ 0.1 | CK = DP0158 P value | P ≤ 10.1 |
|---|---|---|---|---|---|---|---|
| DP0069.01 | 34 | 20 | 13.20 | 0.085 | Y | 0.173 | |
| DP0069.02 | 33 | 20 | 14.31 | 0.001 | Y | 0.002 | Y |
| DP0069.03 | 30 | 18 | 13.90 | 0.008 | Y | 0.020 | Y |
| DP0069.05 | 37 | 19 | 13.86 | 0.009 | Y | 0.023 | Y |
| DP0069.07 | 40 | 19 | 13.62 | 0.023 | Y | 0.054 | Y |
| DP0069.08 | 39 | 21 | 13.80 | 0.009 | Y | 0.024 | Y |
| DP0069.09 | 36 | 22 | 13.77 | 0.010 | Y | 0.026 | Y |
| DP0069.10 | 28 | 18 | 13.76 | 0.014 | Y | 0.034 | Y |
| DP0069.11 | 38 | 14 | 13.51 | 0.029 | Y | 0.068 | Y |
| DP0069.12 | 38 | 16 | 14.21 | 0.001 | Y | 0.004 | Y |

TABLE 62-continued

The effective panicle number analysis of OsEIL2 transgenic rice under field normal nitrogen condition

| Line ID | Number of survival plants | Number of harvested plants | Panicle | CK = ZH11-TC | | CK = DP0158 | |
| --- | --- | --- | --- | --- | --- | --- | --- |
| | | | | P value | P ≤ 0.1 | P value | P ≤ 10.1 |
| DP0069.15 | 39 | 21 | 14.55 | 0.000 | Y | 0.001 | Y |
| ZH11-TC | 39 | 23 | 12.04 | | | | |
| DP0158 | 40 | 23 | 12.28 | | | | |
| DP0069 (construct) | | | 13.86 | 0.000 | Y | 0.002 | Y |

5) Field NUE Validation Results of OsPPO3 (DP0097) Transgenic Rice

The grain yield per plant, biomass, effective panicle number and plant height of OsPPO3 transgenic rice plants were measured. Table 63 shows that OsPPO3 transgenic rice exhibited less grain yield per plant than ZH11-TC control and greater grain yield per plant than DP0158 control at the construct level under low nitrogen conditions. Table 64 shows that the OsPPO3 transgenic rice exhibited greater grain yield per plant than ZH11-TC control and significantly greater grain yield per plant than DP0158 control at the construct level; and six lines exhibited greater grain yields per plant than ZH11-TC and all the twelve lines exhibited greater grain yield per plant than DP0158 control at the transgenic line level under field normal nitrogen conditions. These results demonstrate that OsPPO3 transgenic rice have more grain yield per plant than controls under normal nitrogen field and did not show low nitrogen tolerance under low nitrogen conditions.

Table 65 shows that the OsPPO3 transgenic rice plants exhibited greater flag leaf SPAD value than either ZH11-TC or DP0158 control at the construct level; and eleven lines exhibited greater flag leaf SPAD value than either ZH11-TC or DP0158 control at the transgenic line level under low nitrogen conditions. Table 66 shows that OsPPO3 transgenic rice plants exhibited significantly greater top second leaf SPAD value than ZH11-TC control and greater top second leaf SPAD value than DP0158 control at the construct level; and eleven lines exhibited greater top second leaf SPAD value than ZH11-TC control and eight lines exhibited greater top second leaf SPAD value than DP0158 control at the transgenic line level under low nitrogen conditions. These results demonstrate that OsPPO3 transgenic rice plants exhibited enhanced low nitrogen tolerance and/or NUE under low nitrogen conditions as reflected by the effective panicle number.

There was no significant difference between the OsPPO3 transgenic rice and control for biomass, plant height and effective panicle number.

These results indicate that OsPPO3 transgenic rice plants gained greater grain yield per plant under normal nitrogen conditions, greater SPAD value under low nitrogen conditions, over-expression of OsPPO3 improves transgenic plants to grow greener under low nitrogen conditions. OsPPO3 gene plays a role in enhancing low nitrogen tolerance and/or NUE.

TABLE 63

Grain yield analysis of OsPPO3 transgenic rice under field low nitrogen condition

| Line ID | Number of survival plants | Number of harvested plants | Yield per plant (g) | CK = ZH11-TC | | CK = DP0158 | |
| --- | --- | --- | --- | --- | --- | --- | --- |
| | | | | P value | P ≤ 0.1 | P value | P ≤ 0.1 |
| DP0097.03 | 40 | 24 | 28.12 | 0.473 | | 0.898 | |
| DP0097.06 | 40 | 23 | 30.43 | 0.628 | | 0.183 | |
| DP0097.11 | 40 | 24 | 27.88 | 0.395 | | 0.999 | |
| DP0097.12 | 40 | 24 | 27.94 | 0.416 | | 0.974 | |
| DP0097.18 | 29 | 16 | 29.66 | 0.939 | | 0.383 | |
| DP0097.21 | 40 | 24 | 32.24 | 0.152 | | 0.023 | Y |
| DP0097.22 | 39 | 20 | 25.57 | 0.040 | | 0.230 | |
| DP0097.24 | 39 | 19 | 31.19 | 0.380 | | 0.085 | Y |
| DP0097.33 | 38 | 24 | 27.39 | 0.270 | | 0.799 | |
| DP0097.34 | 38 | 22 | 26.93 | 0.180 | | 0.622 | |
| DP0097.35 | 33 | 18 | 29.34 | 0.933 | | 0.445 | |
| DP0097.36 | 37 | 18 | 28.74 | 0.691 | | 0.654 | |
| ZH11-TC | 40 | 24 | 29.50 | | | | |
| DP0158 | 40 | 24 | 27.88 | | | | |
| DP0097 (construct) | | | 28.79 | 0.598 | | 0.505 | |

TABLE 64

Grain yield analysis of OsPPO3 transgenic rice under field normal nitrogen condition

| Line ID | Number of survival plants | Number of harvested plants | Yield per plant (g) | CK = ZH11-TC P value | P ≤ 0.1 | CK = DP0158 P value | P ≤ 0.1 |
|---|---|---|---|---|---|---|---|
| DP0097.03 | 39 | 24 | 43.24 | 0.879 | | 0.119 | |
| DP0097.06 | 39 | 22 | 47.06 | 0.164 | | 0.002 | Y |
| DP0097.11 | 40 | 23 | 41.50 | 0.390 | | 0.395 | |
| DP0097.12 | 40 | 24 | 46.84 | 0.190 | | 0.002 | Y |
| DP0097.18 | 18 | 9 | 43.47 | 0.952 | | 0.100 | |
| DP0097.21 | 40 | 24 | 45.00 | 0.573 | | 0.023 | Y |
| DP0097.22 | 33 | 12 | 43.28 | 0.899 | | 0.144 | |
| DP0097.24 | 31 | 15 | 40.09 | 0.152 | | 0.780 | |
| DP0097.33 | 35 | 24 | 44.63 | 0.681 | | 0.034 | Y |
| DP0097.34 | 40 | 22 | 49.55 | 0.016 | Y | 0.000 | Y |
| DP0097.35 | 23 | 13 | 42.23 | 0.634 | | 0.329 | |
| DP0097.36 | 39 | 16 | 45.88 | 0.362 | | 0.009 | Y |
| ZH11-TC | 39 | 24 | 43.62 | | | | |
| DP0158 | 40 | 24 | 39.40 | | | | |
| DP0097 (construct) | | | 44.40 | 0.624 | | 0.002 | Y |

TABLE 65

Flag leaf SPAD value analysis of OsPPO3 transgenic rice under field low nitrogen condition

| Line ID | Number of survival plants | Number of measured plants | SPAD value | CK = ZH11-TC P value | P ≤ 0.1 | CK = DP0158 P value | P ≤ 0.1 |
|---|---|---|---|---|---|---|---|
| DP0097.03 | 40 | 12 | 41.01 | 0.044 | Y | 0.072 | Y |
| DP0097.06 | 40 | 12 | 40.72 | 0.107 | | 0.162 | |
| DP0097.11 | 40 | 12 | 39.84 | 0.639 | | 0.799 | |
| DP0097.12 | 40 | 12 | 39.50 | 0.985 | | 0.843 | |
| DP0097.18 | 29 | 12 | 41.67 | 0.004 | Y | 0.008 | Y |
| DP0097.21 | 40 | 12 | 40.89 | 0.066 | Y | 0.105 | |
| DP0097.22 | 39 | 12 | 39.76 | 0.719 | | 0.886 | |
| DP0097.24 | 39 | 12 | 40.81 | 0.076 | Y | 0.120 | |
| DP0097.33 | 38 | 12 | 40.70 | 0.110 | | 0.165 | |
| DP0097.34 | 38 | 12 | 40.23 | 0.328 | | 0.445 | |
| DP0097.35 | 33 | 12 | 40.00 | 0.497 | | 0.643 | |
| DP0097.36 | 37 | 12 | 40.15 | 0.370 | | 0.498 | |
| ZH11-TC | 40 | 12 | 39.48 | | | | |
| DP0158 | 40 | 12 | 39.65 | | | | |
| DP0097 (construct) | | | 40.44 | 0.108 | | 0.183 | |

TABLE 66

Top second leaf SPAD value analysis of OsPPO3 transgenic rice under field low nitrogen condition

| Line ID | Number of survival plants | Number of measured plants | SPAD value | CK = ZH11-TC P value | P ≤ 0.1 | CK = DP0158 P value | P ≤ 0.1 |
|---|---|---|---|---|---|---|---|
| DP0097.03 | 40 | 12 | 39.98 | 0.004 | Y | 0.072 | Y |
| DP0097.06 | 40 | 12 | 39.10 | 0.068 | Y | 0.428 | |
| DP0097.11 | 40 | 12 | 38.08 | 0.491 | | 0.730 | |
| DP0097.12 | 40 | 12 | 39.00 | 0.082 | Y | 0.488 | |
| DP0097.18 | 29 | 12 | 39.76 | 0.010 | Y | 0.123 | |
| DP0097.21 | 40 | 12 | 40.22 | 0.002 | Y | 0.041 | Y |
| DP0097.22 | 39 | 12 | 37.91 | 0.611 | | 0.593 | |
| DP0097.24 | 39 | 12 | 39.57 | 0.017 | Y | 0.178 | |
| DP0097.33 | 38 | 12 | 38.56 | 0.214 | | 0.841 | |

TABLE 66-continued

Top second leaf SPAD value analysis of OsPPO3 transgenic rice under field low nitrogen condition

| Line ID | Number of survival plants | Number of measured plants | SPAD value | CK = ZH11-TC P value | P ≤ 0.1 | CK = DP0158 P value | P ≤ 0.1 |
|---|---|---|---|---|---|---|---|
| DP0097.34 | 38 | 12 | 38.89 | 0.109 | | 0.573 | |
| DP0097.35 | 33 | 12 | 38.20 | 0.407 | | 0.835 | |
| DP0097.36 | 37 | 12 | 38.83 | 0.120 | | 0.615 | |
| ZH11-TC | 40 | 12 | 37.46 | | | | |
| DP0158 | 40 | 12 | 38.39 | | | | |
| DP0097 (construct) | | | 39.01 | 0.020 | Y | 0.348 | |

6) Field NUE Validation Results of OsTTP1 (DP0299) Transgenic Rice

The grain yield per plant, biomass, effective panicle number and plant height of OsTTP1 transgenic rice plants were measured. Table 67 shows that OsTTP1 transgenic rice exhibited greater grain yield per plant than ZH11-TC control and significantly greater grain yield per plant than DP0158 control at the construct level; and nine lines showed greater grain yield per plant than ZH11-TC control and eleven lines showed greater grain yield per plant than DP0158 control at the transgenic line level under low nitrogen conditions. Table 68 shows that the OsTTP1 transgenic rice exhibited less grain yield per plant than ZH11-TC control and greater grain yield per plant than DP0158 control at the construct level; and two lines exhibited greater grain yields per plant than ZH11-TC and seven lines exhibited greater grain yields per plant than DP0158 control at the transgenic line level under field normal nitrogen conditions. The OsTTP1 transgenic rice exhibited 2% and 10% grain yield increase per plant than ZH11-TC and DP0158 control under low nitrogen conditions, respectively; and exhibited 7% decrease and 2% increase in grain yield per plant than ZH11-TC control and DP0158 control under field normal nitrogen conditions, respectively. These results demonstrate that OsTTP1 transgenic rice obtained low nitrogen tolerance, and over-expression of OsTTP1 improves the grain yield per plant of transgenic plants under low nitrogen conditions.

Table 69 shows that the effective panicle number of OsTTP1 transgenic rice plants was significantly greater than ZH11-TC control and greater than DP0158 control at the construct level; and all the tested lines exhibited greater effective panicle number than either ZH11-TC or DP0158 control at the transgenic line level under low nitrogen conditions. Under normal nitrogen conditions, the effective panicle number of OsTTP1 transgenic rice plants was also significantly greater than ZH11-TC control and greater than DP0158 controls (Table 70). OsTTP1 transgenic rice exhibited 10% and 6% panicle number increase than ZH11-TC and DP0158 control under low nitrogen conditions; and 7% and 5% panicle number increase under normal nitrogen conditions. These results demonstrate that OsTTP1 transgenic rice plants exhibited same rate panicle number increase than controls under low nitrogen conditions and normal nitrogen conditions; the increase of panicle number may be affected by OsTTP1 gene, and not affected by nitrogen.

Table 71 shows that the OsTTP1 transgenic rice plants exhibited greater flag leaf SPAD value than either ZH11-TC or DP0158 control at the construct level; and ten lines exhibited greater flag leaf SPAD value than ZH11-TC and DP0158 controls at the transgenic line level under low nitrogen conditions. Table 72 shows that OsTTP1 transgenic rice plants exhibited significantly greater top second leaf SPAD value than ZH11-TC and DP0158 control at the construct level; and all the twelve lines exhibited greater top second leaf SPAD value than ZH11-TC and DP0158 control at the transgenic line level under low nitrogen conditions. These results demonstrate that OsTTP1 transgenic rice plants exhibited enhanced low nitrogen tolerance and/or NUE under low nitrogen conditions as reflected by the effective panicle number.

There was no significant difference between the OsTTP1 transgenic rice and control for biomass and plant height.

These results indicate that OsTTP1 transgenic rice plants obtained greater grain yield per plant, more effective panicle number and greater SPAD value under low nitrogen conditions, over-expression of OsTTP1 improves the effective panicle number and grow status of transgenic plants, then improves the grain yield per plant under low nitrogen conditions. OsTTP1 gene plays a role in enhancing low nitrogen tolerance and/or NUE.

TABLE 67

Grain yield analysis of OsTTP1 transgenic rice under field low nitrogen condition

| Line ID | Number of survival plants | Number of harvested plants | Yield per plant (g) | CK = ZH11-TC P value | P ≤ 0.1 | CK = DP0158 P value | P ≤ 0.1 |
|---|---|---|---|---|---|---|---|
| DP0299.02 | 30 | 17 | 33.73 | 0.617 | | 0.111 | |
| DP0299.03 | 30 | 18 | 31.98 | 0.790 | | 0.407 | |
| DP0299.04 | 40 | 23 | 33.69 | 0.611 | | 0.096 | Y |
| DP0299.05 | 40 | 22 | 32.68 | 0.965 | | 0.230 | |
| DP0299.06 | 30 | 18 | 34.56 | 0.388 | | 0.050 | Y |
| DP0299.07 | 40 | 24 | 32.06 | 0.807 | | 0.362 | |
| DP0299.09 | 40 | 23 | 35.79 | 0.139 | | 0.008 | Y |

TABLE 67-continued

Grain yield analysis of OsTTP1 transgenic rice under field low nitrogen condition

| Line ID | Number of survival plants | Number of harvested plants | Yield per plant (g) | CK = ZH11-TC P value | P ≤ 0.1 | CK = DP0158 P value | P ≤ 0.1 |
|---|---|---|---|---|---|---|---|
| DP0299.11 | 30 | 18 | 33.02 | 0.849 | | 0.198 | |
| DP0299.13 | 40 | 23 | 34.07 | 0.495 | | 0.066 | Y |
| DP0299.14 | 37 | 24 | 34.93 | 0.305 | | 0.033 | Y |
| DP0299.15 | 35 | 19 | 29.70 | 0.207 | | 0.866 | |
| DP0299.17 | 40 | 24 | 34.38 | 0.408 | | 0.047 | Y |
| ZH11-TC | 40 | 24 | 32.59 | | | | |
| DP0158 | 40 | 24 | 30.09 | | | | |
| DP0299 (construct) | | | 33.38 | 0.623 | | 0.041 | Y |

TABLE 68

Grain yield analysis of OsTTP1 transgenic rice under field normal nitrogen condition

| Line ID | Number of survival plants | Number of harvested plants | Yield per plant (g) | CK = ZH11-TC P value | P ≤ 0.1 | CK = DP0158 P value | P ≤ 10.1 |
|---|---|---|---|---|---|---|---|
| DP0299.02 | 30 | 18 | 43.08 | 0.334 | | 0.658 | |
| DP0299.03 | 10 | 6 | 39.71 | 0.072 | | 0.542 | |
| DP0299.04 | 40 | 23 | 41.36 | 0.095 | | 0.869 | |
| DP0299.05 | 35 | 20 | 45.80 | 0.979 | | 0.141 | |
| DP0299.06 | 30 | 18 | 45.74 | 0.965 | | 0.173 | |
| DP0299.07 | 40 | 24 | 43.25 | 0.331 | | 0.594 | |
| DP0299.09 | 40 | 24 | 46.05 | 0.947 | | 0.116 | |
| DP0299.11 | 28 | 18 | 40.60 | 0.068 | | 0.677 | |
| DP0299.13 | 40 | 23 | 39.07 | 0.012 | | 0.311 | |
| DP0299.14 | 38 | 24 | 44.74 | 0.677 | | 0.277 | |
| DP0299.15 | 33 | 16 | 37.29 | 0.002 | | 0.098 | |
| DP0299.17 | 33 | 20 | 46.14 | 0.920 | | 0.109 | |
| ZH11-TC | 40 | 24 | 45.87 | | | | |
| DP0158 | 40 | 25 | 41.80 | | | | |
| DP0299 (construct) | | | 42.74 | 0.075 | | 0.596 | |

TABLE 69

Effective panicle number analysis of OsTTP1 transgenic rice under field low nitrogen condition

| Line ID | Number of survival plants | Number of harvested plants | Panicle number | CK = ZH11-TC P value | P ≤ 0.1 | CK = DP0158 P value | P ≤ 0.1 |
|---|---|---|---|---|---|---|---|
| DP0299.02 | 30 | 17 | 7.48 | 0.058 | Y | 0.235 | |
| DP0299.03 | 30 | 18 | 7.30 | 0.133 | | 0.425 | |
| DP0299.04 | 40 | 23 | 7.62 | 0.021 | Y | 0.115 | |
| DP0299.05 | 40 | 22 | 7.24 | 0.151 | | 0.487 | |
| DP0299.06 | 30 | 18 | 7.40 | 0.084 | Y | 0.307 | |
| DP0299.07 | 40 | 24 | 7.15 | 0.223 | | 0.632 | |
| DP0299.09 | 40 | 23 | 7.52 | 0.038 | Y | 0.181 | |
| DP0299.11 | 30 | 18 | 7.24 | 0.172 | | 0.509 | |
| DP0299.13 | 40 | 23 | 7.55 | 0.032 | Y | 0.159 | |
| DP0299.14 | 37 | 24 | 7.20 | 0.178 | | 0.544 | |
| DP0299.15 | 35 | 19 | 7.10 | 0.270 | | 0.716 | |
| DP0299.17 | 40 | 24 | 7.77 | 0.008 | Y | 0.053 | Y |
| ZH11-TC | 40 | 24 | 6.62 | | | | |
| DP0158 | 40 | 24 | 6.94 | | | | |
| DP0299 (construct) | | | 7.38 | 0.019 | Y | 0.173 | |

TABLE 70

Effective panicle number analysis of OsTTP1 transgenic rice under field normal nitrogen condition

| Line ID | Number of survival plants | Number of harvested plants | Panicle number | CK = ZH11-TC P value | P ≤ 0.1 | CK = DP0158 P value | P ≤ 10.1 |
|---|---|---|---|---|---|---|---|
| DP0299.02 | 30 | 18 | 13.02 | 0.162 | | 0.290 | |
| DP0299.03 | 10 | 6 | 12.77 | 0.335 | | 0.518 | |
| DP0299.04 | 40 | 23 | 13.10 | 0.116 | | 0.223 | |
| DP0299.05 | 35 | 20 | 13.05 | 0.133 | | 0.251 | |
| DP0299.06 | 30 | 18 | 13.49 | 0.037 | Y | 0.081 | Y |
| DP0299.07 | 40 | 24 | 12.98 | 0.162 | | 0.298 | |
| DP0299.09 | 40 | 24 | 12.89 | 0.205 | | 0.362 | |
| DP0299.11 | 28 | 18 | 12.77 | 0.298 | | 0.484 | |
| DP0299.13 | 40 | 23 | 12.82 | 0.249 | | 0.425 | |
| DP0299.14 | 38 | 24 | 13.18 | 0.089 | Y | 0.178 | |
| DP0299.15 | 33 | 16 | 12.25 | 0.759 | | 0.962 | |
| DP0299.17 | 33 | 20 | 13.19 | 0.087 | Y | 0.176 | |
| ZH11-TC | 40 | 24 | 12.04 | | | | |
| DP0158 | 40 | 25 | 12.28 | | | | |
| DP0299 (construct) | | | 12.96 | 0.068 | Y | 0.177 | |

TABLE 71

Flag leaf SPAD value analysis of OsTTP1 transgenic rice under field low nitrogen condition

| Line ID | Number of survival plants | Number of harvested plants | SPAD value | CK = ZH11-TC P value | P ≤ 0.1 | CK = DP0158 P value | P ≤ 0.1 |
|---|---|---|---|---|---|---|---|
| DP0299.02 | 30 | 12 | 39.61 | 0.382 | | 0.597 | |
| DP0299.03 | 30 | 12 | 39.06 | 0.883 | | 0.849 | |
| DP0299.04 | 40 | 12 | 39.35 | 0.578 | | 0.843 | |
| DP0299.05 | 40 | 12 | 39.69 | 0.312 | | 0.513 | |
| DP0299.06 | 30 | 12 | 39.33 | 0.618 | | 0.872 | |
| DP0299.07 | 40 | 12 | 40.96 | 0.006 | Y | 0.018 | Y |
| DP0299.09 | 40 | 12 | 40.17 | 0.098 | Y | 0.195 | |
| DP0299.11 | 30 | 12 | 39.67 | 0.352 | | 0.554 | |
| DP0299.13 | 40 | 12 | 38.83 | 0.873 | | 0.608 | |
| DP0299.14 | 37 | 12 | 39.89 | 0.194 | | 0.348 | |
| DP0299.15 | 35 | 12 | 40.81 | 0.010 | Y | 0.026 | Y |
| DP0299.17 | 40 | 12 | 39.79 | 0.248 | | 0.428 | |
| ZH11-TC | 40 | 12 | 38.95 | | | | |
| DP0158 | 40 | 12 | 39.21 | | | | |
| DP0299 (construct) | | | 39.76 | 0.153 | | 0.333 | |

TABLE 72

Top second leaf SPAD value analysis of OsTTP1 transgenic rice under field low nitrogen condition

| Line ID | Number of survival plants | Number of harvested plants | SPAD value | CK = ZH11-TC P value | P ≤ 0.1 | CK = DP0158 P value | P ≤ 10.1 |
|---|---|---|---|---|---|---|---|
| DP0299.02 | 30 | 12 | 38.98 | 0.129 | | 0.198 | |
| DP0299.03 | 30 | 12 | 38.39 | 0.382 | | 0.518 | |
| DP0299.04 | 40 | 12 | 39.19 | 0.069 | Y | 0.114 | |
| DP0299.05 | 40 | 12 | 39.21 | 0.067 | Y | 0.112 | |
| DP0299.06 | 30 | 12 | 39.32 | 0.061 | Y | 0.100 | Y |
| DP0299.07 | 40 | 12 | 40.53 | 0.001 | Y | 0.002 | Y |
| DP0299.09 | 40 | 12 | 39.91 | 0.009 | Y | 0.018 | Y |
| DP0299.11 | 30 | 12 | 38.48 | 0.334 | | 0.460 | |
| DP0299.13 | 40 | 12 | 37.86 | 0.751 | | 0.938 | |

TABLE 72-continued

Top second leaf SPAD value analysis of OsTTP1 transgenic rice under field low nitrogen condition

| Line ID | Number of survival plants | Number of harvested plants | SPAD value | CK = ZH11-TC P value | P ≤ 0.1 | CK = DP0158 P value | P ≤ 10.1 |
|---|---|---|---|---|---|---|---|
| DP0299.14 | 37 | 12 | 39.25 | 0.057 | Y | 0.096 | Y |
| DP0299.15 | 35 | 12 | 40.73 | 0.000 | Y | 0.001 | Y |
| DP0299.17 | 40 | 12 | 39.51 | 0.029 | Y | 0.052 | Y |
| ZH11-TC | 40 | 12 | 37.57 | | | | |
| DP0158 | 40 | 12 | 37.79 | | | | |
| DP0299 (construct) | | | 39.28 | 0.016 | Y | 0.034 | Y |

Example 7

Drought Tolerance Assay of Transgenic Rice Plants Under Greenhouse Conditions

In order to investigate whether the genes could improve drought tolerance in rice plants, the transgenic rice plants were tested in greenhouse drought assays.

Drought Screening Method:

$T_2$ Transgenic seeds were sterilized by 800 ppm carbendazol for 8 h at 32° C. and washed 3-5 times with distilled water, then soaked in water for 16 h at 32° C., germinated for 18 h at 35-37° C. in an incubator. The germinated seeds were sowed in tray filled with mixture of organic soil, vermiculite and sand (V:V:V=3:3:2). The seedlings were grown under normal greenhouse condition and watered by modified IRRI solution. When the seedlings grow to 3-leaf stage, watering was stopped and the trays were kept in a dry place until the leaves became dry and curved (approximately 9-15 days depending on the seasons). The trays were transferred into water pool to recover the seedlings for 5-7 days, and then plants were scored for the degree of recovery. The following scoring system was used: more than half green stem=1, more than two third green leaf=1, less than two third but more than one third green leaf=0.5, less than one third green leaf=0.2, no green leaf or less than half green stem=0. The recovery degree was the sum of the score of the green tissues, and the data were statistically analyzed using Mixed Model.

Randomized block design was used from construct level. Eight transgenic lines from the same construct were planted in one experimental unit to evaluate the gene at construct level by Mixed Model considering construct, line and environment effects. Survival rate (percentage of survived plants over the total plant number) was also used as a parameter for drought screening. If the survival rates or recovery degrees of the transgenic rice plants were significantly greater than control (P<0.05), the gene was considered having drought tolerant function.

GH Drought Assay Results:

Eight OsEIL2 transgenic rice lines, ZH11-TC and DP0158 seedlings were planted in one tray and repeated for four times. When the rice plants grow to 3-leaf stage, they were drought stressed for 16 or 17 days, and recovered in water for seven days. As shown in Table 73, 255 of the 377 OsEIL2 transgenic rice survived, while 39 of the 90 ZH11-TC and 57 of the 93 DP0158 seedlings survived. OsEIL2 transgenic rice exhibited higher survival rate and exhibited significantly higher average recovery degree than ZH11-TC at the construct level. Analysis at the line level showed that all the eight lines exhibited higher survival rates and average recovery degrees than ZH11-TC control, and five lines exhibited higher survival rates and average recovery degrees than DP0158 control (Table 74). These results indicated that OsEIL2 transgenic rice plants gained drought tolerance at seedling stage, and OsEIL2 plays a role in enhancing drought tolerance of transgenic plants.

TABLE 73

Enhanced drought tolerance of OsEIL2 transgenic rice plants under greenhouse conditions (construct level)

| Construct ID | Number of survived plants | Number of total plants | Survival rate (%) | Average recovery degree | P value | P ≤ 0.05 |
|---|---|---|---|---|---|---|
| DP0069 | 255 | 377 | 67.6 | 1.07 | 0.0013 | Y |
| ZH11-TC | 39 | 90 | 43.3 | 0.69 | | |
| DP0069 | 255 | 377 | 67.6 | 1.07 | 0.3830 | |
| DP0158 | 57 | 93 | 61.3 | 0.97 | | |

TABLE 74

Enhanced drought tolerance of OsEIL2 transgenic rice plants under greenhouse conditions (line level)

| Line ID | Number of survived plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0069.01 | 26 | 47 | 55.3 | 0.86 | 0.1747 | | 0.4121 | |
| DP0069.03 | 32 | 48 | 66.7 | 1.09 | 0.0015 | Y | 0.3220 | |
| DP0069.05 | 36 | 47 | 76.6 | 1.19 | 0.0001 | Y | 0.0758 | |
| DP0069.07 | 42 | 48 | 87.5 | 1.36 | 0.0000 | Y | 0.0017 | Y |
| DP0069.08 | 37 | 48 | 77.1 | 1.20 | 0.0001 | Y | 0.0616 | |

TABLE 74-continued

Enhanced drought tolerance of OsEIL2 transgenic rice plants under greenhouse conditions
(line level)

| Line ID | Number of survived plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0069.09 | 23 | 46 | 50.0 | 0.78 | 0.4976 | | 0.1338 | |
| DP0069.10 | 34 | 48 | 70.8 | 1.15 | 0.0003 | Y | 0.1528 | |
| DP0069.12 | 25 | 45 | 55.6 | 0.91 | 0.0790 | | 0.6739 | |
| ZH11-TC | 39 | 90 | 43.3 | 0.69 | | | | |
| DP0158 | 57 | 93 | 61.3 | 0.97 | | | | |

Example 8

Laboratory Paraquat Assays of Transgenic Rice Plants

Paraquat (1,1-dimethyl-4,4-bipyridinium dichloride), is a foliar-applied and non-selective bipyridinium herbicide, and it is one of the most widely used herbicides in the world, controlling weeds in a huge variety of crops like corn, rice, soybean etc. In plant cells, paraquat mainly targets chloroplasts by accepting electrons from photosystem I and then reacting with oxygen to produce superoxide and hydrogen peroxide, which cause photooxidative stress. Drought stress and cold stress usually leads to increased reactive oxygen species (ROS) in plants and sometimes, the drought and/or cold tolerance of plant is associated with enhanced antioxidative ability. Paraquat is a potent oxidative stress inducer; it greatly increases the ROS production and inhibits the regeneration of reducing equivalents and compounds necessary for the activity of the antioxidant system. The ROS generation is enhanced under abiotic stress conditions, and the plant responses range from tolerance to death depending on the stress intensity and its associated-ROS levels. Relative low level of paraquat can mimic the stress-associated ROS production and used as a stress tolerance marker in plant stress biology (Hasaneen M. N. A. (2012) Herbicide-Properties, Synthesis and Control of Weeds book). Therefore, the paraquat tolerance of the drought tolerant and cold tolerant transgenic rice plants was tested.

Paraquat Assay Methods:

Transgenic rice plants from eight-ten transgenic lines of each transgenic rice line were tested by paraquat assay. Tissue-cultured Zhonghua 11 plants (ZH11-TC) and empty vector transgenic plants (DP0158) were used as controls. $T_2$ transgenic seeds were sterilized and germinated as described in Example 4, and this assay was carried out in growth room with temperature at 28-30° C. and humidity ~30%. The germinated seeds were placed in a tube with a hole at the bottom, and water cultured at 30° C. for 5 days till one-leaf and one-terminal bud stage. Uniform seedlings about 3.5-4 cm in height were selected for paraquat testing. Randomized block design was used in this experiment. There were five blocks, each of which has 16×12 holes. Each transgenic line was placed in one row (12 plants/line), and ZH11-TC and DP0158 seedlings were placed in 3 rows (3×12 plants) randomly in one block. Then the seedlings were treated with 0.8 µM paraquat solution for 7 days at 10 h day/14 h night, and the treated seedlings first encountered dark and took up the paraquat solution which was changed every two days. After treated for 7 days, the green seedlings were counted. Those seedlings that maintain green in whole without damage were considered as paraquat tolerant seedling; those with bleached leaves or stem were not considered as paraquat tolerant seedling.

Tolerance rate was used as a parameter for this trait screen, which is the percentage of plants which kept green and showed tolerant phenotype over the total plant number.

The data was analyzed at construct level (all transgenic plants compared with the control) and transgenic line level (different transgenic lines compared with the control) using a statistic model of "Y~seg+line (seg)+rep+error", random effect of "rep", Statistic Method of "SAS Proc Glimmix".

Paraquat Assay Results:

1) DP0069 Transgenic Rice

In the first experiment, after paraquat solution treated, 489 of the 600 OsEIL2 transgenic seedlings (82%) kept green and showed tolerant phenotype, while 80 of the 180 (44%) seedlings from ZH11-TC showed tolerant phenotype, and 87 of the 180 (48%) DP0158 seedlings showed tolerant phenotype. The tolerance rate of all screened OsEIL2 transgenic seedlings was significantly greater than ZH11-TC (P value=0.0000) and DP0158 (P value=0.0000) controls. These results indicate that the OsEIL2 transgenic seedlings exhibited enhanced paraquat tolerance compared to both ZH11-TC and DP0158 seedlings at construct level.

Analysis at transgenic line level indicates that all the ten lines exhibited significantly greater tolerance rates compared with ZH11-TC and DP0158 controls (Table 75). These results demonstrate that OsEIL2 transgenic rice plants had enhanced paraquat tolerance at construct and transgenic line level at seedling stages. OsEIL2 functions in enhancing paraquat tolerance or antioxidative ability of transgenic plants.

TABLE 75

Paraquat tolerance assay of OsEIL2 transgenic rice plants at transgenic line level (1st experiment)

| Line ID | Number of tolerant seedlings | Number of total seedlings | Tolerance rate (%) | CK = ZH11-TC P value | P ≤ 10.05 | CK = DP0158 P value | P ≤ 10.05 |
|---|---|---|---|---|---|---|---|
| DP0069.01 | 51 | 60 | 85 | 0.0000 | Y | 0.0000 | Y |
| DP0069.02 | 53 | 60 | 88 | 0.0000 | Y | 0.0000 | Y |
| DP0069.03 | 55 | 60 | 92 | 0.0000 | Y | 0.0000 | Y |
| DP0069.05 | 48 | 60 | 80 | 0.0000 | Y | 0.0001 | Y |
| DP0069.07 | 53 | 60 | 88 | 0.0000 | Y | 0.0000 | Y |
| DP0069.08 | 47 | 60 | 78 | 0.0000 | Y | 0.0002 | Y |
| DP0069.09 | 46 | 60 | 77 | 0.0000 | Y | 0.0005 | Y |
| DP0069.11 | 37 | 60 | 62 | 0.0253 | Y | 0.0798 | |
| DP0069.12 | 51 | 60 | 85 | 0.0000 | Y | 0.0000 | Y |
| DP0069.15 | 48 | 60 | 80 | 0.0000 | Y | 0.0001 | Y |
| ZH11-TC | 80 | 180 | 44 | | | | |
| DP0158 | 87 | 180 | 48 | | | | |

In the second experiment, after paraquat solution treated, 362 of the 600 (60%) OsEIL2 transgenic rice kept green and showed tolerant phenotype, whereas 93 of the 180 (52%) ZH11-TC seedlings showed tolerance phenotype, and 78 of the 180 (43%) DP0158 seedlings showed tolerance. The tolerance rate of OsEIL2 transgenic rice was significantly greater than both of ZH11-TC (P value=0.0193) and DP0158 (P value=0.0000) seedlings.

Analysis at transgenic level was shown in Table 76. All the ten lines exhibited greater tolerance rates than DP0158 control, and six lines exhibited greater tolerance rates than ZH11-TC control. Two lines showed significantly greater tolerance rates than ZH11-TC seedlings, and five lines showed significantly greater tolerance rates than DP0158 seedlings. These results clearly demonstrate that OsEIL2 had enhanced paraquat tolerance or antioxidative ability of transgenic plants.

lite (V:V=1:2). Five transgenic rice plants from each line were planted in one pot, and about 25 plants were plated in six pots which were placed in different position in one tray. The seedlings were grown under normal greenhouse condition and watered by modified IRRI solution for 18-21 days. When grown to 3-leaf stage, the seedlings were transferred into artificial chamber at 4° C. and stressed for 3-5 days until the leaves of 50% plants became curved. Then the plants were transferred into greenhouse to recover for 5-7 days, and the plants were scored for the degree of recovery. The following scoring system was used: more than half green stem=1, more than two third green leaf=1, less than two third but more than one third green leaf=0.5, less than one third green leaf=0.2, no green leaf or less than half green stem=0. The recovery degree was the sum of the score of the green tissues, and the data were statistically analyzed using

TABLE 76

Paraquat tolerance assay of OsEIL2 transgenic rice plants at transgenic line level (2nd experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0069.01 | 54 | 60 | 90 | 0.0000 | Y | 0.0000 | Y |
| DP0069.03 | 39 | 60 | 65 | 0.0786 | | 0.0056 | Y |
| DP0069.05 | 30 | 60 | 50 | 0.8238 | | 0.3726 | |
| DP0069.07 | 39 | 60 | 65 | 0.0786 | | 0.0056 | Y |
| DP0069.08 | 29 | 60 | 48 | 0.6563 | | 0.5025 | |
| DP0069.09 | 34 | 60 | 57 | 0.5043 | | 0.0792 | |
| DP0069.10 | 37 | 60 | 62 | 0.1843 | | 0.0176 | Y |
| DP0069.11 | 27 | 60 | 45 | 0.3751 | | 0.8223 | |
| DP0069.12 | 44 | 60 | 73 | 0.0054 | Y | 0.0002 | Y |
| DP0069.15 | 29 | 60 | 48 | 0.6563 | | 0.5025 | |
| ZH11-TC | 93 | 180 | 52 | | | | |
| DP0158 | 78 | 180 | 43 | | | | |

Example 9

Cold Assays of Transgenic Rice Plants Under Low Temperature Conditions

Nine to twelve lines per construct were tested for cold assay. $T_2$ Transgenic seeds were sterilized as described in Example 4. The germinated seeds were sowed in a pot (8×8×8 cm) filled with mixture of organic soil and vermicu- Mixed Model. The lines which showed significant better than controls (P<0.05) were considered as positive ones.

Survival rate (percentage of survived plants over the total plant number) was also used as a parameter for cold screening.

Results:
DP0069 Transgenic Rice
In the first experiment, seven lines were tested. After cold stressed at 4° C. for four days and recovered in greenhouse for seven days, 49% of the OsEIL2 transgenic rice survived, 26% of ZH11-TC survived and 44% of DP0158 seedlings survived. At the line level (Table 77), all the seven lines exhibited higher survival rates and recovery degrees than that of ZH11-TC control; and five lines showed higher survival rates and recovery degrees than that of DP0158 control. These results indicate that OsEIL2 transgenic rice had enhanced cold tolerance than control at seedling stage.

TABLE 77

Enhanced cold tolerance of OsEIL2 transgenic rice plants under low temperature conditions (1$^{st}$ experiment)

| Line ID | Number of survived plants | Number of total plants | Survival rate (%) | Average recovery degree | CK = ZH11-TC | | CK = DP0158 | |
|---|---|---|---|---|---|---|---|---|
| | | | | | P value | P ≤ 0.05 | P value | P ≤ 0.05 |
| DP0069.01 | 17 | 25 | 68 | 1.26 | 0.0176 | Y | 0.3941 | |
| DP0069.02 | 13 | 25 | 52 | 1.10 | 0.0669 | | 0.6756 | |
| DP0069.03 | 14 | 25 | 56 | 1.14 | 0.0492 | Y | 0.5988 | |
| DP0069.05 | 11 | 23 | 48 | 1.09 | 0.0741 | | 0.7027 | |
| DP0069.08 | 12 | 25 | 48 | 1.05 | 0.0994 | | 0.7864 | |
| DP0069.09 | 10 | 25 | 40 | 0.97 | 0.1609 | | 0.9408 | |
| DP0069.11 | 7 | 25 | 28 | 0.94 | 0.1956 | | 0.9904 | |
| ZH11-TC | 13 | 50 | 26 | 0.55 | | | | |
| DP0158 | 11 | 25 | 44 | 0.94 | | | | |
| DP0069 (construct) | 84 | 173 | 49 | 1.08 | 0.0476 | Y | 0.6994 | |

In the second experiment, the same seven transgenic lines were tested. When the plants growing to 3-leaf stage, they were placed in cold chamber and stressed for four days at about 4° C., and recovered in room temperature for eight days; then these plants were cold stressed for four days for the second time and recovered for four days. 132 of the 209 (63%) transgenic rice survived, whereas, 26 of the 60 (43%) ZH11-TC and 9 of the 29 (31%) DP0158 seedlings survived. The OsEIL2 transgenic rice exhibited higher survival rate and significantly higher recovery degree than both ZH11-TC and DP0158 controls. As shown in Table 78, five lines exhibited higher survival rates than ZH11-TC and seven lines exhibited higher survival rates; and all the seven lines showed higher average recovery degrees than ZH11-TC and DP0158 controls. These results further demonstrate that OsEIL2 transgenic rice gained enhanced cold tolerance, and OsEIL2 plays a role in enhancing cold tolerance.

Example 10

Transformation and Evaluation of Maize with Rice Low Nitrogen Tolerance Genes

Maize plants can be transformed to over-express *Oryza sativa* low nitrogen tolerance genes or a corresponding homolog from maize, *Arabidopsis*, or other species. Expression of the gene in the maize transformation vector can be under control of a constitutive promoter such as the maize ubiquitin promoter (Christensen et al. (1989) *Plant Mol. Biol.* 12:619-632 and Christensen et al. (1992) *Plant Mol. Biol.* 18:675-689) or under control of another promoter, such as a stress-responsive or tissue-preferred promoter. The recombinant DNA construct can be introduced into maize cells by particle bombardment substantially as described in International Patent Publication WO 2009/006276. Alternatively, maize plants can be transformed with the recombinant DNA construct by *Agrobacterium*-mediated transformation substantially as described by Zhao et al. in *Meth. Mol. Biol.* 318:315-323 (2006) and in Zhao et al., *Mol. Breed.* 8:323-333 (2001) and U.S. Pat. No. 5,981,840 issued Nov. 9, 1999. The *Agrobacterium*-mediated transformation process involves bacterium inoculation, co-cultivation, resting, selection and plant regeneration.

TABLE 78

Enhanced cold tolerance of OsEIL2 transgenic rice plants under low temperature conditions (2$^{nd}$ experiment)

| Line ID | Number of survived plants | Number of total plants | Survival rate (%) | Average recovery degree | CK = ZH11-TC | | CK = DP0158 | |
|---|---|---|---|---|---|---|---|---|
| | | | | | P value | P ≤ 10.05 | P value | P ≤ 10.05 |
| DP0069.01 | 13 | 30 | 43 | 1.50 | 0.2517 | | 0.0955 | |
| DP0069.02 | 12 | 30 | 40 | 1.43 | 0.3403 | | 0.1315 | |
| DP0069.03 | 18 | 30 | 60 | 1.62 | 0.1465 | | 0.0549 | |
| DP0069.05 | 20 | 30 | 67 | 1.81 | 0.0553 | | 0.0212 | Y |
| DP0069.08 | 26 | 30 | 87 | 2.22 | 0.0032 | Y | 0.0016 | Y |
| DP0069.09 | 20 | 30 | 67 | 1.76 | 0.0732 | | 0.0278 | Y |
| DP0069.11 | 23 | 29 | 79 | 1.95 | 0.0232 | Y | 0.0095 | Y |
| ZH11-TC | 26 | 60 | 43 | 1.05 | | | | |
| DP0158 | 9 | 29 | 31 | 0.70 | | | | |
| DP0069 (construct) | 132 | 209 | 63 | 1.76 | 0.0373 | Y | 0.0153 | Y |

Progeny of the regenerated plants, such as $T_1$ plants, can be subjected to a low nitrogen stress. Using image analysis, plant area, volume, growth rate and color can be measured at multiple times before and during low nitrogen stress. Significant delay in leaf area reduction, a reduced yellow-color accumulation, and/or an increased growth rate during low nitrogen stress, relative to a control, will be considered evidence that the gene functions in maize to enhance NUE.

Example 11

Transformation and Evaluation of Gaspe Flint Derived Maize Lines

As described in Example 10, maize plants can be transformed to over-express the rice low nitrogen tolerance genes, or corresponding homologs from another species. In certain circumstances, recipient plant cells can be from a uniform maize line which having a short life cycle ("fast cycling"), a reduced size, and high transformation potential, and are disclosed in Tomes et al. U.S. Pat. No. 7,928,287.

The population of transgenic ($T_0$) plants resulting from the transformed maize embryos can be grown in a controlled greenhouse environment using a modified randomized block design to reduce or eliminate environmental error. For example, a group of 30 plants, comprising 24 transformed experimental plants and 6 control plants (collectively, a "replicate group"), are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of 30 plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

Each plant in the line population is identified and tracked throughout the evaluation process, and the data gathered from that plant are automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor (U.S. Pat. Nos. 7,403,855 and 7,702,462).

Each greenhouse plant in the $T_0$ line population, including any control plants, is analyzed for agronomic characteristics of interest, and the agronomic data for each plant are recorded or stored in a manner so as to be associated with the identifying data for that plant. Confirmation of a phenotype (gene effect) can be accomplished in the $T_1$ generation with a similar experimental design to that described above.

Example 12

Laboratory NUE Assays of Rice Low Nitrogen Tolerance Genes in *Arabidopsis*

To understand whether rice low nitrogen tolerance genes can improve dicot plants' low nitrogen tolerance, or other traits, rice low nitrogen tolerance gene over-expression vectors were transformed into *Arabidopsis* (Columbia) using floral dip method by *Agrobacterium* mediated transformation procedure and transgenic plants were identified (Clough, S. T. and Bent, A. F. (1998) *The Plant Journal* 16, 735-743; Zhang, X. et al. (2006) *Nature Protocols* 1: 641-646).

A 16.8-kb T-DNA based binary vector which is called pBC-yellow was used. This vector contains the RD29a promoter driving expression of the gene for ZS-Yellow, which confers yellow fluorescence to transformed seed. The genes were cloned as described in Example 1, and constructed in the Gateway vector. Then using the INVITROGEN™ GATEWAY® technology, an LR Recombination Reaction was performed on the entry clone containing the directionally cloned PCR product and the pBC-yellow vector to generate vectors for transforming *Arabidopsis*.

Growth Chamber NUE Screening Method:

The $T_1$ generation fluorescent seeds are selected, surface sterilized and stratified in the dark at 4° C. for three days. Then 32 $T_1$ individuals are sown next to 32 empty vector control (pBCyellow-empty vector) individuals on one low nitrogen media containing 0.5× N-Free Hoagland's, 0.4 mM potassium nitrate, 0.1% sucrose, 1 mM MES and 0.25% Phytagel™ as shown in Table 77. Two repeats are prepared. The plates are horizontally placed in the growth chamber and cultured for a period of 10 days at 22° C., 60% relative humidity and a 16 hour day cycle. Seedling status is evaluated by imaging the entire plate from 10-13 days after stratifications.

After masking the plate image to remove background color, two different measurements are collected for each individual: total rosette area, and the percentage of color that falls into a green color bin. Using hue, saturation and intensity data (HSI), the green color bin consists of hues 50 to 66. Total rosette area is used as a measure of plant biomass, whereas the green color bin is shown by dose-response studies to be an indicator of nitrogen assimilation (patent application US20110209245).

The images are analyzed using Nitrosight software and the number of Pixel (for size of the plants) and the intensity of Bin2 (for green color of leaves) for each of the 32/64 transgenic seedlings are compared with 32/64 seedlings of empty vector control for similar parameters. The green color and better growth of the seedling as compared to the empty vector control seedling signifies improved NUE. The data is statistically analyzed and a gene was considered as a weak validation with a P value less than $10^{-4}$ and a strong validation at $10^{-5}$ for Bin2 and Area in replicates and multiple days (Day 10 to Day 13 of assay).

TABLE 79

Modified Hoagland's nutrient solution for culturing Arabidopsis

| Molecular formula | Molecular weight | Concentration (mM) |
|---|---|---|
| $KNO_3$ | 101.1 | 0.4 |
| $MgSO_4 \cdot 7H_2O$ | 246.49 | 1.0 |
| $CaCl_2$ | 110.98 | 2.5 |
| $Na_2HPO_4$ | 141.96 | 1.0 |
| $K_2SO_4$ | 174.26 | 1.3 |
| Fe—EDTA | 367.1 | $4.6 \times 10^{-3}$ |
| MES | 195.2 | 1.0 |
| $H_3BO_3$ | 61.84 | $12.5 \times 10^{-3}$ |
| $MnSO_4 \cdot H_2O$ | 169.01 | $1.0 \times 10^{-3}$ |
| $ZnSO_4 \cdot 7H_2O$ | 287.5 | $1.0 \times 10^{-3}$ |
| $CuSO_4 \cdot 5H_2O$ | 249.71 | $0.25 \times 10^{-3}$ |
| $Na_2MoO_4 \cdot 2H_2O$ | 241.95 | $0.25 \times 10^{-3}$ |

What is claimed is:

1. A plant or seed comprising a polynucleotide encoding a polypeptide comprising an amino acid sequence of at least 98% sequence identity to SEQ ID NO: 20, wherein the polynucleotide is operably linked to a heterologous regulatory element that increases the expression level of the polynucleotide compared to a control plant, wherein said plant exhibits increased nitrogen stress tolerance when compared to a control plant not comprising the polynucleotide operably linked to the heterologous regulatory element.

2. A method of increasing nitrogen stress tolerance in a plant, comprising:
   (a) expressing in the plant a polynucleotide operably linked to at least one heterologous regulatory element, wherein the polynucleotide encodes a polypeptide having an amino acid sequence of at least 98% sequence identity to SEQ ID NO: 20 and wherein the expression level of the polynucleotide is increased compared to that of a control plant; and
   (b) growing the plant, wherein said plant exhibits increased nitrogen stress tolerance when compared to a control plant not comprising the polynucleotide operably linked to the heterologous regulatory element.

3. The method of claim 2, wherein the plant is maize or rice.

4. The plant of claim 1, wherein the regulatory element is a promoter.

5. The plant of claim 1, wherein the regulatory element is an enhancer element.

6. The plant of claim 1, wherein the plant is maize.

7. The plant of claim 1, wherein the plant is rice.

* * * * *